US010888056B2

(12) United States Patent
Baxter et al.

(10) Patent No.: US 10,888,056 B2
(45) Date of Patent: Jan. 12, 2021

(54) TOMATO FRUIT HAVING INCREASED FIRMNESS

(71) Applicant: Syngenta Participations AG, Basel (CH)

(72) Inventors: Charles James Baxter, Grimoldby near Louth (GB); Natalie Helene Chapman, Loughborough (GB); Ian Puddephat, Reading (GB); Graham Barron Seymour, Loughborough (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/439,838

(22) Filed: Jun. 13, 2019

(65) Prior Publication Data

US 2019/0313594 A1   Oct. 17, 2019

Related U.S. Application Data

(62) Division of application No. 14/637,084, filed on Mar. 3, 2015, now Pat. No. 10,362,741, which is a division of application No. 13/500,149, filed as application No. PCT/EP2010/065575 on Oct. 15, 2010, now Pat. No. 8,987,549.

(30) Foreign Application Priority Data

Oct. 26, 2009 (EP) .................................... 09174072

(51) Int. Cl.
*A01H 1/00* (2006.01)
*A01H 5/08* (2018.01)
*C12N 15/82* (2006.01)
*A01H 6/82* (2018.01)

(52) U.S. Cl.
CPC ................. *A01H 5/08* (2013.01); *A01H 1/00* (2013.01); *A01H 6/825* (2018.05); *C12N 15/8242* (2013.01)

(58) Field of Classification Search
None
See application file for complete search history.

(56) References Cited

PUBLICATIONS

Eshed, Yuval et al.: "An Introgression Line Population of Lycopersicon pennellii in the Cultivated Tomato Enables the Identification and Fine Mapping of Yield-Associated QTL" in: Genetics 141, Genetics Society of America (1995), pp. 1147-1162.
Thompson, Andrew J. et al.: "Molecular and Genetic Characterization of a Novel Pleiotropic Tomato-Ripening Mutant" in: Plant Physiology 120, American Society of Plant Physiologists (1999), pp. 383-389.
Barone, A. et al.: "High-Throughput Genomics Enhances Tomato Breeding Efficiency" in: Current Genomics 10, Bentham Science Publishers (2009), pp. 1-9.
Sacks, E.J. and Francis, D.M., "Genetic and environmental variation for tomato flesh color in a population of modern breeding lines," 2001, J. Amer. Soc. Hort. Scie, 126(2): 221-226.
Bertin, N. & al.: "Identification of growth processes involved in QTLs for tomato fruit size and composition" in: Journal of Experimental Botany, vol. 60, No. 1, pp. 237-248, 2009.
Manning et al, 2006, Nature Gentics 38:948-952.
Eriksson et al, 2004, Plant Physiology 136:4184-4197.
Batu et al, 1998, Tr. J. Agr. & Forestry, 22, 365-372.
Geeson et al, 1985, J. Food Technol. 20:339-349.
Exama et al, 1993, J. Food, Sci. 58: 1365-1370.
Frary eet al, 2000, Science Washington, 2000: 289: 85-88.
Friedman et al, 2004, Science 305: 1786-1789.
W. R Pearson (1990), Methods inEnzymology 183: 63-98.
Tijssen (1993) Laboratory Techniques in Biochemistry and Molecular Biology-Hybridization with Nucleic Acid Probes part 1 chapter 2.
Knapp (2005), New nomenclature for Lycopersicon, http://sgn.cornell.edu/about/solanum_nomenclature.pl.
King et al, 2001, Theoretical and Applied Genetics 102: 1227-1235.
Causse et al (2002), J Exp Bot. Oct;53(377):2089-98.
Zietkiewicz et al., 1994, Genomics 94: 176-183.
Paterson AH (1996) Making genetic maps. In: Paterson AH (ed) Genome mapping in plants. RG Landes, San Diego, pp. 23-39.
Tsuchimoto et al., 1993, Plant Cell 5, 843-853.
Kado, 1991, Crit. Rev. Plant Sd. 10:1-32.
Horsch et al., 1985, Science 227:1229-1231.
Miki et al., 1993, Procedures for Introducing Foreign DNA into Plants. In: Glick BR and Thompson JE (Eds.) Methods in Plant Molecular Biology & Biotechnology, CRC Press, pp. 67-88.
Phillips et al., 1988, Cell/tissue culture and in vitro manipulation. In: G.F. Sprague & J. W. Dudley, eds. Corn and corn improvement, 3rd ed., p. 345-387.
Sanford et al., 1987, J. Particulate Sd. Technol. 5:27-37.
Hain et al. 1985, Mol. Gen. Genet. 199:161-168.
Laursen et al., 1994, http://sgn.cornell.edu/about/solanum_nomenclature.pl Laursen CM, Krzyzek RA, Flick CE, Anderson PC, Spencer TM ( 994) Production of fertile transgenic maize by electroporation of suspension culture cells. Plant Mol Biol. 24(1 ):51-61.
D'Halluin et al., 1992, Plant.Cell 4:1495-1505.
Draper et al., 1982, Plant and Cell Physiol. 23:451-458.
Christou et al., 1987, PNAS, 84:3962-3966.

(Continued)

*Primary Examiner* — Phuong T Bui
(74) *Attorney, Agent, or Firm* — Karen A. Magri

(57) ABSTRACT

This invention relates to a tomato fruit with significantly increased firmness due to the presence of at least one genetic element (or quantitative trait loci; QTLs) in the cultivated plant producing said tomato fruit, compared to fruit from a control tomato plant which does not have said genetic element(s). A cultivated tomato plant producing tomato fruit with significantly increased fruit firmness and a method for detecting QTLs linked to significantly increased fruit firmness are also provided.

4 Claims, 24 Drawing Sheets

Specification includes a Sequence Listing.

(56) References Cited

PUBLICATIONS

Deshayes et al., 1985, EMBO J. 4:2731-2737.
Zhang et al., 1991, Biotechnology 9:996-997.
Sanford et al., 1993, Methods in Enzymology 217:483-509.
Klein et al., 1992, Bio/Technology 10:286-291.
Sanford, 1990, Physiologica Plantarum 79: 206-209.
Sanford, 1988, Trends in Biotechnology 6:299-302.
Klein et al., 1988, Biotechnology 6:559-563.
Zhao et al., 2004, "Bacterial Artificial Chromosomes," Methods in Molecular Biology, vol. 255, Humana Press Inc., Totowa, N.J., USA.
Hamilton, 1997, Gene 200:107-1 16.
Nakagawa et al., Bioscience biotechnology Biochemistry, 71 (8), 2095-2010, 2007.
Atmosphere Proc. EURASIA Sym. on Quality Management in Postharvest Systems. Acta Hort. 804, ISHS 2008.
Chi et al, 2008, Plant Physiol. 147: 573-584.
Dik et al.,(1999) Eur. J. Plant Pathol. 105:1 15-122.
Eckstein F (ed) (1991 ) Oligonucleotides and Analogues, A Practical Approach. Oxford Univ. Press, NY 1991.
Eshed et al., Euphytica. Dordrecht: Kluwer Academic Publishers. 1994 79: 175-179.
Glick BR and Thompson JE (eds) (1993) Procedures for Introducing Foreign DNA into Plants in Methods in Plant Molecular Biology & Biotechnology, CRC Press, pp. 67-88. Gruber MY, Crosby WL (1993) Vectors for Plant Transformation. In: Glick BR and Thompson JE.
Moloney et al., 1989, Plant Cell Reports 8:238-242.
Nesbitt et al., (2001) Plant Physiol. 127: 575-583.
Pierik RLM (1999) In vitro Culture of Higher Plants, 4th edition, 360 pages, ISBN:0-7923-5267-X.
Sambrook J, and Russell DW (2001 ). Molecular Cloning: A Laboratory Manual. New York, NY, USA., Cold Spring Harbor Laboratory Press.
Smith et al., 1981, Molecular Sequences J. Mol. Biol: 147, 195-197.
Thompson et al., 1999, Plant Physiology 120:383-389.
Van Berloo et al., (2001), Mol. Breeding 8: 187-195.
Van Ooijen JW, Maliepaard C (1996) MapQTL® version 4.0: Software for the calculation of QTL positions on genetic map. CPRO-DLO, Wageningen van Oijen JW, Voorips RE (2001 ) JoinMap® 3.0: Software for the calculation of genetic linkage maps. Plant Research International, Wageningen, Netherlands.
Vrebalov et al., (2002) Locus. Science 296: 5566, 343-346.
Wang et al., (2007). Windows QTL Cartographer 2.5 Department of Statistics, North Carolina State University, Raleigh, NC.
Thompson, Andrew et a..: Molecular and Genetic Characterization of a Novel Pleiotropic Tomato-Ripening Mutant Plant Physiology, Jun. 1999, vol. 120, pp. 383-389
CA Office Action dated Sep. 13, 2017 for CA appl. No. 2773471.

| A | 113 | 124 | 142 | 301 | 331 |
|---|---|---|---|---|---|
| CT255 | A | H | H | H | H |
| ST0086 | A | H | H | H | H |
| NT2525 | A | H | H | H | H |
| NT5752 | A | H | H | H | H |
| NT5751 | A | H | H | H | H |
| NT3853 | A | H | A | H | H |
| NT3907 | A | H | A | B | H |
| NT3061 | A | H | A | B | H |
| TG451 | H | H | A | B | H |
| NT1974 | H | H | A | B | H |
| NT54PR22 | H | H | A | B | H |
| NT5496 | H | H | A | B | H |
| Le014988 | H | H | A | B | H |
| TG14 | H | H | A | B | H |
| R102 | H | H | A | B | H |
| PH3300 | H | H | A | B | H |
| PH3700 | H | H | A | B | H |
| PH3715 | H | H | A | B | H |
| HOX7A | H | H | A | B | H |
| NT1606 | H | H | A | B | H |
| cLET119 | H | H | A | B | H |
| CT277 | H | H | A | B | H |
| CT169 | H | H | A | B | H |
| Le0005 | H | H | A | B | H |
| Lm0127 | H | H | A | B | H |
| Lm4500 | H | H | A | B | H |
| Lm1650 | H | A | A | B | H |
| Lm1700 | H | A | A | B | H |
| HBa0329 | H | A | A | B | H |
| HBa0161 | H | A | A | B | H |
| Ie12281 | H | A | A | B | H |
| LE5100 | H | A | A | B | H |
| Le2150 | H | A | A | B | H |
| Le5200 | H | A | A | B | B |
| HBa0323 | H | A | A | B | B |
| HB5350 | H | A | A | B | B |
| HB2600 | H | A | A | B | B |
| HBa0212 | H | A | A | B | B |
| Lm0008 | H | A | A | B | B |
| GeneA3 | H | A | A | B | B |
| TG353 | H | A | A | B | B |
| TG567 | H | A | A | B | B |
| NT1541 | A | A | A | A | A |
| TG493 | A | A | A | A | A |
| NT3011 | A | A | A | A | A |
| NT3778 | A | A | A | A | A |
| NT3005 | A | A | A | A | A |
| ST0092 | A | A | A | A | A |
| TG527 | A | A | A | A | A |
| NT6002 | A | A | A | A | A |

Fig. 3

| B | 654 | 769 | 886 | 910 |
|---|---|---|---|---|
| CT255 | * | * | * | * |
| ST0086 | * | * | * | * |
| NT2525 | * | * | * | * |
| NT5752 | * | * | * | * |
| NT5751 | * | * | * | * |
| NT3853 | A | * | B | A |
| NT3907 | A | B | B | A |
| NT3061 | A | B | B | A |
| TG451 | A | B | B | A |
| NT1974 | A | B | B | A |
| NT54PR22 | A | B | B | A |
| NT5496 | A | B | B | A |
| Le014988 | A | B | B | A |
| TG14 | A | B | B | A |
| R102 | A | B | B | A |
| PH3300 | A | B | B | A |
| PH3700 | A | B | B | A |
| PH3715 | A | B | B | A |
| HOX7A | A | B | B | A |
| NT1606 | A | B | B | A |
| cLETl19 | A | B | B | A |
| CT277 | A | B | B | A |
| CT169 | A | B | B | A |
| Le0005 | A | B | B | A |
| Lm0127 | A | B | B | A |
| Lm4500 | A | B | B | A |
| Lm1650 | H | B | B | A |
| Lm1700 | H | B | B | A |
| HBa0329 | H | B | B | A |
| HBa0161 | H | B | B | A |
| Ie12281 | H | B | B | A |
| LE5100 | H | B | B | A |
| Le2150 | H | B | B | A |
| Le5200 | H | H | B | A |
| HBa0323 | H | H | B | A |
| HB5350 | H | H | B | A |
| HB2600 | H | H | H | A |
| HBa0212 | H | H | H | A |
| Lm0008 | H | H | H | A |
| GeneA3 | H | H | H | A |
| TG353 | H | H | H | A |
| TG567 | H | H | H | A |
| NT1541 | H | H | H | A |
| TG493 | H | H | H | A |
| NT3011 | H | H | H | A |
| NT3778 | H | H | H | A |
| NT3005 | H | H | H | A |
| ST0092 | H | H | H | H |
| TG527 | H | H | H | H |
| NT6002 | H | H | * | H |

Fig. 3

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial
<220> FEATURE:
<223> OTHER INFORMATION: Artificially synthesised oligonucleotide primer
      NT3853F used to screen for the presence or absence of SSR marker
      NT3853

<400> SEQUENCE: 1
ggattgtgtt atctccgatg                                              20

<210> SEQ ID NO 2
<211> LENGTH: 19
<212> TYPE: DNA
<213> ORGANISM: Artificial
<220> FEATURE:
<223> OTHER INFORMATION: Artificially synthesised oligonucleotide primer
      NT3853R used to screen for the presence or absence of SSR marker
      NT3853

<400> SEQUENCE: 2
gaaaaaggga agagatggg                                               19

<210> SEQ ID NO 3
<211> LENGTH: 18
<212> TYPE: DNA
<213> ORGANISM: Artificial
<220> FEATURE:
<223> OTHER INFORMATION: Artificially synthesised oligonucleotide primer
      NT3907F used to screen for the presence or absence of SSR marker
      NT3907

<400> SEQUENCE: 3
gaacagtttc cggtggag                                                18

<210> SEQ ID NO 4
<211> LENGTH: 18
<212> TYPE: DNA
<213> ORGANISM: Artificial
<220> FEATURE:
<223> OTHER INFORMATION: Artificially synthesised oligonucleotide primer
```

NT3907R used to screen for the presence or absence of SSR marker
NT3907

<400> SEQUENCE: 4
ttgggccagg aagaaaac                                              18

<210> SEQ ID NO 5
<211> LENGTH: 20
<212> TYPE: DNA
<213> ORGANISM: Artificial
<220> FEATURE:
<223> OTHER INFORMATION: Artificially synthesised oligonucleotide primer
TG14F used to screen for the presence or absence of SNP marker
TG14

<400> SEQUENCE: 5
gccaactgat tgcctatcct                                            20

<210> SEQ ID NO 6
<211> LENGTH: 20
<212> TYPE: DNA
<213> ORGANISM: Artificial
<220> FEATURE:
<223> OTHER INFORMATION: Artificially synthesised oligonucleotide primer
TG14R used to screen for the presence or absence of SNP marker
TG14

<400> SEQUENCE: 6
ctcactccac ccatcacaac                                            20

<210> SEQ ID NO 7
<211> LENGTH: 20
<212> TYPE: DNA
<213> ORGANISM: Artificial
<220> FEATURE:
<223> OTHER INFORMATION: Artificially synthesised oligonucleotide primer
HOX7AF used to screen for the presence or absence of SNP marker
HOX7A

<400> SEQUENCE: 7
tgactccggc aaatttctct                                            20

<210> SEQ ID NO 8
<211> LENGTH: 20
<212> TYPE: DNA
<213> ORGANISM: Artificial
<220> FEATURE:
<223> OTHER INFORMATION: Artificially synthesised oligonucleotide primer
HOX7AR used to screen for the presence or absence of SNP marker
HOX7A

<400> SEQUENCE: 8
tcccccatgt atggactgat                                            20

<210> SEQ ID NO 9
<211> LENGTH: 20
<212> TYPE: DNA
<213> ORGANISM: Artificial
<220> FEATURE:
<223> OTHER INFORMATION: Artificially synthesised oligonucleotide primer
CT277F used to screen for the presence or absence of SNP marker
CT277

<400> SEQUENCE: 9
tggtaacctg ctgtggtcaa                                            20

<210> SEQ ID NO 10

-continued

```
<211> LENGTH: 20
<212> TYPE: DNA
<213> ORGANISM: Artificial
<220> FEATURE:
<223> OTHER INFORMATION: Artificially synthesised oligonucleotide primer
      CT277R used to screen for the presence or absence of SNP marker
      CT277

<400> SEQUENCE: 10
aggtaaaccg ccagctcatt                                              20

<210> SEQ ID NO 11
<211> LENGTH: 20
<212> TYPE: DNA
<213> ORGANISM: Artificial
<220> FEATURE:
<223> OTHER INFORMATION: Artificially synthesised oligonucleotide primer
      Lm0127F used to screen for the presence or absence of SNP marker
      Lm0127

<400> SEQUENCE: 11
gaaaggatgc agccaaaaat                                              20

<210> SEQ ID NO 12
<211> LENGTH: 20
<212> TYPE: DNA
<213> ORGANISM: Artificial
<220> FEATURE:
<223> OTHER INFORMATION: Artificially synthesised oligonucleotide primer
      Lm0127R used to screen for the presence or absence of SNP marker
      Lm0127

<400> SEQUENCE: 12
tactctaagg gcgcacaatg                                              20

<210> SEQ ID NO 13
<211> LENGTH: 20
<212> TYPE: DNA
<213> ORGANISM: Artificial
<220> FEATURE:
<223> OTHER INFORMATION: Artificially synthesised oligonucleotide primer
      Lm1650F used to screen for the presence or absence of SNP marker
      Lm1650

<400> SEQUENCE: 13
aggttggcag aagacgaaga                                              20

<210> SEQ ID NO 14
<211> LENGTH: 20
<212> TYPE: DNA
<213> ORGANISM: Artificial
<220> FEATURE:
<223> OTHER INFORMATION: Artificially synthesised oligonucleotide primer
      Lm1650R used to screen for the presence or absence of SNP marker
      Lm1650

<400> SEQUENCE: 14
acatcccaaa gagctccaga                                              20

<210> SEQ ID NO 15
<211> LENGTH: 20
<212> TYPE: DNA
<213> ORGANISM: Artificial
<220> FEATURE:
<223> OTHER INFORMATION: Artificially synthesised oligonucleotide primer
      LE5100F used to screen for the presence or absence of SNP marker
      LE5100

<400> SEQUENCE: 15
```
tgttccaaac gcctaaaacc                                          20

<210> SEQ ID NO 16
<211> LENGTH: 20
<212> TYPE: DNA
<213> ORGANISM: Artificial
<220> FEATURE:
<223> OTHER INFORMATION: Artificially synthesised oligonucleotide primer
      LE5100R used to screen for the presence or absence of SNP marker
      LE5100

<400> SEQUENCE: 16
ttccccaagt gattcctcag                                          20

<210> SEQ ID NO 17
<211> LENGTH: 20
<212> TYPE: DNA
<213> ORGANISM: Artificial
<220> FEATURE:
<223> OTHER INFORMATION: Artificially synthesised oligonucleotide primer
      LE5200F used to screen for the presence or absence of SNP marker
      LE5200

<400> SEQUENCE: 17
tttgtacaag cggcacaaag                                          20

<210> SEQ ID NO 18
<211> LENGTH: 20
<212> TYPE: DNA
<213> ORGANISM: Artificial
<220> FEATURE:
<223> OTHER INFORMATION: Artificially synthesised oligonucleotide primer
      LE5200R used to screen for the presence or absence of SNP marker
      LE5200

<400> SEQUENCE: 18
cagctcgcgt catctcatta                                          20

<210> SEQ ID NO 19
<211> LENGTH: 20
<212> TYPE: DNA
<213> ORGANISM: Artificial
<220> FEATURE:
<223> OTHER INFORMATION: Artificially synthesised oligonucleotide primer
      HB2600F used to screen for the presence or absence of SNP marker
      HB2600

<400> SEQUENCE: 19
agggaggctg tgggtaagat                                          20

<210> SEQ ID NO 20
<211> LENGTH: 20
<212> TYPE: DNA
<213> ORGANISM: Artificial
<220> FEATURE:
<223> OTHER INFORMATION: Artificially synthesised oligonucleotide primer
      HB2600R used to screen for the presence or absence of SNP marker
      HB2600

<400> SEQUENCE: 20
ggcacctaga ccaaatccaa                                          20

<210> SEQ ID NO 21
<211> LENGTH: 20
<212> TYPE: DNA
<213> ORGANISM: Artificial
<220> FEATURE:

-continued

```
<223> OTHER INFORMATION: Artificially synthesised oligonucleotide primer
      TG353F used to screen for the presence or absence of SNP marker
      TG353

<400> SEQUENCE: 21
cagagcctga tctttcacca                                                   20

<210> SEQ ID NO 22
<211> LENGTH: 20
<212> TYPE: DNA
<213> ORGANISM: Artificial
<220> FEATURE:
<223> OTHER INFORMATION: Artificially synthesised oligonucleotide primer
      TG353R used to screen for the presence or absence of SNP marker
      TG353

<400> SEQUENCE: 22
ttcgtgttgg agatggaaag                                                   20
```

TOMATO FRUIT HAVING INCREASED FIRMNESS

CROSS-REFERENCE TO RELATED APPLICATIONS

This application is a divisional of U.S. application Ser. No. 14/637,084 (now U.S. Pat. No. 10,362,741 B2), filed Mar. 3, 2015, which is a divisional of U.S. application Ser. No. 13/500,149 (now U.S. Pat. No. 8,987,549 B2), which claims priority under 35 U.S.C. § 371 from PCT Application No. PCT/EP2010/065575, filed Oct. 15, 2010, which claims the benefit of European Patent Application No. 09174072.0, filed Oct. 26, 2009, the disclosures of which are incorporated by reference herein in their entirety.

STATEMENT REGARDING ELECTRONIC SUBMISSION OF A SEQUENCE LISTING

A Sequence Listing in ASCII test format, submitted under 37 C.F.R. 1.821, entitled "72652_ST25.txt", 111 kilobytes in size, generated on Feb. 12, 2015 and filed via EFS-Web is provided in lieu of a paper copy. This sequence listing is hereby incorporated by reference into the specification for its disclosure.

INTRODUCTION

For all fruit products, fruit firmness which is fit for purpose is essential to meet and possibly exceed consumer expectations. Consumers will reject products with an unacceptable fruit firmness, even though other quality attributes such as flavour and colour are good or excellent. Additionally, the supply chain requires an appropriate level of fruit firmness for the effective delivery of high quality fruit to retail outlets. Improving the quality of the raw materials will also encourage the development of healthier diets.

Tomato is the model system for studying fruit ripening due to extensive genetic and genomic resources. Fruit firmness in tomato is determined by a number of factors including cell wall structure, turgor and cuticle properties. Fruit firmness is a complex trait and depends on the action of many genes. This has made it difficult to dissect the events determining changes in fruit firmness by focusing on changes in cell wall degrading enzymes.

Harvesting tomato fruit when ripening has set in would make maturity determination easier as it would be based on visible peel color and would assure full quality development. After harvest, ripening continues and softening advances, increasing the susceptibility of the fruit to handling damage and limiting the marketing period. Slowing down the ripening and softening stages would allow harvesting, transport and storage of partially ripe but firm fruit (T. Chanthasombath et al, 2008).

Ripening mutants in tomato such as Colourless non-ripening and ripening inhibitor have yielded important insights into an emerging genetic framework which regulates ripening and modulates fruit firmness (Thompson et al, 1999; Vrebalov et al, 2002; Eriksson et al, 2004; Manning et al, 2006). Delaying ripening and softening may be achieved by employing modified atmosphere packaging (MAP) which has been extensively studied as a simple and cheap method of prolonging shelf life of many fruits and vegetables including tomato (Batu & Thompson, 1998, Exama et al, 1993, Geeson et al, 1985), however it increases the cost of packaging and handling of fruits. Existing methods to enhance fruit firmness in conventional plant breeding programs rely on screening fruit firmness differences in fruit harvested from mature plants. Any identification of enhanced fruit firmness in this scenario will largely be down to chance. Currently it is not financially viable or efficient to breed for enhanced fruit firmness due to the cost and complexity of growing and phenotyping large numbers of plants.

To bridge the gap between the emerging model for the regulation of fruit ripening and a full knowledge of the components involved in controlling fruit firmness will require additional strategies to those based on either targeting genes for known cell wall-related proteins or investigating pleiotropic ripening mutants. Fruit firmness is a quantitative trait involving many genes and yet the identity of the majority of these genes remains elusive.

Wild tomato species offer a rich and largely unexplored source of new genetic variation for breeders. Tanksley and Zamir (Frary et al, 2000; Fridman et al, 2004) have demonstrated that this source of genetic diversity can be used to understand the molecular basis of important fruit quality traits and provide new material for breeding.

It is thus apparent from the prior art that there is a need to modify tomato fruit firmness and to delay the softening of tomato fruits in particular so that the fruits stay on the vine for a longer period of time. The fruits would then remain firmer while accumulating more flavour and taste components and thus exhibit a final better taste compared to fruits that have been harvested earlier and ripened artificially with gas for example. Such increased firmness of the fruit would allow a longer period of time for harvesting since the fruits could be left on the vine without the associated softening which would be detrimental for the steps of handling, packing and delivery to the supermarket shelves.

SUMMARY OF THE INVENTION

An investigation has been conducted on the distribution of quantitative trait loci (QTL) for tomato fruit mechanical properties on the publicly available 'Zamir' lines (Eshed and Zamir, 1994). These are a set of 76 Solanum pennellii introgression lines (ILs) generated in a Solanum lycopersicum background (cv. M82). These ILs partition the genetic map into 107 bins that are defined by singular or overlapping S. pennellii segments. This targeted population, which allows 'Mendelisation' of QTL permits mapping and resolution of traits while using a manageable experimental system to take account of environmental effects.

The inventors have defined genetic elements (or QTL) which are surprisingly linked to significantly increased fruit firmness in tomato. The present invention therefore relates in a first aspect to a tomato fruit with significantly increased fruit firmness at the harvesting stage, preferably at the mature green stage, or at the breaker plus 7 days stage, wherein said increased fruit firmness is linked to said genetic elements in the cultivated tomato plant producing said tomato fruit, wherein said firmness is from between 1.2 to 2 times greater or, alternatively, 1.2 to 1.5 times greater than that of fruit from a control tomato plant which does not have these genetic elements. Introgression lines IL2-3 and IL2-4 (deposited under accession numbers LA4038 and LA4039 respectively), and which bear these genetic elements, showed a significant increase in fruit firmness compared to an M82 parental control with the most pronounced effects observed in IL2-3. There is a dominant effect of these genetic elements in the F1 generation and the trait is most apparent in ripe tomato fruit.

There is also provided a cultivated tomato plant which produces tomato fruit with increased firmness as described above, wherein said plant can be characterised by a) the at least one genetic element is linked to at least one DNA marker selected from the group consisting of NT3853, NT3907, TG14, HOX7A, CT277, HB2600, TG353, Lm0127, Lm1650, LE5100 and LE5200 and/or b) the at least one genetic element is complementary to the corresponding genetic element in S. pennellii lines IL2-3 and IL2-4, wherein the said genetic element in IL2-3 and IL2-4 is linked to at least one DNA marker selected from the said group in (a).

There is also provided a cultivated tomato plant wherein the at least one genetic element is one or more QTL selected from a) QTL1 linked to at least one of the DNA markers NT3853, NT3907 and TG14; b) QTL2 linked to at least one of the DNA markers HOX7A and CT277; c) QTL3 is linked to at least one of the DNA markers HB2600, TG353; d) QTL4 linked to at least one of the DNA markers Lm0127 and Lm1650; e) QTL5 linked to at least one of the DNA markers LE5100 and LE5200, and combinations of these QTLs thereof.

There is also provided a cultivated tomato plant as described above wherein the QTL is QTL1 linked to at least one of the DNA markers NT3853, NT3907 and TG14; which is present only in the inner pericarp.

There is also provided a cultivated tomato plant as described above wherein said plant is an inbred, a diploid or a hybrid. In a specific embodiment, the plant is male sterile.

There is also provided a tomato seed which produces a cultivated tomato plant of the present invention.

There is also provided a plant part of a cultivated tomato plant as described herein. In a specific embodiment there is provided plant material obtainable from a plant part of a cultivated tomato plant as described herein.

The above identified DNA markers represent a rapid assay and research tool to select for cultivated tomato plants containing a defined genetic region. These DNA markers yield the potential to manipulate a very small and well defined genetic region which is linked to increased fruit firmness. This has the advantage of allowing the screening of large numbers (1000's) of plants at a very early stage of development for desirable combinations of DNA markers and will allow the enhancement of fruit firmness in commercial varieties of tomato.

There is also provided a method for detecting a QTL linked to significantly increased fruit firmness in fruit from a cultivated tomato plant as described above compared to a control tomato plant comprising the steps of a) crossing a donor tomato plant with a recipient tomato plant to provide offspring plants, b) quantitatively determining the firmness in the fruit of said offspring plants c) establishing a genetic linkage map that links the observed increased fruit firmness to the presence of at least one DNA marker from said donor plant in said offspring plants and d) assigning to a QTL the DNA markers on said map that are linked to significantly increased fruit firmness.

Preferably said donor plant has fruit with a significantly increased fruit firmness compared to said recipient plant.

Preferably, the donor plant is S. pennellii and the recipient plant is S. lycopersicum. The fruit firmness range in the offspring plants is 1.2 to 2 times greater, or alternatively 1.2 to 1.5 times greater, than that of fruit produced from a control tomato plant at the harvesting stage.

Preferably, the harvesting stage is the mature green stage. Preferably the at least one DNA marker is selected from NT3853, NT3907, TG14, HOX7A, CT277, HB2600, TG353, Lm0127, Lm1650, LE5100 and LE5200. Preferably said QTL is one or more of a) QTL1 linked to at least one of the DNA markers NT3853, NT3907 and TG14; or b) QTL2 linked to at least one of the DNA markers HOX7A and CT277; c) QTL3 linked to at least one of the DNA markers HB2600, TG353; d) QTL4 linked to at least one of the DNA markers Lm0127 and Lm1650; or e) QTL5 linked to at least one of the DNA markers LE5100 and LE5200.

In one embodiment, said QTL is QTL1 linked to at least one of the DNA markers NT3853, NT3907 and TG14; which is present only in the inner pericarp.

There is also provided a QTL responsible for increased fruit firmness in fruit of a cultivated tomato plant detected by a method as herein described.

In one embodiment, said QTL is located on the long arm of chromosome 2.

In one embodiment there is provided a QTL as herein described linked to at least one DNA marker selected from the group consisting of NT3853, NT3907, TG14, HOX7A, CT277, HB2600, TG353, Lm0127, Lm1650, LE5100 and LE5200.

In one embodiment there is provided a QTL as herein described wherein said QTL is one or more of a) QTL1 linked to at least one of the DNA markers NT3853, NT3907 and TG14; b) QTL2 linked to at least one of the DNA markers HOX7A and CT277; c) QTL3 linked to at least one of the DNA markers HB2600, TG353; d) QTL4 linked to at least one of the DNA markers Lm0127 and Lm1650; or e) QTL5 linked to at least one of the DNA markers LE5100 and LE5200.

In one embodiment there is provided a QTL as herein described wherein said QTL is QTL1 linked to at least one of the DNA markers NT3853, NT3907 and TG14; which is present only in the inner pericarp.

There is also provided an isolated DNA sample obtained from a tomato plant comprising a QTL as herein described.

There is also provided a method of producing a tomato plant which provides fruit with increased fruit firmness as herein described.

There is also provided a method of producing an offspring cultivated tomato plant which provides fruit with increased fruit firmness comprising the steps of performing a method for detecting a QTL linked to increased fruit firmness, and transferring a nucleic acid comprising at least one QTL thus detected, from a donor tomato plant to a recipient tomato plant, wherein said increased fruit firmness is measured in fruit from an offspring cultivated tomato plant compared to fruit from a control tomato plant. The transfer of nucleic acid can be performed by any of several methods known in the art e.g. transformation, by protoplast fusion, by a doubled haploid technique or by embryo rescue.

Preferably, the fruit firmness range in the offspring tomato plant is greater than fruit from a control tomato plant at the mature green stage, or alternatively the breaker plus 7 days stage. The fruit firmness range could be 1.2 to 2 times greater or, alternatively, 1.2 to 1.5 times greater. Preferably, the donor plant is S. pennellii and the recipient plant is S. lycopersicum. Preferably, said QTL is one or more of a) QTL1 linked to at least one of the DNA markers NT3853, NT3907 and TG14; or b) QTL2 linked to at least one of the DNA markers HOX7A and CT277; or c) QTL3 linked to at least one of the DNA markers HB2600, TG353; or d) QTL4 linked to at least one of the DNA markers Lm0127 and Lm1650; or e) QTL5 linked to at least one of the DNA markers LE5100 and LE5200.

In one embodiment said QTL is QTL1 linked to at least one of the DNA markers NT3853, NT3907 and TG14; which is present only in the inner pericarp.

There is also provided a tomato plant, or part thereof, obtainable by a method as described herein.

There is also provided a cultivated tomato plant comprising a QTL responsible for increased fruit firmness as described herein.

There is also provided a hybrid tomato plant, or part thereof, obtainable by crossing a tomato plant as described herein with a tomato plant that exhibits commercially desirable characteristics.

There is also provided tomato seed produced by growing a tomato plant as described herein.

There is also provided tomato seed produced by crossing a tomato plant as described herein with a plant having desirable phenotypic traits to obtain a plant that has significantly increased fruit firmness compared to a control plant.

There is also provided the use of a QTL as described herein for the production of a tomato plant having increased fruit firmness compared to a control plant.

There is also provided the use of a tomato plant for expanding the harvesting slot of tomato fruit and/or for use in the fresh cut market or for food processing.

There is also provided processed food made from a tomato plant comprising the at least one QTL as described herein.

BRIEF DESCRIPTION OF THE DRAWINGS

FIG. 3 Genotyping of randomly selected lines of (Panel A) IL 2-3 F2 and (Panel B) IL 2-4 F3 to show distribution of recombination events with respect to Syngenta SSR and published RFLP and PCR-based markers. Key: A=M82; B=S. pennellii; H=heterozygote; *=missing data. The SSR markers are shown in the left hand column. The selected lines are shown on the top row.

DETAILED DESCRIPTION OF THE INVENTION

Definitions

Figure 1:
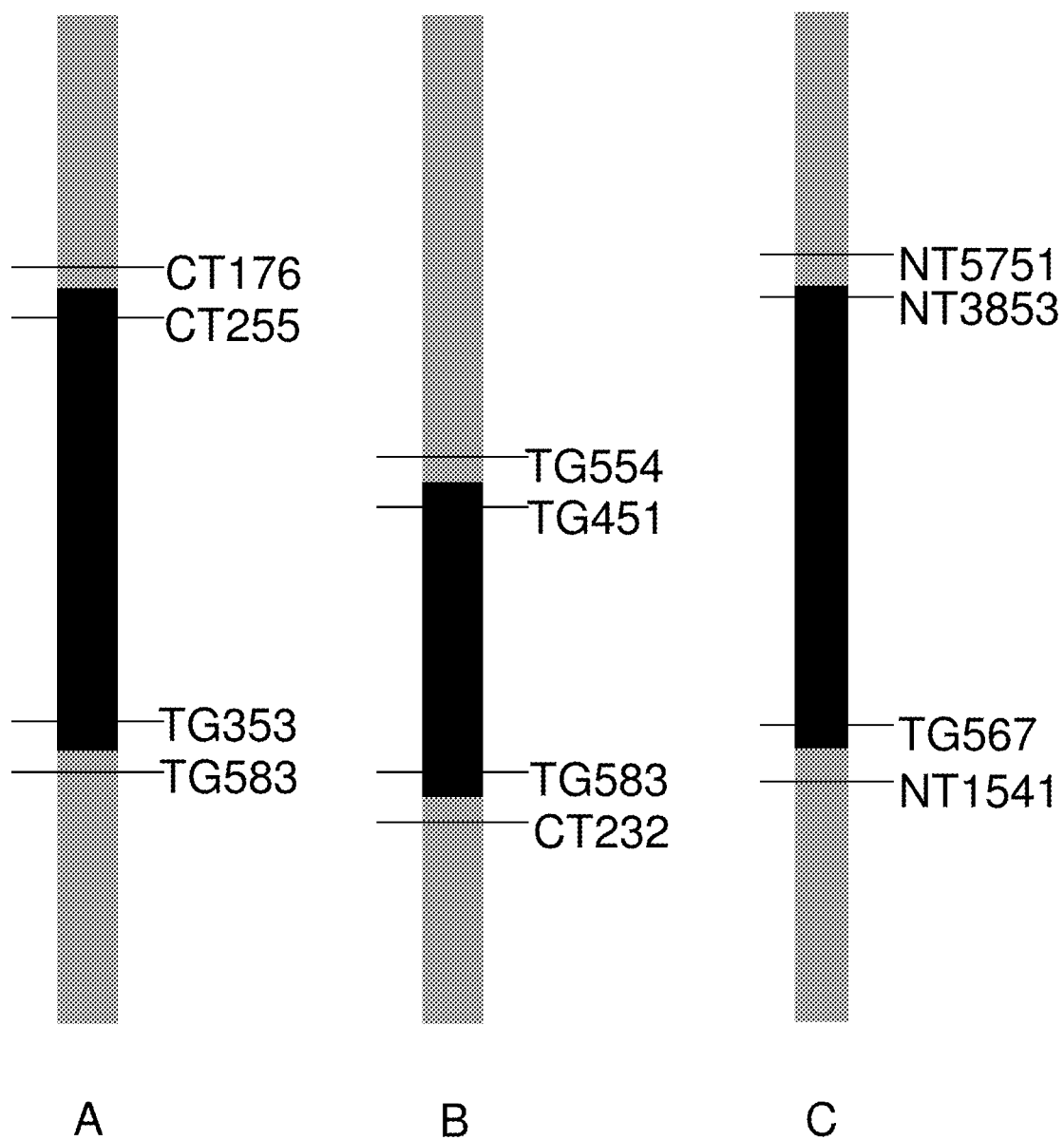
FIG. 1 Representation of (A) IL2-3 (B) IL2-4 and (C) QTL-NIL 301 introgressions. Proximal and distal markers are used to delimit introgressed regions (shown in black) from M82 regions (shown in grey).

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

An "allele" is understood within the scope of the invention to refer to alternative or variant forms of various genetic units identical or linked to different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic element typically occupy corresponding loci on a pair of homologous chromosomes.

An allele linked to a quantitative trait may comprise alternative or variant forms of various genetic units including those that are identical or linked to a single gene or multiple genes or their products or even a gene disrupting or controlled by a genetic factor contributing to the phenotype represented by said QTL.

As used herein, the term "backcross", and grammatical variants thereof, refers to a process in which a breeder crosses a hybrid progeny back to one of the parents, for example, a first generation hybrid F1 with one of the parental genotypes of the F1 hybrid. In some embodiments, a backcross is performed repeatedly, with a progeny individual of one backcross being itself backcrossed to the same parental genotype.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

For the purpose of the present invention, the term "co-segregation" refers to the fact that the allele for the trait and the allele(s) for the markers) tend to be transmitted together because they are physically close together on the same chromosome (reduced recombination between them because of their physical proximity) resulting in a non-random association of their alleles. "Co-segregation" also refers to the presence of two or more traits within a single plant of which at least one is known to be genetic and which cannot be readily explained by chance.

A "cultivated tomato plant" is understood within the scope of the invention to refer to a plant that is no longer in the natural state but has been developed by human care and for human use and/or consumption. "Cultivated tomato plants" are further understood to exclude those wild-type species which comprise the trait being subject of this invention as a natural trait and/or part of their natural genetics. Cultivated tomato plants also typically display resistance to Tobacco mosaic virus, whereas wild-type species do not.

There are 2 major types of tomato growth: determinate and indeterminate. Determinate growth produces "bush" tomatoes and which are bred for compactness. The entire plant stops growing once the terminal fruit ripens, the remainder of the fruit all ripen simultaneously, and then the plant dies. Indeterminate growth produces tomatoes that can grow up to 10 feet in height (so-called "vining" tomatoes) and will only stop growing when killed by frost. Their fruit ripen rotationally. In a typical plant, all growth arises from the reiteration of modular sympodial units that each produce three leaves and a multiflowered inflorescence. All field-grown varieties of tomato, including M82, are determinate plants whose shoots produce an average of six sympodial units, each harboring a single inflorescence, within which leaf number gradually decreases before a precocious termination of growth. In general, determinate tomatoes are suitable for open field production. Semideterminate and indeterminate "cultivated" varieties are suitable for staked cultivation in the open field or protected nets and for glasshouse cultivation. For the purposes of the present invention, the *S. pennellii* introgression lines e.g. IL2-3 and IL2-4 are not regarded as cultivated lines, whereas parental line M82 and recombinant lines e.g. QTL-NIL 301 are regarded as cultivated lines.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating anymore (stable).

As used herein, the term "gene" refers to a hereditary unit including a sequence of DNA that occupies a specific location on a chromosome and that contains the genetic instruction for a particular characteristic or trait in an organism.

As used herein, the term "genetic architecture at the QTL" refers to a genomic region which is statistically correlated to the phenotypic trait of interest and represents the underlying genetic basis of the phenotypic trait of interest.

"Genetic engineering", "transformation" and "genetic modification" are all used herein as synonyms for the transfer of isolated and cloned genes into the DNA, usually the chromosomal DNA or genome, of another organism.

As used herein, the phrases "genetic marker", "DNA marker" or "molecular marker" are interchangeable and refer to a feature of an individual's genome (e.g. a nucleotide or a polynucleotide sequence that is present in an individual's genome) that is linked to one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs) restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs) among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes. A genetic or molecular marker can be physically located in a position on a chromosome that is distal or proximal to the genetic loci with which it is linked (i.e. is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a very low rate of recombination between the genetic marker and the locus of interest, the presently disclosed subject matter can also employ genetic markers that are physically within the boundaries of a genetic locus (e.g. inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g. a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

"Heterozygous" is understood within the scope of the invention to refer to unlike alleles at one or more corresponding loci on homologous chromosomes.

"Homozygous" is understood within the scope of the invention to refer to like alleles at one or more corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C. particularly between 45° C. and 65° C., but especially at 59° C. (regarding the definition of SSPE, SSC and Denhardts solution see Sambrook et al. (2001)). High stringency hybridization conditions as for instance described in Sambrook et al. (2001), are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the terms "introgression", "introgressed" and "introgressing" refer to the process whereby genes, a QTL or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "linkage", and grammatical variants thereof, refers to the tendency of alleles at different loci on the same chromosome to segregate together more often than would be expected by chance if their transmission were independent, in some embodiments as a consequence of their physical proximity. Linkage is measured by percent recombination between loci (centimorgan, cM).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e. less than the entirety) of a given chromosome.

"Locus" is understood within the scope of the invention to refer to a region on a chromosome, which comprises a gene or any other genetic element or factor contributing to a trait.

As used herein, the term "marker allele" refers to an alternative or variant form of a genetic unit as defined herein above, when used as a marker to locate genetic loci containing alleles on a chromosome that contribute to variability of phenotypic traits.

"Marker-based selection" is understood within the scope of the invention to refer to e.g. the use of genetic markers to detect one or more nucleic acids from the plant, where the nucleic acid is linked to a desired trait to identify plants that carry genes, QTLs or haplotypes for desirable (or undesirable) traits, so that those plants can be used (or avoided) in a selective breeding program.

"Marker assisted selection" refers to the process of selecting a desired trait or desired traits in a cultivated plant or cultivated plants by detecting one or more nucleic acids from the cultivated plant, where the nucleic acid is linked to the desired trait.

As used herein, "marker locus" refers to a region on a chromosome, which comprises a nucleotide or a polynucleotide sequence that is present in an individual's genome and that is linked to one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as a probe.

"Microsatellite or SSRs (Simple sequence repeats) marker" is understood within the scope of the invention to refer to a type of genetic marker that consists of numerous repeats of short sequences of DNA bases, which are found at loci throughout the plant's genome and have a likelihood of being highly polymorphic.

"Nucleic acid" or "oligonucleotide" or "polynucleotide" or grammatical equivalents thereof used herein means at least two nucleotides covalently linked together. Oligonucleotides are typically from about 7, 8, 9, 10, 12, 15, 1820 25, 30, 40, 50 or up to about 100 nucleotides in length. Nucleic acids and polynucleotides are polymers of any length, including longer lengths, e.g. 200, 300, 500, 1000, 2000, 3000, 5000, 7000, 10000, etc. A nucleic acid of the present invention will generally contain phosphodiester bonds, although in some cases, nucleic acid analogs are included that may have alternate backbones comprising, e.g. phosphoramidate, phosphorothioate, phosphorodithioate, or O-methylphosphoroamidite linkages (see Eckstein, 1991), and peptide nucleic acid backbones and linkages. Mixtures of naturally occurring nucleic acids and analogs can be used. Particularly preferred analogs for oligonucleotides are peptide nucleic acids (PNA).

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1 s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

As used herein, the expression "phenotype" or "phenotypic trait" refers to the appearance or other detectable characteristic of an individual, resulting from the interaction of its genome, proteome and/or metabolome with the environment.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calii, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Polymorphism" is understood within the scope of the invention to refer to the presence in a population of two or more different forms of a gene, genetic marker, or inherited trait or a gene product obtainable, for example, through alternative splicing, DNA methylation, etc.

As used herein, the term "population" means a genetically heterogeneous collection of plants sharing a common genetic derivation.

"Probe" as used herein refers to a group of atoms or molecules which is capable of recognizing and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

The term "QTL" is used herein in its art-recognised meaning. The term "QTL linked to increased fruit firmness in tomato" as well as the shorter term "QTL for increased fruit firmness" refer to a region located on a particular chromosome of tomato that is linked to at least one gene that is responsible for increased fruit firmness or at least a regulatory region, i.e. a region of a chromosome that controls the expression of one or more genes involved in increased fruit firmness. A QTL may for instance comprise one or more genes, the products of which confer increased fruit firmness. Alternatively, a QTL may for instance comprise regulatory genes or sequences, the products of which influence the expression of genes on other loci in the genome of the plant thereby conferring the increased fruit firmness. The QTLs of the present invention may be defined by indicating their genetic location in the genome of the respective wild tomato accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

As used herein, the terms "QTL1", "QTL2", "QTL3", "QTL4" and "QTL5" refer to the genomic regions linked to increased tomato firmness as defined by the markers NT3853, NT3907 and TG14; HOX7A and CT277; HB2600, and TG353; Lm0127 and Lm1650; and LE5100 and LE5200 respectively. For the purposes of the instant disclosure, these markers are said to be present on *S. pennellii* chromosome 2.

The term "quantitatively determining" is defined herein as establishing or assessing in a manner involving measurement, in particular the measurement of aspects measurable in terms of amounts and number. Determinations in degrees of severity and indications of greater, more, less, or equal or of increasing or decreasing magnitude, are not comprised in the present term "quantitatively determining", which term ultimately implies the presence of objective counting mechanism for determining absolute values.

The term "recipient tomato plant" is used herein to indicate a tomato plant that is to receive DNA obtained from a donor tomato plant that comprises a QTL for increased fruit firmness. Said "recipient tomato plant" may or may not already comprise one or more QTLs for fruit firmness, in which case the term indicates a plant that is to receive an additional QTL.

The term "natural genetic background" is used herein to indicate the original genetic background of a QTL. Such a background may for instance be the genome of a wild accession of tomato. For instance, the QTLs of the present invention were found at specific locations on chromosome 2 of S. pennellii. As an example, S. pennellii represents the natural genetic background of QTLs 1, 2, 3, 4 and 5 on chromosome 2 of S. pennellii. Conversely, a method that involves the transfer of DNA comprising these QTLs, or a fruit firmness-conferring part thereof, from Chromosome 2 of S. pennellii to the same position on chromosome 2 of another tomato species, preferably cultivated S. lycopersicum, will result in these QTLs, or said fruit firmness-conferring part thereof, not being in its natural genetic background.

In this application, a "recombination event" is understood to mean a meiotic crossing-over.

"Sequence Homology" or "sequence Identity" is used herein interchangeably. The terms "identical" or "percent identity" in the context of two or more nucleic acid or protein sequences, refer to two or more sequences or sub-sequences that are the same or have a specified percentage of amino acid residues or nucleotides that are the same, when compared and aligned for maximum correspondence, as measured using one of the following sequence comparison algorithms or by visual inspection, if two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman (1981) in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so called optional parameters are preferably left at their preset ("default") values. The deviations appearing in the comparison between a given sequence and the above described sequences of the invention may be caused for instance by addition, deletion, substitution, insertion or recombination. Such a sequence comparison can preferably also be carried out with the program fasta20u66" (version 2.0u65, September 1998 by William R. Pearson and the University of Virginia; see also W. R. Pearson (1990), appended examples and at workbench.sdsc.edu/). For this purpose, the "default" parameter settings may be used.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g. total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

As used herein, the phrases "sexually crossed" and "sexual reproduction" in the context of the presently disclosed subject matter refers to the fusion of gametes to produce progeny (e.g. by fertilization, such as to produce seed by pollination in plants). A "sexual cross" or "cross-fertilization" is in some embodiments fertilization of one individual by another (e.g. cross-pollination in plants). The term "self ing" refers in some embodiments to the production of seed by self-fertilization or self-pollination i.e. pollen and ovule are from the same plant.

A "single nucleotide polymorphism" (SNP) is a DNA sequence variation occurring when a single nucleotide A, C, G, T in the genome (or other shared sequences as mitochondrial DNA) differs between a set (paired) chromosomes of an individual or differs between members of a species.

The term "standard greenhouse conditions" and "standard conditions" refer to the conditions of light, humidity, temperature, etc whereupon plants are grown or incubated, for instance for the purpose of phenotypic characterization of disease fruit firmness, as being standard. Growth conditions can for example be a photoperiod of 16 h (photosynthetic photon flux (PPF) 50 to 1000 µmol nv2 s1), preferably a regime of 8 hours dark, an air temperature of about 20° C. during the day and 18° C. at night, a water vapour pressure deficit of about 4.4 g m3 corresponding to a relative humidity (RH) of about 60%-85%, at atmospheric oxygen concentration and at atmospheric air pressure (generally 1008 hPa). Water and nutrients may be given drop wise near the stem, or in the form of spray or mist.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, New York. Generally, highly stringent hybridization and wash conditions are selected to be about 5° C. lower than the thermal melting point (Tm) for the specific sequence at a defined ionic strength and pH. Typically, under "stringent conditions" a probe will hybridize to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2 times SSC wash at 65° C. for 15 minutes (see Sambrook, infra, for a description of SSC buffer). Often, a high stringency wash is preceded by a low stringency wash to remove background probe signal. An example medium stringency wash for a duplex of for example more than 100 nucleotides, is 1 times SSC at 45° C. for 15 minutes. An example low stringency wash for a duplex of, e.g. more than 100 nucleotides, is 4-6 times SSC at 40° C. for 15 minutes. For short probes (e.g. about 10 to 50 nucleotides), stringent conditions typically involve salt concentrations of less than about 1.0M Na ion concentration, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs for example when a copy of a nucleic acid is created using the maximum codon degeneracy permitted by the genetic code.

As used herein, the term "tomato" means any plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium*, or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into *S.* 'N *peruvianum*' and *S.* 'Callejon de Huayles', *S. peruvianum*, and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense*, and *L. pimpinellifolium* may become *S. pimpinellifolium* (Knapp (2005)).

"Trait" is understood within the scope of the invention to refer to a characteristic or phenotype, for example increased fruit firmness. A trait may be inherited in a dominant or recessive manner, or may be monogenic or polygenic.

"Monogenic" is understood within the scope of the invention to refer to being determined by a single locus.

"Polygenic" is understood within the scope of the invention to refer to being determined by more than one locus.

"Dominant" is understood within the scope of the invention to refer to an allele which determines the phenotype when present in the heterozygous or homozygous state.

A "recessive" allele is only displayed when present in the homozygous state.

"Isogenic" is understood within the scope of the invention to refer to cultivated plants which are genetically identical, except that they may differ by the presence or absence of a heterologous DNA sequence.

"Harvesting stage" is understood within the scope of the invention to mean the date of harvesting ie the date the tomato fruit is removed from the plant.

"Immature Green stage" is defined as when the fruits are unripe and still growing in size. This stage is understood to be the first stage in the ripening process.

"Mature green stage" is defined as when the fruit is fully expanded mature, but unripe and follows the "immature green stage" in the ripening process. Mature green tomatoes have a white to yellow "star" on the blossom end. Traditional tomatoes harvested at the mature green stage are best suited for the commercial fresh market because they tolerate rough handling better than the riper stages and hold their shape the longest in storage, shipping, and on the supermarket shelf; however they somehow lack full aroma and taste.

"Breaker stage" is defined as first sign of red colour in the fruit, typically it occurs within 24 hours of the mature green stage. Tomatoes that are harvested at the "Breaker stage" usually have better flavor and taste but they have reduced firmness and are slightly less suitable for handling, packaging and transportation than tomatoes at the mature green stage.

"Red ripe stage" is defined as when the fruits are fully red, with no sign of green colour. These fruits have reached their optimum in taste and flavor but they cannot be transported because of their lack of firmness and they do not tolerate much handling.

"Genetic element" and "genetic element, or part thereof" are understood within the scope of the invention to mean a QTL or part thereof (in particular, a gene residing on the chromosome under the QTL) that is capable of contributing to the firmness of the fruits of the plant by influencing expression of the firmness trait at the level of the DNA itself, at the level of translation, transcription and/or activation of a final polypeptide product, i.e., to regulate metabolism in tomato fruit flesh leading to the phenotypic expression of the genotype.

"Inner pericarp" and "outer pericarp" are understood within the scope of the invention to mean fruit tissue where the outer pericarp is the layer (approximately 2 mm) immediately below the outer epidermis and above the vascular tissue layer. The inner pericarp is from 3 mm up to 10 mm below the vascular layer and before the inner epidermis.

"Commercially desirable characteristics" are understood within the scope of the invention to include but not be limited to superior fruit quality, disease resistance, insect resistance, uniform shape and size "Harvesting slot" is understood within the scope of the invention to mean the period of time from the harvesting stage until when the fruit is too ripe to be harvested for the purposes of commercial sale. Typically, the harvesting slot starts at mature green stage and continues until the breaker stage plus two to five days, depending on the cultivar and environmental conditions.

"donor tomato plant" is understood within the scope of the invention to mean the tomato plant which provides at least one genetic element linked to significantly increased fruit firmness.

"linked to" and "characterized by" or "associated with" at least one of the DNA markers of the present invention is understood within the scope of the invention to mean a DNA sequence that is genetically linked, to the genetic element responsible for the increased fruit firmness trait and wherein a specific marker sequence is linked to a particular allele of that gene. When two markers/sequences are said to be genetically linked, the recombination frequency between the two markers/sequences are low and it can be expected that both these markers/sequences are inherited jointly. For the population of plants described herein, markers named as linked to the QTLs are a distance of 1 cM or less away. Markers that are 1 cM distance apart from each other have a 1% chance of being separated from each other due to a recombination event in a single generation.

"fruit firmness conferring parts of QTLs" is understood within the scope of the invention to mean the genetic element(s) or part(s) thereof responsible for increased tomato fruit firmness as determined by mechanical measurement as described in the examples.

"Increase in fruit firmness" and "increased fruit firmness" are understood within the scope of the invention to mean tomato fruit which has an increased maximum load value (for example as described in Example 1), statistically significant at P<0.05 or P<0.01 compared to fruit from a control plant.

Maximum load is defined as the value that represents the greatest load (in Newtons (N)) required to cause failure of tissue integrity.

"control tomato plant" is understood within the scope of the invention to mean a tomato plant that has the same genetic background as the cultivated tomato plant of the present invention wherein the control plant does not have any of the at least one genetic elements—or part thereof—of the present invention linked to increased fruit firmness. In particular a control tomato plant is a tomato plant belonging to the same plant variety and does not comprise any of the at least one genetic element, or part thereof. The control tomato plant is grown for the same length of time and under the same conditions as the cultivated tomato plant of the present invention. Plant variety is herein understood according to definition of UPOV. Thus a control tomato plant may be an inbred line or a hybrid provided that they have the same genetic background as the tomato plant of the present invention except the control plant does not have any of the at least one genetic element—or part thereof—of the present invention linked to increased fruit firmness.

"anthesis" is understood within the scope of the invention to mean the period during which the flower is fully open and pollen is released.

"Processed food" is understood within the scope of the invention to mean food which has been altered from its natural state. Methods used for processing food include but are not limited to canning, freezing, refrigeration, dehydration and aseptic processing.

"Fresh cut market" is understood within the scope of the invention to mean vegetables on the market which have been minimally processed.

"first true leaf" is understood within the scope of the invention to mean when the first leaf emerges after emergence of the seed leaves or cotyledons.

Plant Breeding

The purpose of breeding programs in agriculture and horticulture is to enhance the performance of plants by improving their genetic composition. In essence, this improvement accrues by increasing the frequency of the most favorable alleles for the genes influencing the performance characteristics of interest.

Wild plant lines provide a rich resource of genetic and phenotypic variation. Traditionally, agricultural or horticultural practice makes use of this variation by selecting a wild plant line or its offspring for having desired genotypic or potential phenotypic properties, crossing it with a line having additional desired genotypic or potential phenotypic properties and selecting from among the offspring plants those that exhibit the desired genotypic or potential phenotypic properties (or an increased frequency thereof).

A growing understanding and utilization of the laws of Mendelian inheritance in combination with molecular genetic tools have in the past century facilitated this selection process. For example, methods for selecting plants for having desired genotypic or potential phenotypic properties have become available based on testing the plant for the presence of a quantitative trait locus (QTL); i.e. for the presence of a genetic element containing alleles linked to the expression of a continuously distributed (quantitative) phenotypic trait. Usually a QTL is characterized by one or more markers that statistically associate to the quantitative variation in the phenotypic trait and is essentially synonymous to a gene. QTL mapping allows for the identification of genetic element(s) affecting the expression of a trait of interest. In plant breeding, it allows for marker-assisted selection (MAS); i.e. the selection of plants having favorable alleles by detecting in those plants the QTL-associated markers.

Knowledge of the inheritance of various traits would allow for the selection of lines homozygous for a QTL linked to increased fruit firmness. Use of the knowledge of the genetic origin and location of a desired trait in a breeding program can increase the accuracy of the predicted breeding outcome and can enhance the rate of selection compared to conventional breeding programs. For instance, the fact that the genetic basis of a desired trait is heritably linked to another trait can help to increase uniformity for those two traits among the offspring since a parent homozygous for the desired alleles will pass them to most if not all offspring, resulting in a reduced segregation in the offspring.

The presently disclosed subject matter provides for better models for marker-assisted selection (MAS). The presently disclosed subject matter relates to methods of plant breeding and to methods to select tomato plants, particularly cultivated tomato plants as breeder plants for use in breeding programs or cultivated tomato plants having desired genotypic or potential phenotypic properties, in particular those which produce tomato fruit with increased fruit firmness at the harvesting stage.

Accordingly, there is provided a tomato fruit with increased fruit firmness at the harvesting stage linked to at least one genetic element in the cultivated tomato plant producing said tomato, wherein said firmness is from between 1.2 to 2.0 times greater than that of fruit from a control tomato plant which does not have the said at least one genetic element.

The harvesting stage is preferably the mature green stage. Alternatively, the harvesting stage can be any chosen point in the development of the tomato fruit, which includes but is not limited to the immature green stage, rapid expansion stage, mature green stage, breaker stage or red ripe stage or 1, 2, 3, 4, 5, 6, 7, 8, 9 or 10 days after any of these stages. In one embodiment, the harvesting stage is the breaker stage plus 7 days.

In a specific embodiment there is provided a tomato fruit providing increased fruit firmness at the mature green stage linked to at least one genetic element in the cultivated tomato plant producing said tomato, wherein said firmness is from between 1.2 to 2.0 times greater than that of fruit from a control tomato plant which does not have the said at least one genetic element. In another embodiment, said firmness is 1.2 to 1.5 times greater than that of fruit from a control tomato plant which does not have the said at least one genetic element.

In a specific embodiment, there is provided a tomato fruit providing increased fruit firmness at the breaker stage plus 7 days caused by at least one genetic element in the cultivated tomato plant producing said tomato, wherein said firmness is from between 1.2 to 2.0 times greater than that of fruit from a control tomato plant which does not have the said at least one genetic element. In another embodiment, said firmness is 1.2 to 1.5 times greater than that of fruit from a control tomato plant which does not have the said at least one genetic element.

Fruit firmness is preferably measured in the outer pericarp and inner pericarp of the cultivated tomato plant. Alternatively, fruit firmness can be measured in the inner pericarp only. Preferably, fruit firmness is measured by mechanical means. Typically, a Lloyd LRX machine is used as described in the Example section. Such measurements represent a sensitive mechanical measure of fruit firmness that correlates very well with conventional penetrometer assays, but gives substantially more sensitive and reproducible results. In addition these measurements also correlate well with organoleptic/sensory descriptions of fruit firmness (King et al, 2001). However, alternative methods for measuring fruit firmness which are known to the skilled person may also be employed such as those described in Causse et al (2002), the full contents of which are incorporated herein in their entirety.

Preferably the control tomato plant is M82 with deposit number NCIMB 41661.

Alternatively, the control plant can be any tomato plant which differs from its offspring essentially due to the absence of at least one genetic element, or part thereof, responsible for increased fruit firmness in the cultivated tomato plant. The control tomato plant may be selected from any plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium,* or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into *S. 'N peruvianum'* and *S. 'Callejon de Huayles', S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium* (Knapp (2005))

Preferably the genetic element(s) responsible for significantly increased fruit firmness of the present invention is present on chromosome 2 of tomato. Preferably, the at least one genetic element is present on chromosome 2 of *S. pennellii*. More preferably, the at least one genetic element is present on the long arm of chromosome 2 of *S. pennellii*. Most preferably, the at least one genetic element is present on the long arm of chromosome 2 of *S. pennellii* and is any one, two, three, four or all of QTLs 1 to 5.

In a further aspect, there is provided a cultivated tomato plant which produces tomato fruit as described herein wherein said plant comprises at least one genetic element which is characterized by at least one DNA marker selected from the group consisting of NT3853, NT3907, TG14, HOX7A, CT277, HB2600, TG353, Lm0127, Lm1650, LE5100 and LE5200.

In a further aspect, there is provided a cultivated tomato plant which produces tomato fruit wherein said plant comprises at least one genetic element which is complementary to the corresponding genetic element in *S. pennellii* lines IL2-3 and/or IL2-4 deposited under accession numbers LA4038 and LA4039, respectively, wherein said genetic element in *S. pennellii* IL2-3 and/or IL2-4 can be characterized by at least one DNA marker selected from the group consisting of NT3853, NT3907, TG14, HOX7A, CT277, HB2600, TG353, Lm0127, Lm1650, LE5100 and LE5200.

There is also provided a cultivated tomato plant which produces tomato fruit with increased fruit firmness compared to fruit from a control tomato plant wherein said cultivated tomato plant has one genetic element which is a QTL selected from a) QTL1 linked to at least one of the DNA markers NT3853, NT3907 and TG14; orb) QTL2 linked to at least one of the DNA markers HOX7A and CT277; or c) QTL3 linked to at least one of the DNA markers HB2600, TG353; or d) QTL4 linked to at least one of the DNA markers Lm0127 and Lm1650; or e) QTL5 linked to at least one of the DNA markers LE5100 and LE5200.

There is also provided a cultivated tomato plant which produces tomato fruit with increased fruit firmness compared to fruit from a control tomato plant wherein said cultivated tomato plant comprises at least one genetic element, wherein the genetic elements are QTL1 linked to at least one of the DNA markers NT3853, NT3907 and TG14; and QTL2 linked to at least one of the DNA markers HOX7A and CT277.

There is also provided a cultivated tomato plant produces tomato fruit with increased fruit firmness compared to a control tomato plant wherein said cultivated tomato plant comprises at least one genetic element, wherein the genetic elements are QTL1 linked to at least one of the DNA markers NT3853, NT3907 and TG14; and QTL3 linked to at least one of the DNA markers HB2600, and TG353.

There is also provided a cultivated tomato plant produces tomato fruit with increased fruit firmness compared to a control tomato plant wherein said cultivated tomato plant comprises at least one genetic element, wherein the genetic elements are QTL1 linked to at least one of the DNA markers NT3853, NT3907 and TG14; and QTL4 linked to at least one of the DNA markers Lm0127 and Lm1650.

There is also provided a cultivated tomato plant produces tomato fruit with increased fruit firmness compared to a control tomato plant wherein said cultivated tomato plant comprises at least one genetic element, wherein the genetic elements are QTL1 linked to at least one of the DNA markers NT3853, NT3907 and TG14; and QTL5 linked to at least one of the DNA markers LE5100 and LE5200

There is also provided a cultivated tomato plant produces tomato fruit with increased fruit firmness compared to a control tomato plant wherein said cultivated tomato plant comprises at least one genetic element, wherein the genetic elements are QTL2 linked to at least one of the DNA markers HOX7A and CT277; and QTL3 linked to at least one of the DNA markers HB2600, and TG353.

There is also provided a cultivated tomato plant produces tomato fruit with increased fruit firmness compared to a control tomato plant wherein said cultivated tomato plant comprises at least one genetic element, wherein the genetic elements are QTL2 linked to at least one of the DNA markers HOX7A and CT277; and QTL4 linked to at least one of the DNA markers Lm0127 and Lm1650.

There is also provided a cultivated tomato plant produces tomato fruit with increased fruit firmness compared to a control tomato plant wherein said cultivated tomato plant comprises at least one genetic element, wherein the genetic elements are QTL2 linked to at least one of the DNA markers HOX7A and CT277; and QTL5 linked to at least one of the DNA markers LE5100 and LE5200.

There is also provided a cultivated tomato plant produces tomato fruit with increased fruit firmness compared to a control tomato plant wherein said cultivated tomato plant comprises at least one genetic element, wherein the genetic elements are QTL3 linked to at least one of the DNA markers HB2600 and TG353; and QTL4 linked to at least one of the DNA markers Lm0127 and Lm1650.

There is also provided a cultivated tomato plant produces tomato fruit with increased fruit firmness compared to a control tomato plant wherein said cultivated tomato plant comprises at least one genetic element, wherein the genetic elements are QTL3 linked to at least one of the DNA markers HB2600 and TG353; and QTL5 linked to at least one of the DNA markers LE5100 and LE5200.

There is also provided a cultivated tomato plant produces tomato fruit with increased fruit firmness compared to a control tomato plant wherein said cultivated tomato plant comprises at least one genetic element, wherein the genetic elements are QTL4 linked to at least one of the DNA markers Lm0127 and Lm1650; and QTL5 linked to at least one of the DNA markers LE5100 and LE5200.

There is also provided a cultivated tomato plant produces tomato fruit with increased fruit firmness compared to a control tomato plant wherein said cultivated tomato plant comprises at least one genetic element, wherein the genetic elements are QTL1 linked to at least one of the DNA markers NT3853, NT3907 and TG14; and QTL2 linked to at least one of the DNA markers HOX7A and CT277; and QTL3 linked to at least one of the DNA markers HB2600, TG353; and QTL4 linked to at least one of the DNA markers Lm0127 and Lm1650; and QTL5 linked to at least one of the DNA markers LE5100 and LE5200.

There is also provided a cultivated tomato plant produces tomato fruit with increased fruit firmness compared to a control tomato plant wherein said cultivated tomato plant comprises at least one genetic element, wherein the genetic element is QTL1 linked to at least one of the DNA markers NT3853, NT3907 and TG14; which is present only in the inner pericarp.

In a further aspect of the invention, there is provided a cultivated tomato plant as herein described wherein said plant is an inbred, a dihaploid or a hybrid. In a specific embodiment, the cultivated tomato plant is male sterile.

In a further aspect of the invention, there is provided tomato seed which produces a cultivated tomato plant as herein described.

In a further aspect of the invention, there is provided a plant part of a cultivated tomato plant as herein described.

In a further aspect, there is provided plant material obtainable from a plant part of a cultivated tomato plant as herein described.

Identification of QTLs Linked to Increased Fruit Firmness in Tomato

The presently disclosed subject matter also provides methods for selecting a cultivated tomato plant with fruit having increased firmness compared to fruit from a control tomato plant. Such methods comprise detecting in the cultivated tomato plant the presence of one or more of QTLs 1 to 5 as defined herein. In general, the methods comprise providing a sample of genomic DNA from a tomato plant; and (b) detecting in the sample of genomic DNA at least one molecular marker linked to a QTL selected from the group consisting of QTLs 1 to 5. In some embodiments, the detection step may comprise detecting at least one molecular marker from the group, the at least one molecular markers detecting at least one of QTLs 1 to 5. The providing of a sample of genomic DNA from a tomato plant can be performed by standard DNA isolation methods well known in the art.

In some embodiments, the detecting of a molecular marker (step (b)) may comprise the use of a nucleic acid probe having a base sequence that is substantially complementary to the nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. The detecting of a molecular marker can also comprise performing a nucleic acid amplification reaction on the genomic DNA to detect one or more QTLs. This can be done by performing a PCR reaction using a set of marker-specific primers. In some embodiments, the detecting can comprise the use of at least one set of primers defining one or more markers linked to one or more of QTLS 1 to 5, or a set of primers which specifically hybridize under stringent conditions with nucleic acid sequences of one or more markers linked to one or more of QTLS 1 to 5.

The presently disclosed methods can also include detecting an amplified DNA fragment linked to the presence of a QTL. In some embodiments, the amplified fragment linked to presence of a QTL has a predicted length or nucleic acid sequence, and detecting an amplified DNA fragment having the predicted length or the predicted nucleic acid sequence is performed such that the amplified DNA fragment has a length that corresponds (plus or minus a few bases; e.g. a length of one, two or three bases more or less) to the expected length as based on a similar reaction with the same primers with the DNA from the plant in which the marker was first detected or the nucleic acid sequence that corresponds (has a homology of in some embodiments more than 80%, in some embodiments more than 90%, in some embodiments more than 95%, in some embodiments more than 97%, and in some embodiments more than 99%) to the expected sequence as based on the sequence of the marker linked to that QTL in the plant in which the marker was first detected. One of ordinary skill in the art would appreciate that markers that are absent in plants providing fruit with increased fruit firmness, while they were present in the control parent(s) (so-called trans-markers), can also be useful in assays for detecting increased fruit firmness among offspring plants, although testing the absence of a marker to detect the presence of a specific trait is not optimal. The detecting of an amplified DNA fragment having the predicted length or the predicted nucleic acid sequence can be performed by any of a number of techniques, including but not limited to standard gel-electrophoresis techniques or by using automated DNA sequencers. These methods are well known to the skilled person.

Molecular Markers and QTLS

Molecular markers are used for the visualization of differences in nucleic acid sequences. This visualization can be due to DNA-DNA hybridization techniques after digestion with a restriction enzyme (RFLP) and/or due to techniques using the polymerase chain reaction (e.g. STS, SSR/microsatellites, AFLPs and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994.

The recombination frequencies of molecular markers on different chromosomes are generally 50%. Between molecular markers located on the same chromosome, the recombination frequency generally depends on the distance between the markers. A low recombination frequency corresponds to a low genetic distance between markers on a chromosome. Comparing all recombination frequencies results in the most logical order of the molecular markers on the chromosomes. This most logical order can be depicted in a linkage map (Paterson, 1996). A group of adjacent or contiguous markers on the linkage map that is linked to an increased level of fruit firmness can provide the position of a QTL linked to increased fruit firmness.

The markers identified herein can be used in various aspects of the presently disclosed subject matter. Aspects of the presently disclosed subject matter are not to be limited to the use of the markers identified herein, however. It is stressed that the aspects can also make use of markers not explicitly disclosed herein or even yet to be identified. Other than the genetic unit "gene", on which the phenotypic expression depends on a large number of factors that cannot be predicted, the genetic unit "QTL" denotes a region on the genome that is directly related to a phenotypic quantifiable trait.

The five QTLs identified herein are located on chromosome 2 of tomato and their locations can be characterized by a number of otherwise arbitrary markers. In the present investigations, microsatellite markers (e.g. SSRs) and single nucleotide polymorphisms (SNPs) were used, although restriction fragment length polymorphism (RFLP) markers, amplified fragment length polymorphism (AFLP) markers, insertion mutation markers, sequence-characterized amplified region (SCAR) markers, cleaved amplified polymorphic sequence (CAPS) markers or isozyme markers or combinations of these markers might also have been used.

In general, a QTL can span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace among a population of offspring plants those plants that have the genetic potential for exhibiting a particular phenotypic trait. By providing a non-limiting list of markers, the presently disclosed subject matter thus provides for the effective use of the presently disclosed QTLs in a breeding program.

In general, a marker is specific for a particular line of descent. Thus, a specific trait can be linked to a particular marker. The markers as disclosed herein not only indicate the location of the QTL, they also correlate with the presence of the specific phenotypic trait in a plant. It is noted that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e. one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL can be considered set. Thus, it is also possible to indicate the location of the QTL by other markers located within that specified region. It is further noted that the contiguous genomic markers can also be used to indicate the presence of the QTL (and thus of the phenotype) in an individual plant, which sometimes means that they can be used in marker-assisted selection (MAS) procedures. In principle, the number of potentially useful markers is limited but can be very large, and one of ordinary skill in the art can easily identify markers in addition to those specifically disclosed in the present application. Any marker that is linked to the QTL (e.g. falling within the physical boundaries of the genomic region spanned by the markers having established LOD scores above a certain threshold thereby indicating that no or very little recombination between the marker and the QTL occurs in crosses, as well as any marker in linkage disequilibrium to the QTL, as well as markers that represent the actual causal mutations within the QTL) can be used in MAS procedures. This means that the markers identified in the application as being linked with the QTLs, such as the markers NT3853, NT3907, TG14, HOX7A, CT277, HB2600, TG353, Lm0127, Lm1650, LE5100 and LE5200, are mere examples of markers suitable for use in MAS procedures. Moreover, when the QTL, or the specific trait-conferring part thereof, is introgressed into another genetic background (i.e. into the genome of another tomato or another plant species), then some markers might no longer be found in the offspring although the trait is present therein, indicating that such markers are outside the genomic region that represents the specific trait-conferring part of the QTL in the original parent line only and that the new genetic background has a different genomic organization. Such markers of which the absence indicates the successful introduction of the genetic element in the offspring are called "trans markers" (see above).

Upon the identification of a QTL, the QTL effect (i.e. for increased fruit firmness) can for instance be confirmed by assessing fruit firmness in progeny segregating for the QTLs under investigation. The assessment of the fruit firmness can suitably be performed by measuring fruit firmness as known in the art.

The markers provided by the presently disclosed subject matter can be used for detecting the presence of one or more increased fruit firmness alleles at QTLs of the presently disclosed subject matter in a tomato plant with increased fruit firmness, and can therefore be used in methods involving marker-assisted breeding and selection of tomato plants with increased fruit firmness. In some embodiments, detecting the presence of a QTL of the presently disclosed subject matter is performed with at least one of the markers for a QTL as defined herein. The presently disclosed subject matter therefore relates in another aspect to a method for detecting the presence of a QTL for increased fruit firmness, comprising detecting the presence of a nucleic acid sequence of the QTL in a tomato plant, which presence can be detected by the use of the herein disclosed markers.

The nucleotide sequence of a QTL of the presently disclosed subject matter can for instance be resolved by determining the nucleotide sequence of one or more markers linked to the QTL and designing internal primers for the marker sequences that can then be used to further determine the sequence of the QTL outside of the marker sequences. For instance, the nucleotide sequence of the SSR markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art. In embodiments of such methods for detecting the presence of a QTL in a tomato plant, the method can also comprise providing a oligonucleotide or polynucleotide capable of hybridizing under stringent hybridization conditions to a nucleic acid sequence of a marker linked to the QTL, in some embodiments selected from the markers disclosed herein, contacting the oligonucleotide or polynucleotide with digested genomic nucleic acid of a tomato plant, and determining the presence of specific hybridization of the oligonucleotide or polynucleotide to the digested genomic nucleic acid.

In some embodiments, the method is performed on a nucleic acid sample obtained from the tomato plant, although in situ hybridization methods can also be employed. Alternatively, one of ordinary skill in the art can, once the nucleotide sequence of the QTL has been determined, design specific hybridization probes or oligonucleotides capable of hybridizing under stringent hybridization conditions to the nucleic acid sequence of the QTL and can use such hybridization probes in methods for detecting the presence of a QTL disclosed herein in a tomato plant.

In a further aspect of the invention, there is provided a method for detecting a QTL linked to significantly increased fruit firmness in fruit from a cultivated tomato plant compared to a control tomato plant comprising the steps of a) crossing a donor tomato plant with a recipient tomato plant to provide offspring plants, b) quantitatively determining the fruit firmness in the fruit of said offspring plants c) establishing a genetic linkage map that links the observed increased fruit firmness to the presence of at least one DNA marker from said donor plant in said offspring plants and d) assigning to a QTL the DNA markers on said map that are linked to significantly increased fruit firmness.

In a specific embodiment, the donor plant has fruit with a significantly increased fruit firmness compared to said recipient plant.

The donor plant is preferably *S. pennellii* and the recipient plant is preferably *S. lycopersicum*. In all cases, the recipient plant is the control plant.

The donor plant or the recipient plant could be any one of the following: any plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium,* or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into *S.* 'N *peruvianum*' and *S.* 'Callejon de Huayles', *S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium* (Knapp (2005))

In a specific embodiment, the fruit firmness range in offspring plants is 1.2 to 2.0 times greater than that of fruit produced from a control tomato plant at the harvesting stage.

In a specific embodiment, the fruit firmness range in offspring plants is 1.2 to 1.5 times greater than that of fruit produced from a control tomato plant at the harvesting stage.

The harvesting stage is preferably the mature green stage. Alternatively, the harvesting stage can be any chosen point in the development of the tomato fruit, which includes but is not limited to the immature green stage, rapid expansion stage, mature green stage, breaker stage, red ripe stage or 1, 2, 3, 4, 5, 6, 7, 8, 9 or 10 days after any of these stages, preferably 7 days after the breaker stage.

In a specific embodiment, the at least one DNA marker is found in *S. pennellii*. Alternatively, the at least one DNA marker could be found in any plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium,* or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into *S.* 'N *peruvianum*' and *S.* 'Callejon de Huayles', *S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium* (Knapp (2005))

There is also provided at least one DNA marker selected from NT3853, NT3907, TG14, HOX7A, CT277, HB2600, TG353, Lm0127, Lm1650, LE5100 and LE5200.

A QTL of the present invention is one or more of a) QTL1 linked to at least one of the DNA markers NT3853, NT3907 and TG14; orb) QTL2 linked to at least one of the DNA markers HOX7A and CT277; or c) QTL3 linked to at least one of the DNA markers HB2600, TG353; or d) QTL4 linked to at least one of the DNA markers Lm0127 and Lm1650; or e) QTL5 linked to at least one of the DNA markers LE5100 and LE5200.

In a specific embodiment, the QTL is QTL1 linked to at least one of the DNA markers NT3853, NT3907 and TG14; which is present only in the inner pericarp.

In a further aspect there is provided a QTL linked to increased fruit firmness in fruit provided by a cultivated tomato plant. Preferably the QTL is detected by a method as herein described. Alternatively, the QTL may be detected by any method known to a person skilled in the art.

Preferably, the at least one QTL of the present invention is present on chromosome 2 of tomato. More preferably, the at least one QTL is present on chromosome 2 of *S. pennellii*. More preferably, the at least one QTL is present on the long arm of chromosome 2 of *S. pennellii*. Most preferably, the at least one QTL is present on the long arm of chromosome 2 of *S. pennellii* and is any one, two, three, four or all of QTLs 1 to 5.

In a specific embodiment, the QTL of the present invention is linked to at least one DNA marker selected from the group consisting of NT3853, NT3907, TG14, HOX7A, CT277, HB2600, TG353, Lm0127, Lm1650, LE5100 and LE5200.

The QTL of the present invention is one or more of a) QTL1 linked to at least one of the DNA markers NT3853, NT3907 and TG14; b) QTL2 linked to at least one of the DNA markers HOX7A and CT277; c) QTL3 linked to at least one of the DNA markers HB2600, TG353; d) QTL4 linked to at least one of the DNA markers Lm0127 and Lm1650; e) QTL5 linked to at least one of the DNA markers LE5100 and LE5200; and combinations thereof.

In a specific embodiment, the QTL is QTL1 linked to at least one of the DNA markers NT3853, NT3907 and TG14; which is present only in the inner pericarp.

There is further provided an isolated DNA sample obtained from a tomato plant comprising any one, two, three, four or all of QTLs 1 to 5. The DNA sample may be isolated as described in the examples or by any other means familiar to the skilled person.

Production of Tomato Fruit with Increased Firmness by Transgenic Methods

According to another aspect of the presently disclosed subject matter, a nucleic acid (in some embodiments a DNA) sequence comprising one or more of QTLS 1 to 5 or fruit firmness conferring parts thereof, can be used for the production of a tomato plant providing fruit with increased firmness compared to a control tomato plant. In this aspect, the presently disclosed subject matter provides for the use of QTLs as defined herein or increased fruit firmness conferring parts thereof, for producing a tomato plant providing fruit with increased firmness compared to a control tomato plant, which use involves the introduction of a nucleic acid sequence comprising the QTL into a suitable recipient plant. As stated, the nucleic acid sequence can be derived from a suitable donor plant with increased fruit firmness compared to a control tomato plant. A suitable source for the increased fruit firmness locus identified herein as any of QTLS 1 to 5 is *S. pennellii*. A number of tomato cultivars that have varying degrees of increased fruit firmness are commercially available.

The source of the increased fruit firmness loci described herein are introgression lines IL-2 and IL-3, which were originally generated by Dani Zamir and colleagues (Eshed & Zamir, 1994).These lines were obtained from the Tomato Genetics Resource Center at Davis, Calif. (available tgrc.uc-davis.edu/) or from Dani Zamir at the Hebrew University of Jerusalem, Israel. Once identified in a suitable donor plant, the nucleic acid sequence that comprises a QTL for increased fruit firmness, or increased fruit firmness-conferring part thereof, can be transferred to a suitable recipient plant by any method available. For instance, the nucleic acid sequence can be transferred by crossing a donor tomato plant with a recipient plant i.e. by introgression, by transformation, by protoplast fusion, by a doubled haploid technique, by embryo rescue, or by any other nucleic acid transfer system, followed by selection of offspring plants comprising one or more of the presently disclosed QTLs and exhibiting increased fruit firmness. For transgenic methods of transfer, a nucleic acid sequence comprising a QTL for increased fruit firmness, or increased fruit firmness-conferring part thereof, can be isolated from the donor plant using methods known in the art, and the thus isolated nucleic acid sequence can be transferred to the recipient plant by transgenic methods, for instance by means of a vector, in a gamete, or in any other suitable transfer element, such as a ballistic particle coated with the nucleic acid sequence.

Plant transformation generally involves the construction of an expression vector that will function in plant cells. In the presently disclosed subject matter, such a vector comprises a nucleic acid sequence that comprises a QTL for increased fruit firmness, or increased fruit firmness—conferring part thereof, which vector can comprise an increased fruit firmness conferring gene that is under control of, or operatively linked to, a regulatory element such as a promoter. The expression vector can contain one or more such operably linked gene/regulatory element combinations, provided that at least one of the genes contained in the combinations encodes increased fruit firmness. The vector(s) can be in the form of a plasmid, and can be used, alone or in combination with other plasmids, to provide transgenic plants that have increased fruit firmness using transformation methods known in the art, such as the *Agrobacterium* transformation system.

The inventors have characterized QTLs 1 to 5 at the molecular level and identified several putative candidate genes for use in an expression vector. The list of candidate genes is as follows: QTL1, as described herein relates to TG451 a MADS-box transcription factor related by sequence to *Petunia* gene pMADS3 (Tsuchimoto et al. 1993. Plant Cell 5, 843-853). QTL2, as described herein relates to the open reading frame corresponding to ethylene responsive transcription factor (SL1.00sc00226_365.1) position 3895565 to 3896029 (− strand). QTL3, as described herein relates to the open reading frame corresponding to a pectinesterase/pectinesterase inhibitor (Syngenta GeneChip probe ID, Le0023899). QTL4, as described herein relates to the open reading frame corresponding to dof zinc finger protein 6 (SL1.00sc00226_436.1.1) position 4475868 to 4476845 (+ strand). QTLS, as described herein relates to the open reading frame corresponding to equilibrative nucleoside transporter family protein (SL1.00sc00226_511.1) position 5133572 to 5135660 (− strand). Further details of the ethylene responsive transcription factor, dof zinc finger 6 and equilibrative nucleoside transporter protein can be found at solgenomics.net/.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

One method for introducing an expression vector into a plant is based on the natural transformation system of *Agrobacterium* (see e.g., Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g., Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer are provided by Gruber & Crosby, 1993, Moloney et al., 1989, and U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber & Crosby, 1993. General methods of culturing plant tissues are provided for example by Miki et al., 1993 and by Phillips et al., 1988. A reference handbook for molecular cloning techniques and suitable expression vectors is Sambrook & Russell, (2001).

Another method for introducing an expression vector into a plant is based on microprojectile-mediated transformation wherein DNA is carried on the surface of microprojectiles. The expression vector is introduced into plant tissues with a ballistic device that accelerates the microprojectiles to speeds of 300 to 600 m/s which is sufficient to penetrate plant cell walls and membranes (see e.g., Sanford et al., 1987; Klein et al., 1988; Sanford, 1988; Sanford, 1990; Klein et al., 1992; Sanford et al., 1993). Another method for introducing DNA into plants is via the sonication of target cells (see Zhang et al., 1991). Alternatively, liposome or spheroplast fusion can be used to introduce expression vectors into plants (see e.g., Deshayes et al., 1985 and Christou et al., 1987). Direct uptake of DNA into protoplasts using CaCl2) precipitation, polyvinyl alcohol, or poly-L-omithine has also been reported (see e.g., Hain et al. 1985 and Draper et al., 1982). Electroporation of protoplasts and whole cells and tissues has also been described (D'Halluin et al., 1992 and Laursen et al., 1994).

Other well known techniques such as the use of BACs, wherein parts of the tomato genome are introduced into bacterial artificial chromosomes (BACs), ie., vectors used to clone DNA fragments (100- to 300-kb insert size; average 150 kb) in *Escherichia coli* cells, based on naturally occurring F-factor plasmid found in the bacterium *E. coli*. (Zhao & Stodoisky, 2004) can be employed for example in combination with the Bi BAC system (Hamilton, 1997) to produce transgenic plants. One example of an over-expression vector is pGWB405 (Nakagawa T, Suzuki T, Murata S at el. Improved Gateway Binary Vectors: High-performance Vectors for CREATION of Fusion Constructs in Transgenic Analysis of Plants. Bioscience biotechnology Biochemistry, 71(8)2095-2010, 2007). For overexpression construct production, sequence corresponding to the complete open reading frame of the candidate gene involved in modulating tomato fruit firmness can be cloned in front of the CaMV 35S promoter using the Gateway clone system which avoids the need for restriction sites. Such a construct also contains the CaMV terminator at the opposite end. For RNAi construct production, a fragment of the coding sequence unique to the candidate gene involved in modulating tomato fruit firmness can be cloned, for example, in the Gateway system RNAi vector pK7GWIWG2(I).

Following transformation of tomato target tissues, expression of the above described selectable marker genes allows for preferential selection of transformed cells, tissues and/or plants, using standard regeneration and selection methods.

Figure 8:
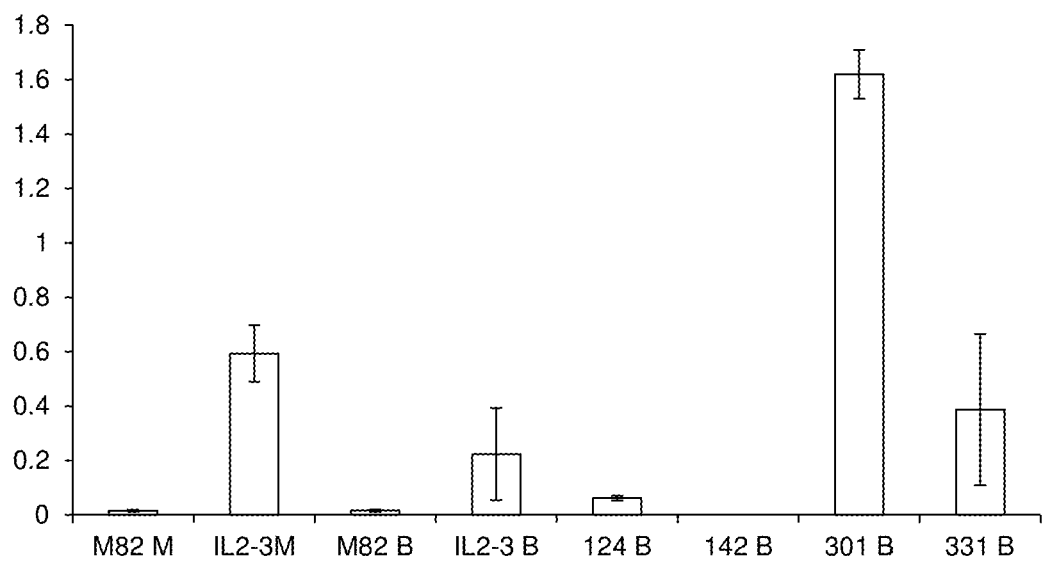
FIG. 8 Normalised relative mRNA concentrations of Pectin methylesterase in lines M82, IL2-3, 124, 142, 301 and 331 at the mature green stage (denoted M) or at the breaker stage (denoted B) as measured in (Panel A) outer pericarp and (Panel B) inner pericarp. Texture data from the same lines is shown for (Panel C) outer pericarp and (Panel D) inner pericarp. The letter H denotes the line has a heterozygous introgression.
Figure 8:
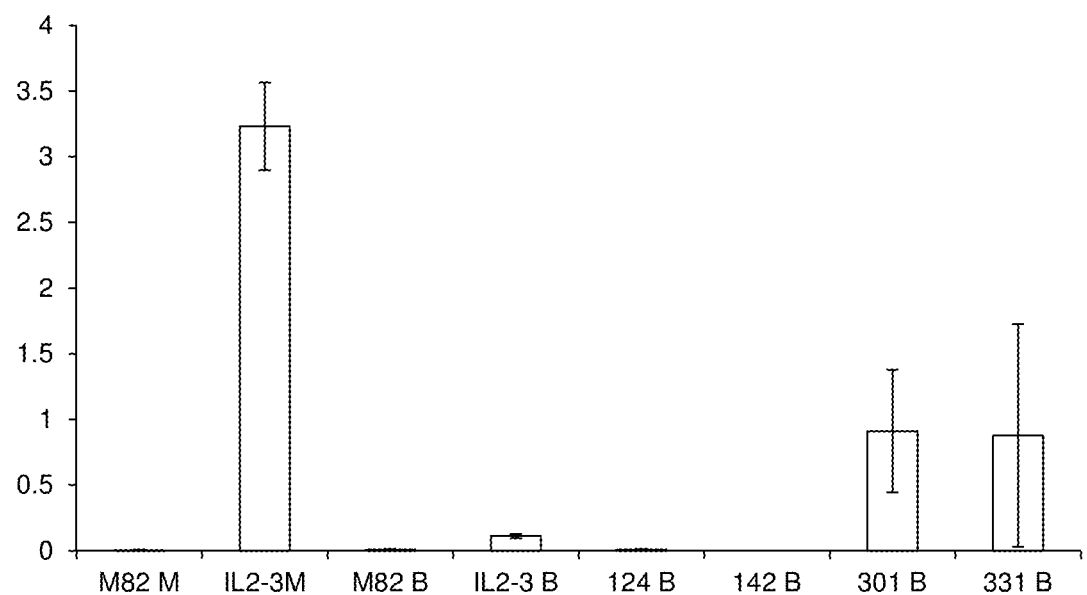
Figure 8:
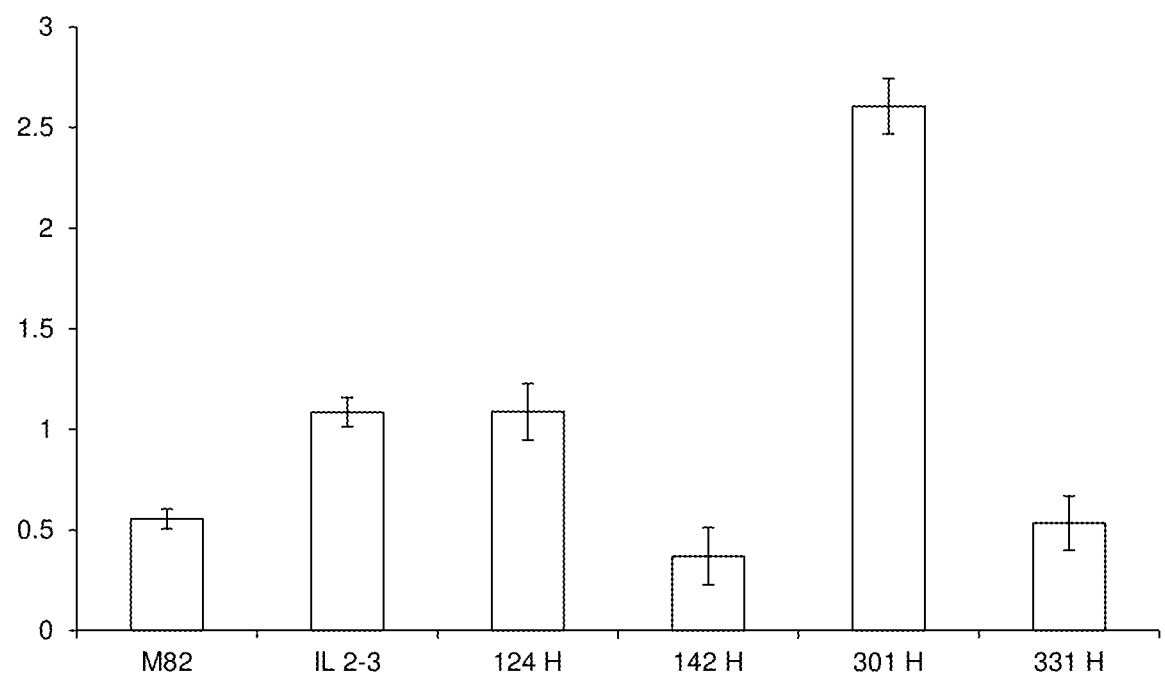
Figure 8:
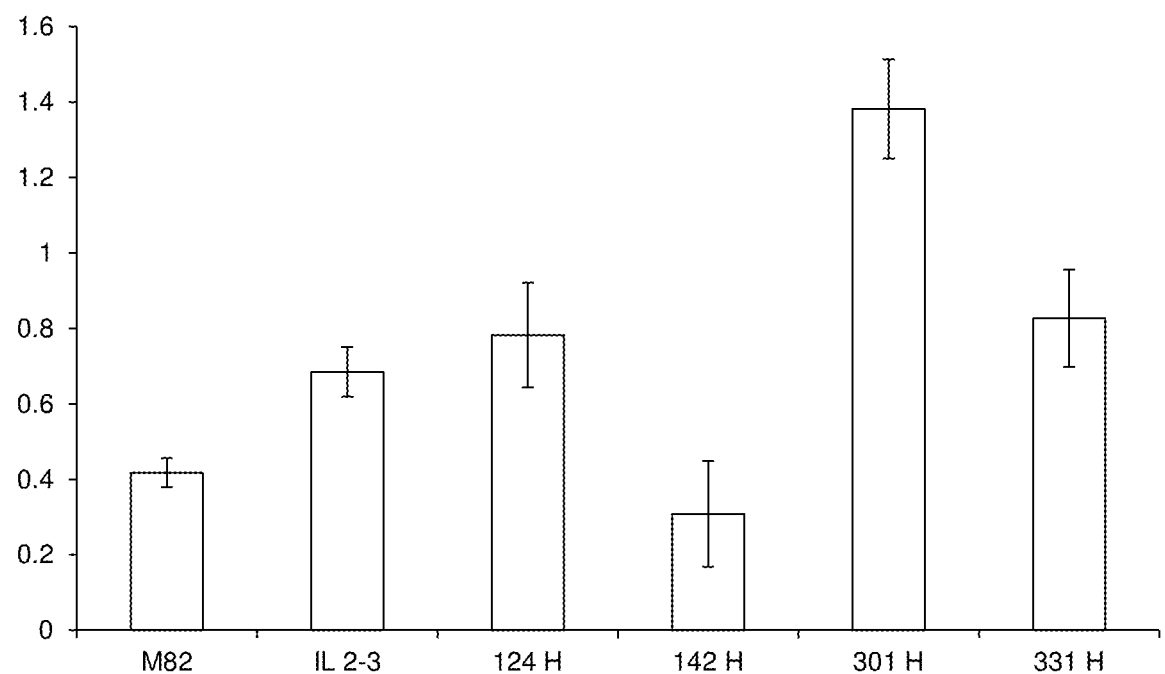
Figure 9:
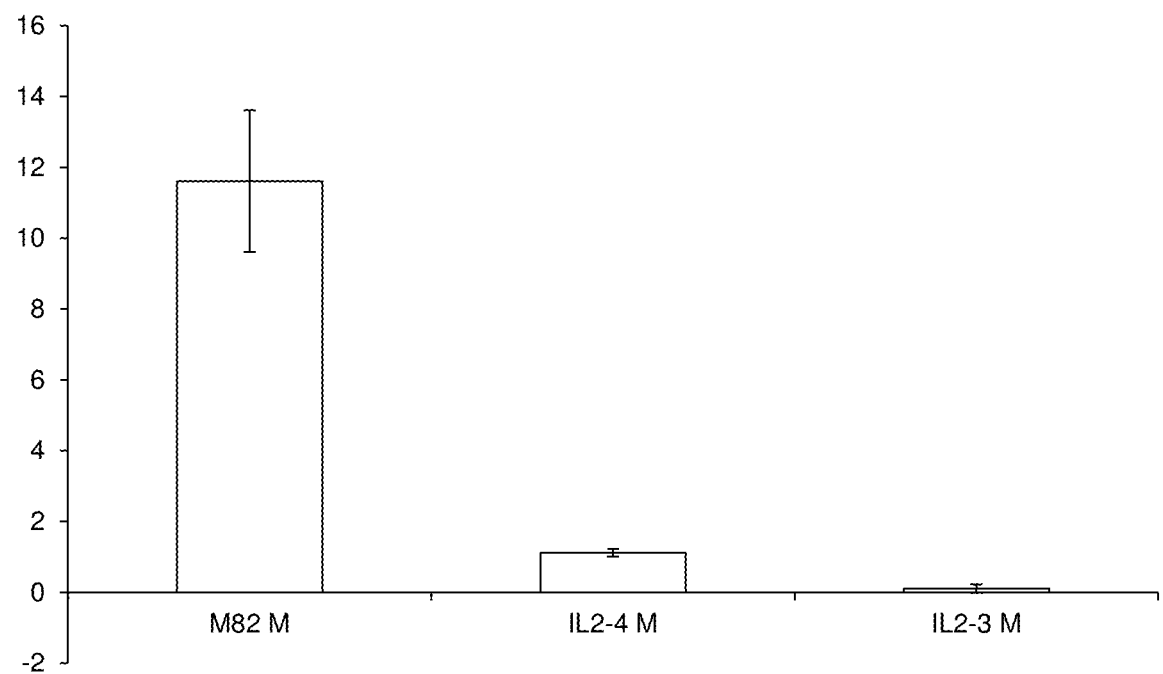
FIG. 9 Normalised relative mRNA concentrations of Dof zinc finger protein 6 in lines M82, IL2-4 and IL2-3 at the mature green stage (denoted M) as measured in (Panel A) outer pericarp and (Panel B) inner pericarp.
Figure 9:
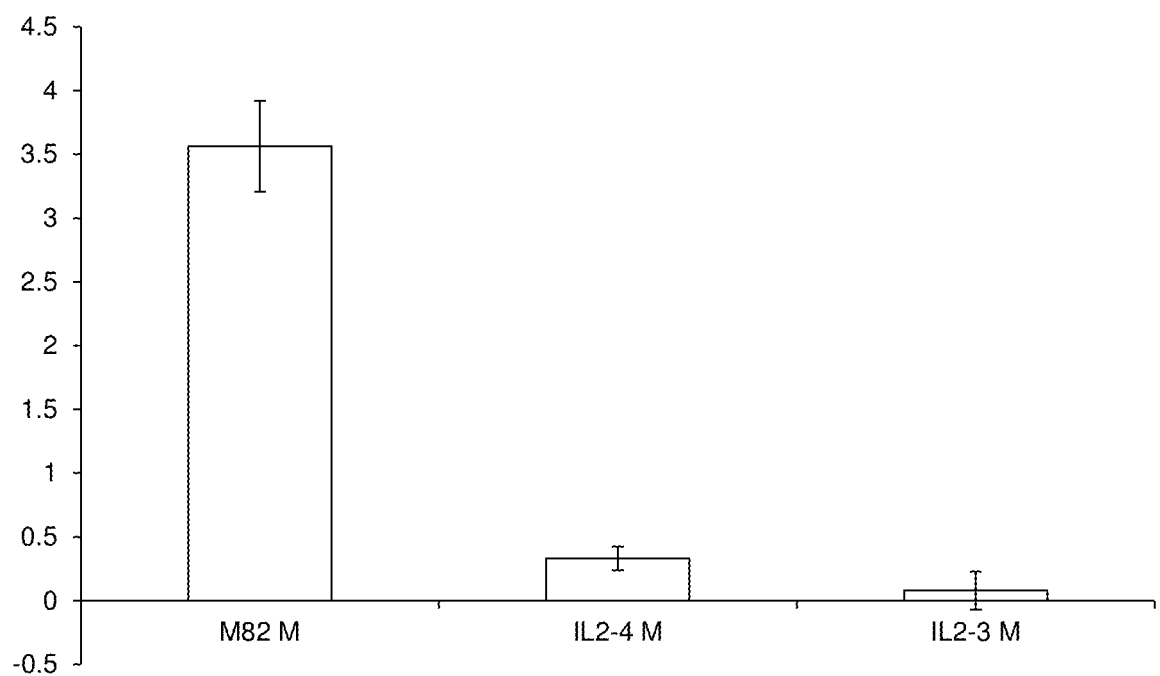

There is also provided 5 genes the expression levels of which are altered in recombinants with greater fruit firmness. The 5 genes code for TG451 (a MADS box transcription factor), ethylene responsive transcription factor 12, pectin methylesterase, dof zinc finger protein 6 and equilibrative nucleoside transporter family protein and were found to correlate to the positions of QTLs 1 to 5 respectively. mRNA expression analysis showed that ethylene responsive transcription factor 12 was negatively correlated with increased firmness at the breaker stage whereas pectin methylesterase was positively correlated (FIG. 8). Dof zinc finger protein mRNA levels were lower in introgression lines IL2-4 and IL2-3 compared with wild type M82 (FIG. 9). In light of this data it is predicted that plants, such as tomato plants, which have downregulated levels of or are absent of ethylene responsive transcription factor 12 and/or Dof zinc finger protein 6 and plants which have upregulated (or overexpressed) levels of pectin methylesterase would display increased fruit firmness. TG451, a MADS box transcription factor, and equilibrative nucleoside transporter family protein have also been implicated in improved fruit firmness (see example 9).

The present invention therefore provides an isolated nucleotide sequence selected from the group consisting of: a) a nucleotide sequence corresponding to the open reading frame or part thereof corresponding to the following: ethylene responsive transcription factor 12 or pectin methylesterase or Dof zinc finger protein 6 or TG451 or equilibrative nucleoside transporter family protein); b) a nucleotide sequence that is at least 80% identical to the nucleotide sequence of a); c) a nucleotide sequence comprising at least 21 consecutive nucleotides of the nucleotide sequence of a); d) a nucleotide sequence that hybridises under stringent conditions to the complement of any of nucleotide sequences a) to c); and e) a nucleotide sequence that is the complement to the nucleotide sequences of any one of a) to d). In one embodiment, the nucleotide sequence of step b) is at least 90% identical to the nucleotide sequence of a).

In one embodiment, the isolated nucleotide sequence of the invention is TG451, a MADS box transcription factor. In another embodiment, the isolated nucleotide sequence of the invention is ethylene responsive transcription factor 12. In another embodiment, the isolated nucleotide sequence of the invention is pectin methylesterase. In another embodiment, the isolated nucleotide sequence of the invention is Dof zinc finger protein 6. In another embodiment, the isolated nucleotide sequence of the invention is equilibrative nucleoside transporter family protein.

There is also provided a vector comprising the isolated nucleotide sequence of the invention. In one embodiment, the isolated nucleotide sequence is in the sense orientation. In another embodiment, the isolated nucleotide sequence is in the antisense orientation.

There is also provided a host cell which expresses a vector of the invention.

There is also provided a transgenic plant or part thereof comprising a host cell of the invention. In one embodiment, the transgenic plant or part thereof is a monocot. In another embodiment, the plant or part thereof is a dicot, for example a tomato.

There is also provided a method for producing a transgenic plant comprising regenerating a plant from a host cell according to the invention.

There is also provided a cultivated plant or part thereof produced by a method according to the invention.

There is also provided a method of manipulating the texture of fruit of a transgenic plant, for example a tomato plant comprising transforming said plant with a vector of the invention. In one embodiment, the speed of fruit ripening is increased when compared with fruit from an untransformed plant. In another embodiment, the speed of fruit ripening is decreased when compared with fruit from an untransformed plant. In one embodiment, the speed of tomato ripening is measured at breaker stage.

There is also provided a method of manipulating tomato fruit pigment content in fruit of a transgenic plant, for example a tomato plant comprising transforming said plant with a vector of the invention. In one embodiment, the fruit pigment content is increased compared with fruit from an untransformed plant. In one embodiment, the fruit pigment content is decreased compared with fruit from an untransformed plant. In one embodiment, the fruit pigment content is measured at breaker stage.

There is also provided a plant, for example a tomato plant or part thereof obtained by a method of the invention.

There is also provided a method of detecting genetic markers indicative of tomato texture of a plant of the Solanaceae family, comprising isolating DNA from said plant and from one or both parents of said plant; screening for genetic markers in a region of said DNA at or near sequence corresponding to an isolated sequence of the invention; and determining co-inheritance of said markers from one or both parents to said individual.

There is also provided a genetic marker detectable by a method of detecting genetic markers of the invention.

There is also provided use of a genetic marker of the invention for the production of a cultivated tomato plant capable of bearing tomato fruit.

There is also provided a cultivated tomato plant or part thereof produced by a method of the invention.

There is also provided use of a cultivated tomato plant or part thereof according to the invention in the fresh cut market or for food processing.

There is also provided use of an isolated nucleotide sequence of the invention in the manipulation of speed of ripening or of pigment content of fruit of a plant, preferably a tomato plant, wherein said manipulation is effected by genetic modification of said plant.

There is also provided use of a method according to the invention, wherein said genetic modification is introduced by a method selected from the list consisting of transposon insertion mutagenesis, T-DNA insertion mutagenesis, TILL-ING, site-directed mutagenesis, directed evolution, and homologous recombination. In one embodiment, genetic modification is introduced by TILLING.

Production of Tomato Plants with Increased Fruit Firmness by Non Transgenic Methods In some embodiments for producing a tomato plant with increased fruit firmness, protoplast fusion can be used for the transfer of nucleic acids from a donor plant to a recipient plant. Protoplast fusion is an induced or spontaneous union, such as a somatic hybridization, between two or more protoplasts (the cell walls of which are removed by enzymatic treatment) to produce a single bi- or multi-nucleate cell. The fused cell, which can even be obtained with plant species that cannot be interbred in nature, is tissue cultured into a hybrid plant exhibiting the desirable combination of traits. More specifically, a first protoplast can be obtained from a tomato plant or other plant line that exhibits increased fruit firmness. A second protoplast can be obtained from a second tomato plant or other plant variety, preferably a tomato plant line that comprises commercially valuable characteristics. The protoplasts are then fused using traditional protoplast fusion procedures, which are known in the art.

Alternatively, embryo rescue can be employed in the transfer of a nucleic acid comprising one or more QTLs as described herein from a donor tomato plant to a recipient tomato plant. Embryo rescue can be used as a procedure to isolate embryos from crosses wherein plants fail to produce viable seed. In this process, the fertilized ovary or immature seed of a plant is tissue cultured to create new plants (Pierik, 1999). The presently disclosed subject matter also relates to methods for producing tomato plant with increased fruit firmness comprising performing a method for detecting the presence of a QTL linked to increased fruit firmness in a donor tomato plant as described herein, and transferring a nucleic acid sequence comprising at least one QTL thus detected, or an increased fruit firmness-conferring part thereof, from the donor plant to a recipient tomato plant. The transfer of the nucleic acid sequence can be performed by any of the methods previously described herein.

An exemplary embodiment of such a method comprises the transfer by introgression of the nucleic acid sequence from a donor tomato plant into a recipient tomato plant by crossing the plants. This transfer can thus suitably be accomplished by using traditional breeding techniques. QTLs are introgressed in some embodiments into commercial tomato varieties using marker-assisted selection (MAS) or marker-assisted breeding (MAB). MAS and MAB involves the use of one or more of the molecular markers for the identification and selection of those offspring plants that contain one or more of the genes that encode for the desired trait. In the context of the presently disclosed subject matter, such identification and selection is based on selection of QTLs of the presently disclosed subject matter or markers associated therewith. MAS can also be used to develop near-isogenic lines (NIL) harboring the QTL of interest, allowing a more detailed study of each QTL effect and is also an effective method for development of backcross inbred line (BIL) populations (see e.g., Nesbitt & Tanksley, 2001; van Berloo et al., 2001). Tomato plants developed according to these embodiments can advantageously derive a majority of their traits from the recipient plant, and derive increased fruit firmness from the donor plant. As discussed herein, traditional breeding techniques can be used to introgress a nucleic acid sequence encoding for increased fruit firmness into a recipient tomato plant. In some embodiments, a donor tomato plant that exhibits increased fruit firmness and comprising a nucleic acid sequence encoding for increased fruit firmness is crossed with a recipient tomato plant that in some embodiments exhibits commercially desirable characteristics.

The resulting plant population (representing the F1 hybrids) is then self-pollinated and set seeds (F2 seeds). The F2 plants grown from the F2 seeds are then screened for increased fruit firmness by methods known to the skilled person.

Tomato plant lines with increased fruit firmness can be developed using the techniques of recurrent selection and backcrossing, selfing, and/or dihaploids, or any other technique used to make parental lines. In a method of recurrent selection and backcrossing, increased fruit firmness can be introgressed into a target recipient plant (the recurrent parent) by crossing the recurrent parent with a first donor plant, which differs from the recurrent parent and is referred to herein as the "non-recurrent parent". The recurrent parent is a plant that does not have increased fruit firmness but does possess commercially desirable characteristics.

In some embodiments, the non-recurrent parent exhibits increased fruit firmness and comprises a nucleic acid sequence that encodes for increased fruit firmness. The non-recurrent parent can be any plant variety or inbred line that is cross-fertile with the recurrent parent.

The progeny resulting from a cross between the recurrent parent and non-recurrent parent are backcrossed to the recurrent parent. The resulting plant population is then screened for increased fruit firmness. Marker-assisted selection (MAS) can be performed using one or more of the herein described molecular markers, or by using hybridization probes, or polynucleotides to identify those progeny that comprise a nucleic acid sequence encoding for increased fruit firmness. Also, MAS can be used to confirm the results obtained from the quantitative fruit firmness measurements.

Following screening, the F1 hybrid plants that exhibit an increased fruit firmness phenotype or, in some embodiments, genotype and thus comprise the requisite nucleic acid sequence encoding for increased fruit firmness, are then selected and backcrossed to the recurrent parent for a number of generations in order to allow for the tomato plant to become increasingly inbred. This process can be performed for two, three, four, five, six, seven, eight, or more generations. In principle, the progeny resulting from the process of crossing the recurrent parent with the increased fruit firmness non-recurrent parent are heterozygous for one or more genes that encode for increased fruit firmness.

In general, a method of introducing a desired trait into a hybrid tomato variety may comprise:

(a) crossing an inbred tomato parent with another tomato plant that comprises one or more desired traits, to produce F1 progeny plants, wherein the desired trait is increased fruit firmness;

(b) selecting the F1 progeny plants that have the desired trait to produce selected F1 progeny plants, in some embodiments using molecular markers as described herein;

(c) backcrossing the selected progeny plants with the inbred tomato parent plant to produce backcross progeny plants;
(d) selecting for backcross progeny plants that have the desired trait and morphological and physiological characteristics of the inbred tomato parent plant, wherein the selection comprises the isolation of genomic DNA and testing the DNA for the presence of at least one molecular marker for QTL1, QTL2, QTL3, QTL4 and/or QTL5, in some embodiments as described herein;
(e) repeating steps (c) and (d) two or more times in succession to produce selected third or higher backcross progeny plants;
(f) optionally selfing selected backcross progeny in order to identify homozygous plants; and
(g) crossing at least one of the backcross progeny or selfed plants with another inbred tomato parent plant to generate a hybrid tomato variety with the desired trait and all of the morphological and physiological characteristics of hybrid tomato variety when grown in the same environmental conditions.

As indicated, the last backcross generation can be selfed in order to provide for homozygous pure breeding (inbred) progeny having increased fruit firmness. Thus, the result of recurrent selection, backcrossing, and selfing is the production of lines that are genetically homogenous for the genes linked to increased fruit firmness, and in some embodiments as well as for other genes linked to traits of commercial interest.

Accordingly, there is provided a method of producing a tomato plant which provides fruit with increased fruit firmness as herein described.

In a specific embodiment there is provided a method of producing a tomato plant which provides fruit with increased fruit firmness as herein described comprising the steps of performing a method for detecting a QTL linked to increased fruit firmness as herein described, and transferring a nucleic acid comprising at least one QTL thus detected, from a donor tomato plant to a recipient tomato plant, wherein said increased fruit firmness is measured in fruit from an offspring cultivated tomato plant compared to fruit from a control tomato plant.

In a specific embodiment there is provided a method of producing a cultivated tomato plant which provides fruit with increased fruit firmness as herein described wherein said transfer of nucleic acid is performed by transformation, by protoplast fusion, by a doubled haploid technique or by embryo rescue.

In a specific embodiment there is provided a method of producing a cultivated tomato plant which provides fruit with increased fruit firmness as herein described, wherein the fruit firmness range in the offspring tomato plant is 1.2 to 2.0 times greater than fruit of a control tomato plant at the harvesting stage. Alternatively, the fruit firmness range in the offspring tomato plant is 1.2 to 1.5 times greater than fruit from a control tomato plant at the harvesting stage. Preferably the harvesting stage is mature green stage. Alternatively, the harvesting stage can be the immature green stage, rapid expansion stage, breaker stage or red ripe stage or 1, 2, 3, 4, 5, 6, 7, 8, 9 or 10 days after any of these stages.

In a specific embodiment there is provided a method of producing a tomato plant which provides fruit with increased fruit firmness as herein described, wherein the fruit firmness range remains up until breaker plus 7 days.

In a further aspect there is provided a method of producing a tomato plant which provides fruit with increased fruit firmness as herein described, wherein the donor plant is *S. pennellii* and the recipient plant is *S. lycopersicum*. Alternatively, the donor plant or the recipient plant could be any one of the following: any plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne*, *L. cheesmanii*, *L. chilense*, *L. chmielewskii*, *L. esculentum* (now *S. pennellii*), *L. hirsutum*, *L. parviborum*, *L. pennellii*, *L. peruvianum*, *L. pimpinellifolium*, or *S. lycopersicoides*. The newly proposed scientific name for *L. esculentum* is *S. pennellii*. Similarly, the names of the wild species may be altered. *L. pennellii* has become *S. pennellii*, *L. hirsutum* may become *S. habrochaites*, *L. peruvianum* may be split into *S.* 'N *peruvianum*' and *S.* 'Callejon de Huayles', *S. peruvianum*, and *S. corneliomuelleri*, *L. parviflorum* may become *S. neorickii*, *L. chmielewskii* may become *S. chmielewskii*, *L. chilense* may become *S. chilense*, *L. cheesmaniae* may become *S. cheesmaniae* or *S. galapagense*, and *L. pimpinellifolium* may become *S. pimpinellifolium* (Knapp (2005)).

There is also provided a method of producing a tomato plant which provides fruit with increased fruit firmness as herein described, wherein said QTL is one or more of a) QTL1 linked to at least one of the DNA markers NT3853, NT3907 and TG14; orb) QTL2 linked to at least one of the DNA markers HOX7A and CT277; or c) QTL3 linked to at least one of the DNA markers HB2600, TG353; d) QTL4 linked to at least one of the DNA markers Lm0127 and Lm1650; e) QTL5 linked to at least one of the DNA markers LE5100 and LE5200.

There is also provided a method of producing a tomato plant which provides fruit with increased fruit firmness as herein described, wherein said QTL is QTL1 linked to at least one of the DNA markers NT3853, NT3907 and TG14; which is present only in the inner pericarp.

In a specific embodiment there is provided a method of producing a tomato plant which provides fruit with increased fruit firmness as herein described, wherein said QTLs are QTL1 linked to at least one of the DNA markers NT3853, NT3907 and TG14; and QTL2 linked to at least one of the DNA markers HOX7A and CT277.

In a specific embodiment there is provided a method of producing a tomato plant which provides fruit with increased fruit firmness as herein described, wherein said QTLs are QTL1 linked to at least one of the DNA markers NT3853, NT3907 and TG14; and QTL3 linked to at least one of the DNA markers HB2600, TG353.

In a specific embodiment there is provided a method of producing a tomato plant which provides fruit with increased fruit firmness as herein described, wherein said QTLs are QTL1 linked to at least one of the DNA markers NT3853, NT3907 and TG14; and QTL4 linked to at least one of Lm0127 and Lm1650.

In a specific embodiment there is provided a method of producing a tomato plant which provides fruit with increased fruit firmness as herein described, wherein said QTLs are QTL1 linked to at least one of the DNA markers NT3853, NT3907 and TG14; and QTL5 linked to at least one of LE5100 and LE5200.

In a specific embodiment there is provided a method of producing a tomato plant which provides fruit with increased fruit firmness as herein described, wherein said QTLs are QTL2 linked to at least one of the DNA markers HOX7A and CT277; and QTL3 linked to at least one of the DNA markers HB2600, TG353.

In a specific embodiment there is provided a method of producing a tomato plant which provides fruit with increased fruit firmness as herein described, wherein said QTLs are QTL2 linked to at least one of the DNA markers HOX7A and CT277; and QTL4 linked to at least one of Lm0127 and Lm1650.

In a specific embodiment there is provided a method of producing a tomato plant which provides fruit with increased fruit firmness as herein described, wherein said QTLs are QTL2 linked to at least one of the DNA markers HOX7A and CT277; and QTL5 linked to at least one of LE5100 and LE5200.

In a specific embodiment there is provided a method of producing a tomato plant which provides fruit with increased fruit firmness as herein described, wherein said QTLs are QTL3 linked to at least one of the DNA markers HB2600 and TG353; and QTL4 linked to at least one of Lm0127 and Lm1650.

In a specific embodiment there is provided a method of producing a tomato plant which provides fruit with increased fruit firmness as herein described, wherein said QTLs are QTL3 linked to at least one of the DNA markers HB2600 and TG353; and QTL5 linked to at least one of LE5100 and LE5200.

In a specific embodiment there is provided a method of producing a tomato plant which provides fruit with increased fruit firmness as herein described, wherein said QTLs are QTL4 linked to at least one of Lm0127 and Lm1650; and QTL5 linked to at least one of LE5100 and LE5200.

In a specific embodiment there is provided a method of producing a tomato plant which provides fruit with increased fruit firmness as herein described, wherein said QTLs are QTL1 linked to at least one of the DNA markers NT3853, NT3907 and TG14; and QTL2 linked to at least one of the DNA markers HOX7A and CT277; and QTL3 linked to at least one of the DNA markers HB2600, TG353; and QTL4 linked to at least one of Lm0127 and Lm1650; and QTL5 linked to at least one of LE5100 and LE5200.

In a specific embodiment there is provided a method of producing a tomato plant which provides fruit with increased fruit firmness as herein described, wherein said QTL is QTL1 linked to at least one of the DNA markers NT3853, NT3907 and TG14; which is present only in the inner pericarp.

In a further aspect there is provided a tomato plant, or part thereof, obtainable by a method as herein described.

In a further aspect there is provided a cultivated tomato plant comprising a QTL responsible for increased fruit firmness as herein described.

In a further aspect there is provided a hybrid tomato plant, or part thereof, obtainable by crossing a tomato plant as herein described with a tomato plant that exhibits commercially desirable characteristics.

In a further aspect there is provided a tomato seed produced by growing the tomato plant as herein described.

In a further aspect there is provided a tomato seed produced by crossing the cultivated tomato plant as herein described with a plant having desirable phenotypic traits to obtain a plant that has significantly increased fruit firmness compared to a control plant.

In a further aspect there is provided use of a QTL as herein described for the production of tomato plants having increased fruit firmness compared to control plants.

In a further aspect there is provided use of a tomato plant having increased fruit firmness as herein described for expanding the harvesting slot of tomato fruit. The harvesting slot can be expanded by any one of 1, 2, 3, 4, 5, 6, 7, 8, 9 or 10 days.

In a further aspect there is provided use of a tomato plant having increased fruit firmness as herein described in the fresh cut market or for food processing.

In a further aspect there is provided processed food made from a tomato plant comprising the at least one QTL as herein described.

EMBODIMENTS OF THE INVENTION

Embodiment 1 a tomato fruit with significantly increased fruit firmness at the harvesting stage linked to at least one genetic element in the cultivated tomato plant producing said tomato fruit, wherein said firmness is from between 1.2 to 2.0 times greater than that of fruit from a control tomato plant which does not have the said at least one genetic element.

Embodiment 2 a tomato fruit according to embodiment 1 wherein the harvesting stage is the mature green stage Embodiment 3 a tomato fruit according to embodiment 1 or 2 wherein the fruit firmness is from between 1.2 to 1.5 times greater than that produced from a control tomato plant which does not have the said at least one genetic element.

Embodiment 4 a tomato fruit according to any one of embodiments 1 to 3, wherein said firmness range is measured at breaker plus 7 days.

Embodiment 5 a tomato fruit according to any preceding embodiment wherein the at least one genetic element is located on the long arm of chromosome 2.

Embodiment 6 a cultivated tomato plant which produces tomato fruit according to any of embodiments 1 to 5 wherein said plant can be characterised by a) the at least one genetic element is linked to at least one DNA marker selected from the group consisting of NT3853, NT3907, TG14, HOX7A, CT277, HB2600, TG353, Lm0127, Lm1650, LE5100 and LE5200 and/or b) the at least one genetic element is complementary to the corresponding genetic element in *Solanum pennellii* lines IL2-3 and IL2-4 deposited under accession numbers LA4038 and LA4039, respectively, wherein the said at least one genetic element in LA4038 and LA4039 is linked to at least one DNA marker selected from the group consisting of NT3853, NT3907, TG14, HOX7A, CT277, HB2600, TG353, Lm0127, Lm1650, LE5100 and LE5200.

Embodiment 7 a cultivated tomato plant according to embodiment 6 wherein the at least one genetic element is one or more QTL selected from a) QTL1 linked to at least one of the DNA markers NT3853, NT3907 and TG14; orb) QTL2 linked to at least one of the DNA markers HOX7A and CT277; or c) QTL3 linked to at least one of the DNA markers HB2600, TG353; or d) QTL4 is linked to at least one of the DNA markers Lm0127 and Lm1650; or e) QTL5 is linked to at least one of the DNA markers LE5100 and LE5200.

Embodiment 8 a cultivated tomato plant according to embodiment 7 wherein the QTL is QTL1 associated with at least one of the DNA markers NT3853, NT3907 and TG14; which is present only in the inner pericarp.

Embodiment 9 a cultivated tomato plant according to any one of embodiments 6 to 8 wherein said plant is an inbred, a dihaploid or a hybrid.

Embodiment 10 a cultivated tomato plant according to embodiment 9 wherein said plant is male sterile.

Embodiment 11 a tomato seed which produces a cultivated tomato plant according to any one of embodiments 6 to 10

Embodiment 12

Plant part of a cultivated tomato plant according to embodiment 11.

Embodiment 13

Plant material obtainable from a plant part of a cultivated tomato plant according to embodiment 12.

Embodiment 14 a method for detecting a QTL linked to significantly increased fruit firmness in fruit from a cultivated tomato plant compared to a control tomato plant comprising the steps of a) crossing a donor tomato plant with a recipient tomato plant to provide offspring cultivated tomato plants, b) quantitatively determining the firmness in the fruit of said offspring plants c) establishing a genetic linkage map that links the observed increased fruit firmness to the presence of at least one DNA marker from said donor plant in said offspring plants and d) assigning to a QTL the DNA markers on said map that are linked to significantly increased fruit firmness.

Embodiment 15

The method according to embodiment 14 wherein said donor plant has a significantly increased fruit firmness compared to said recipient plant.

Embodiment 16

The method of embodiment 14 or 15 wherein the donor plant is *Solanum pennellii* and the recipient plant is *Solanum lycopersicum*.

Embodiment 17

The method of any one of embodiments 14 to 16 wherein the fruit firmness range in offspring plants is 1.2 to 2.0 times greater than that of fruit produced from a control tomato plant at the harvesting stage.

Embodiment 18

The method of embodiment 17 wherein the fruit firmness range in offspring plants is 1.2 to 1.5 times greater than that of fruit produced from a control tomato plant at the harvesting stage.

Embodiment 19

The method of any one of embodiments 17 to 18 wherein the harvesting stage is the mature green stage.

Embodiment 20

The method of any one of embodiments 14 to 19 wherein the at least one DNA marker is found in *Solanum pennellii*.

Embodiment 21

The method of any one of embodiments 14 to 20 wherein the at least one DNA marker is selected from NT3853, NT3907, TG14, HOX7A, CT277, HB2600, TG353, Lm0127, Lm1650, LE5100 and LE5200.

Embodiment 22

The method of any one of embodiments 14 to 21 wherein said QTL is one or more of a) QTL1 linked to at least one of the DNA markers NT3853, NT3907 and TG14; or b) QTL2 linked to at least one of the DNA markers HOX7A and CT277; or c) QTL3 linked to at least one of the DNA markers HB2600, TG353; or d) QTL4 linked to at least one of the DNA markers Lm0127 and Lm1650; or e) QTL5 linked to at least one of the DNA markers LE5100 and LE5200.

Embodiment 23

The method of embodiment 22 wherein said QTL is QTL1 associated with at least one of the DNA markers NT3853, NT3907 and TG14; which is present only in the inner pericarp.

Embodiment 24 a QTL responsible for increased fruit firmness in fruit provided by a cultivated tomato plant detected by a method according to any one of embodiments 14 to 23.

Embodiment 25 a QTL according to embodiment 24 located on the long arm of chromosome 2.

Embodiment 26 a QTL according to any one of embodiments 24 to 25 associated with at least one DNA marker selected from the group consisting of NT3853, NT3907, TG14, HOX7A, CT277, HB2600, TG353, Lm0127, Lm1650, LE5100 and LE5200.

Embodiment 27 a QTL according to any one of embodiments 24 to 26 wherein said QTL is one or more of a) QTL1 linked to at least one of the DNA markers NT3853, NT3907 and TG14; b) QTL2 linked to at least one of the DNA markers HOX7A and CT277; c) QTL3 linked to at least one of the DNA markers HB2600, TG353; d) QTL4 linked to at least one of the DNA markers Lm0127 and Lm1650; e) QTL5 linked to at least one of the DNA markers LE5100 and LE5200.

Embodiment 28 a QTL according to embodiment 27 wherein said QTL is QTL1 linked to at least one of the DNA markers NT3853, NT3907 and TG14; which is present only in the inner pericarp.

Embodiment 29

An isolated DNA sample obtained from a tomato plant comprising a QTL according to any one of embodiments 24 to 28.

Embodiment 30 a method of producing a cultivated tomato plant which provides fruit with significantly increased fruit firmness according to any one of embodiments 1 to 5

Embodiment 31 a method of producing a cultivated tomato plant which provides fruit with increased fruit firmness according to embodiment 30 comprising the steps of performing a method for detecting a QTL associated with significantly increased fruit firmness according to any one of embodiments 14 to 23, and transferring a nucleic acid comprising at least one QTL thus detected, from a donor tomato plant to a recipient tomato plant, wherein said increased fruit firmness is measured in fruit from an offspring cultivated tomato plant compared to fruit from a control tomato plant.

Embodiment 32 a method of producing a cultivated tomato plant which provides fruit with increased fruit firmness according to any one of embodiments 30 to 31 wherein said transfer of nucleic acid is performed by transformation, by protoplast fusion, by a doubled haploid technique or by embryo rescue.

Embodiment 33 a method of producing a cultivated tomato plant which provides fruit with increased fruit firmness according to any one of embodiments 30 to 32, wherein the fruit firmness range in the donor tomato plant is 1.2 to 2.0 times greater than fruit of a control tomato plant at the mature green stage.

Embodiment 34 a method of producing a cultivated tomato plant which provides fruit with increased fruit firmness according to any one of embodiments 30 to 33, wherein the fruit firmness range is measured at breaker plus 7 days.

Embodiment 35 a method of producing a cultivated tomato plant which provides fruit with increased fruit firmness according to any one of embodiments 31 to 34, wherein the donor plant is *Solanum pennellii* and the recipient plant is *Solanum lycopersicum*.

Embodiment 36 a method of producing a cultivated tomato plant which provides fruit with increased fruit firmness according to any one of embodiments 31 to 35 wherein said QTL is one or more of a) QTL1 linked to at least one of the DNA markers NT3853, NT3907 and TG14; orb) QTL2 linked to at least one of the DNA markers HOX7A and CT277; or c) QTL3 linked to at least one of the DNA markers HB2600, TG353; or d) QTL4 linked to at least one of the DNA markers Lm0127 and Lm1650; or e) QTL5 linked to at least one of the DNA markers LE5100 and LE5200.

Embodiment 37 a method of producing a cultivated tomato plant which provides fruit with increased fruit firmness according to embodiment 36 wherein said QTL is QTL1 linked to at least one of the DNA markers NT3853, NT3907 and TG14; which is present only in the inner pericarp.

Embodiment 38 a cultivated tomato plant, or part thereof, obtainable by a method according to any one of embodiments 30 to 37.

Embodiment 39 a cultivated tomato plant comprising a QTL responsible for increased fruit firmness according to any one of embodiments 24 to 28.

Embodiment 40 a hybrid tomato plant, or part thereof, obtainable by crossing a cultivated tomato plant according to embodiments 6 to 10 and 38 to 39 with a tomato plant that exhibits commercially desirable characteristics.

Embodiment 41

Tomato seed produced by growing the tomato plant of any one of embodiments 6 to 10 and 38 to 40.

Embodiment 42

Tomato seed produced by crossing the cultivated tomato plant of any one of embodiments 6 to 10 and 38 to 40 with a plant having desirable phenotypic traits to obtain a plant that has significantly increased fruit firmness compared to a control plant.

Embodiment 43

Use of a QTL according to any one of embodiments 24 to 28 for the production of tomato plants having significantly increased fruit firmness compared to control tomato plants.

Embodiment 44

Use of a tomato plant according to any one of embodiments 6 to 10 and 38 to 40 for expanding the harvesting slot of tomato fruit.

Embodiment 45

Use of a tomato plant according to any one of embodiments 6 to 10 and 38 to 40 in the fresh cut market or for food processing.

Embodiment 46

Use of a tomato fruit according to any one of embodiments 1 to 5 in the fresh cut market or for food processing

Embodiment 47

Processed food made from a tomato plant comprising the at least one genetic element according to embodiments 6 to 10.

DEPOSITED LINES

The following seed samples were deposited with NCIMB, Ferguson Building, Craibstone Estate, Bucksburn, Aberdeen AB21 9YA, Scotland, UK, on Oct. 22, 2009 under the provisions of the Budapest Treaty in the name of Syngenta Participations AG:

*Solanum lycopersicum* CV M82, deposit number NCIMB 41661

*Solanum lycopersicum* QTL NIL 301, deposit number NCIMB 41662

Line details: F2 recombinants of line IL2-3 and F3 of IL2-4 were tested for increased fruit firmness. Extra firm lines were identified including QTL recombinant line 301. F3 seed this heterozygous recombinant 301 were sown and homozygous individuals identified using markers. The F4 seed were collected and five lines re-grown and leaf DNA checked with markers. The F5 seed were then collected and deposited as QTL-NIL seed from line 301. Seed from CV M82 as the cultivated parent have also been deposited.

REFERENCES

Batu, A. and Thompson, A. K. 1998 Effects of modified atmospheric packaging on post harvest qualities of pink tomatoes, Tr. J. Agr. & Forestry, 22, 365-372

Causse M, Saliba-Colombani V, Lecomte L, Duffé P, Rousselle P, Buret M. (2002) QTL analysis of fruit quality in fresh market tomato: a few chromosome regions control the variation of sensory and instrumental traits. J Exp Bot. October; 53(377):2089-98

Chanthasombath T, Sanatem K, Phomachan C, Acedo Jr. A and Weinberger K, (2008) Postharvest Life of Breaker and Turning Tomatoes Subjected to Transient Modified Atmosphere Proc. EURASIA Sym. on Quality Management in Postharvest Systems. Acta Hort. 804, ISHS 2008

Chi W, Ma J, Zhang D, Guo J, Chen F, Lu C, and Zhang L (2008) The Pentratricopeptide Repeat Protein DELAYED GREENING1 Is Involved in the Regulation of Early Chloroplast Development and Chloroplast Gene Expression in *Arabidopsis* Plant Physiol. 147: 573-584.

Christou P, Murphy J E, and Swain W F (1987) Stable transformation of soybean by electroporation and root formation from transformed callus. Proc. Natl. Acad. Sci. USA 84:3962-3966.

Deshayes A, Herrera-Estrella L, Caboche M (1985) Liposome-mediated transformation of tobacco mesophyll protoplasts by an *Escherichia coli* plasmid. EMBO J. 4:2731-2737.

D'Halluin K, Bonne E, Bossut M, De Beuckeleer M, Leemans J (1992) Plant. Cell 4:1495-1505. Dik A J, Koning G, Kohl J (1999) Evaluation of microbial antagonists for biological control of tomato cinerea stem infection in cucumber and tomato. Eur. J. Plant Pathol. 105:115-122.

Draper J, Davey M K, Freeman J P, Cocking E C and Cox B J (1982) Ti plasmid homologous sequences present in tissues from *Agrobacterium* plasmid-transformed *Petunia* protoplasts. Plant and Cell Physiol. 23:451-458.

Eckstein F (ed) (1991) Oligonucleotides and Analogues, A Practical Approach. Oxford Univ. Press, N Y 1991.

Eriksson E E, Bovy A, Manning K, Harrison L, Andrews J, De Silva J, Tucker G A and Seymour G B (2004) Effect of the Colorless non-ripening Mutation on Cell Wall Biochemistry and Gene Expression during Tomato Fruit Development and Ripening. Plant Physiology 136:4184-4197

Eshed Y, Zamir D (1994) A genomic library of *Lycopersicon pennellii* in *S. esculentum*: a tool for fine mapping of genes. Euphytica. Dordrecht: Kluwer Academic Publishers. 1994 79: 175-179.

Exama, A., Arul, J., Lencki, R. W., Lee, L. Z. and Toupin, C. 1993. Suitability of plastic films for modified atmosphere packaging of fruits and vegetables. J. Food Sci. 58: 1365-1370.

Frary A, Nesbitt T C, Grandillo S, Knaap Evd, Cong B, Liu J, Meller J, Elber R, Alpert K B, Tanksley S D (2000) fw2.2: a quantitative trait locus key to the evolution of tomato fruit size. Science Washington. 2000; 289: 85-88.

Fridman E, Carrari F, Liu Y S, Fernie A R, Zamir D (2004) Zooming in on a quantitative trait for tomato yield using interspecific introgressions. Science 305: 1786-1789.

Geeson, J. D., Browne, K. M., Maddison, K. I., Shepherd, J. and Guaraldi, F. 1985. Modified atmosphere packaging to extend the shelf life of tomatoes. J. Food Technol. 20:339-349.

Glick B R and Thompson J E (eds) (1993) Procedures for Introducing Foreign DNA into Plants in Methods in Plant Molecular Biology & Biotechnology, CRC Press, pp. 67-88.

Gruber M Y, Crosby W L (1993) Vectors for Plant Transformation. In: Glick B R and Thompson J E (Eds.) Methods in Plant Molecular Biology & Biotechnology, CRC Press, pp. 89-119.

Hain R, Stabel P, Czernilofsky A P, Steinbliss H H, Herrera-Estrella L, Schell J (1985) Uptake, integration, expression and genetic transmission of a selectable chimaeric gene to plant protoplasts. Mol. Gen. Genet. 199:161-168.

Hamilton C M (1997) A binary-BAC system for plant transformation with high-molecular-weight DNA. Gene 200:107-116

Horsch R B, Fry J E, Hoffman N L, Eichholts D, Rogers S G, Fraley R T (1985) A simple method for transferring genes into plants. Science 227:1229-1231.

Kado C I (1991) Molecular mechanisms of crown gall tumorigenesis. Crit. Rev. Plant Sd. 10:1-32.

King, G. J., Lynn, J. R., Dover, C. J., Evans, K. M. and Seymour, G. B. (2001). Resolution of quantitative trait loci for mechanical measures accounting for gentic variation in fruit texture of apple (*Malus pumila* Mill.). Theoretical and Applied Genetics 102:1227-1235.

Klein T M, Gradziel T, Fromm M E, Sanford J C (1988). Factors influencing gene delivery into *Zea mays* cells by high velocity microprojectiles. Biotechnology 6:559-563-Klein T M, Arentzen R, Lewis P A, and Fitzpatrick-McEUigott S (1992) Transformation of microbes, plants and animals by particle bombardment. Bio/Technology 10:286-291.

Knapp S (2005) New nomenclature for *Lycopersicon* available at sgn.cornell.edu/about/solanum_nomenclature.pl.

Laursen C M, Krzyzek R A, Flick C E, Anderson P C, Spencer T M (1994) Production of fertile transgenic maize by electroporation of suspension culture cells. Plant Mol Biol. 24(1):51-61.

Manning, K., Tor, M., Poole, M., Hong, Y., Thompson, A. J., King, G. J., Giovannoni, J. J. and Seymour, G. B. (2006). A naturally occurring epigenetic mutation in a gene encoding an SBP-box transcription factor inhibits tomato fruit ripening. Nature Genetics 38:948-952.

Miki B L, Fobert P F, Charest P J, Iyer V N (1993) Procedures for Introducing Foreign DNA into Plants. In: Glick B R and Thompson J E (Eds.) Methods in Plant Molecular Biology & Biotechnology, CRC Press, pp. 67-88.

Moloney M M, Walker J M, Sharma K K (1989) High efficiency transformation of *Brassica napus* using *Agrobacterium* vectors. Plant Cell Reports 8:238-242.

Nesbitt T C, Tanksley S D (2001) fw2.2 directly affects the size of developing tomato fruit, with secondary effects on fruit number and photosynthate distribution. Plant Physiol. 127: 575-583.

Paterson A H (1996) Making genetic maps. In: Paterson A H (ed) Genome mapping in plants. R G Landes, San Diego, pp 23-39

Pearson W R (1990) Rapid and sensitive sequence comparison with FASTP and FASTA. Methods in Enzymology 183: 63-98.

Phillips R L, Somers D A, Hibberd K A. 1988. Cell/tissue culture and in vitro manipulation. In: G. F. Sprague & J. W. Dudley, eds. Corn and corn improvement, 3rd ed., p. 345-387. Madison, Wis., USA, American Society of Agronomy.

Pierik R L M (1999) In vitro Culture of Higher Plants, 4th edition, 360 pages, ISBN:0-7923-5267-X.

Sambrook J, and Russell D W (2001). Molecular Cloning: A Laboratory Manual. New York, N.Y., USA., Cold Spring Harbor Laboratory Press.

Sanford J C, Klein T M, Wolf E D, Allen N (1987). Delivery of substances into cells and tissues using a particle bombardment process. J. Particulate Sd. Technol. 5:27-37.

Sanford J C (1988) The biolistic process. Trends in Biotechnology 6:299-302.

Sanford J C (1990) Biolistic plant transformation. Physiologica Plantarum 79: 206-209.

Sanford J C, Smith F D, and Russell J A (1993) Optimizing the biolistic process for different biological applications. Methods in Enzymology 217:483-509.

Smith T, Waterman M (1981) Identification of common Molecular Sequences J. Mol. Biol: 147, 195-197.

Thompson, A. J., Tor, M., Barry, C. S., Vrebalov, J., Orfila, C., Jarvis, M. C., Giovannoni, J. J., Grierson, D. and Seymour, G. B. (1999). Molecular and genetic characterisation of a novel pleiotropic tomato ripening mutant. Plant Physiology 120:383-389.

Tijssen P (1993) Hybridization With Nucleic Acid Probes. Part I. Theory and Nucleic Acid Preparation. In: Laboratory Techniques in Biochemistry and Molecular Biology. Elsevier.

Tsuchimoto S, van der Krol A R and Chua N H. Ectopic Expression of pMADS3 in Transgenic *Petunia* Phenocopies the *Petunia* blind Mutant (1993) Plant Cell 5, 843-853.

Van Berloo R, Aalbers H, Werkman A, Niks R E (2001) Fruit firmness QTL confirmed through development of QTL-NILs for barley leaf rust fruit firmness. Mol. Breeding 8: 187-195 van Ooijen J W, Maliepaard C (1996) MapQTL® version 4.0: Software for the calculation of QTL positions on genetic maps. CPRO-DLO, Wageningen van Oijen J W, Voorips R E (2001) JoinMap® 3.0: Software for the calculation of genetic linkage maps. Plant Research International, Wageningen, Netherlands Vrebalov J, Ruezinsky D, Padmanabhan V, White R, Medrano D, Drake R, Schuch W, Giovannoni J (2002) A MADS-Box Gene Necessary for Fruit Ripening at the Tomato Ripening-Inhibitor (Rin) Locus. Science 296: 5566, 343-346

Wang S., C. J. Basten, and Z.-B. Zeng (2007). Windows QTL Cartographer 2.5 Department of Statistics, North Carolina State University, Raleigh, N.C. (available at statgen.ncsu.edu/qticart/WQTLCart.htm)

Zhang L, Cheng L, Xu N, Zhao M, Li C, Yuan J, and Jia S (1991) Efficient transformation of tobacco by ultrasonication. Biotechnology 9:996-997.

Zhao S, and Stodolsky M (2004) "Bacterial Artificial Chromosomes," Methods in Molecular Biology, Vol. 255, Humana Press Inc., Totowa, N.J., USA Zietkiewicz E, Rafalski A, Labuda D (1994) Genome fingerprinting by simple sequence repeat (SSR)-anchored polymerase chain reaction amplification. Genomics 94: 176-183

EXAMPLES

Example 1

Fruit Firmness Measurements of Introgression Lines

Seventy six *S. pennellii* ILs were grown in summer 2006 under standard greenhouse conditions (as described in the "Definitions" section). To measure fruit firmness, a transverse section was cut from the centre of the fruit using a double blade mounted on a customized cutting tool to give a section of exactly 6 mm. This section was placed on a flat plate. Using a Lloyd LRX machine equipped with a 10 N load cell, the force required to penetrate the outer and inner pericarp tissue by a 6 mm probe travelling at 10 mm/minute (maximum load) was then measured. These fruit firmness measurements on ripening fruit demonstrated that IL2-3 and IL2-4 lines had significantly increased fruit firmness during ripening in comparison with the M82 control. The most pronounced effects were in IL2-3 and fruit firmness data from the outer and inner pericarp of this line is shown in Tables 1 and 2 below.

In each table, firmness is represented by measures of maximum load (N). The values are predicted means for lines in 2 years (2007 and 2008) as generated using the Residual Maximum Likelihood (REML) statistic and takes into account variation resulting from fruit weight, truss number, date of harvest and position in glasshouse.

TABLE 1

Outer Pericarp

| Line | Year 1 (2007) | Year 2 (2008) |
|---|---|---|
| M82 cultivated parent | 0.56 ± 0.05<br>n = 423 | 0.38 ± 0.04<br>n = 122 |
| IL2-3 S. pennellii<br>introgression line | 1.09 ± 0.07<br>n = 53 | 1.35 ± 0.08<br>n = 26 |
| 301<br>(IL2-3 recombinant*) | 2.61 ± 0.14<br>n = 11 | 1.31 ± 0.13<br>n = 10 |
| 142<br>(IL2-3 recombinant*) | 0.37 ± 0.14<br>n = 10 | 0.38 ± 0.13<br>n = 8 |

TABLE 2

Inner Pericarp

| Line | Year 1 (2007) | Year 2 (2008) |
|---|---|---|
| M82 cultivated parent | 0.42 ± 0.04<br>n = 423 | 0.39 ± 0.05<br>n = 122 |
| IL2-3 S. pennellii<br>introgression line | 0.66 ± 0.07<br>n = 53 | 2.23 ± 0.09<br>n = 26 |
| 301<br>(IL2-3 recombinant*) | 1.38 ± 0.13<br>n = 11 | 1.47 ± 0.14<br>n = 10 |
| 142<br>(IL2-3 recombinant*) | 0.31 ± 0.14<br>n = 10 | 0.34 ± 0.15<br>n = 8 |

*These lines were used with many others to generate the QTL maps. They are F2 lines and hence still heterozygous at some loci.

Example 2

Development of Markers to Delineate Recombination Events in the IL2-3 and IL2-4 Introgression Lines and Confirmation of Genotypes Used in Experiments Based on the tomato genetic map (Tanksley et al, 1992; www.sgn.cornell.edu), markers were selected (FIG. 1) to distinguish and delimit the 2-3 and 2-4 introgressions on chromosome 2. Single nucleotide polymorphisms (SNPs) were identified between *S. lycopersicum* and *S. pennellii*. These were used to verify the genotype of all 7200 lines used in the experiments. Taqman-based markers for CT255, TG353, TG451 and TG583 (FIG. 1) were then generated to allow high throughput screening for informative recombinants. FIG. 1 is a cartoon showing markers delineating (A) IL2-3 (B) IL2-4 and (C) QTL-NIL 301.

Example 3

Establishment of Whether the Increased Fruit Firmness Trait is Dominant or Recessive and Collection of Sufficient IL2-3×M82F2 and IL2-4×M82F2 Seed to be Grown for Screening for Recombination Events It has been shown that the *S. pennellii* fruit firmness alleles are dominant over the M82 allele because fruit from the F1 line for the backcross between IL2-3 and M82 the fruit were firmer than the M82 parent. Seeds from crosses between IL2-3×M82 and IL2-4×M82 were obtained from Dani Zamir (The Hebrew University of Jerusalem). In most cases F1 seed was grown, but in some cases this was not available and F2 seed was obtained by selfing and selection of heterozygous F2 individuals. Seed from these individuals was collected to screen for recombinants.

Figure 2:
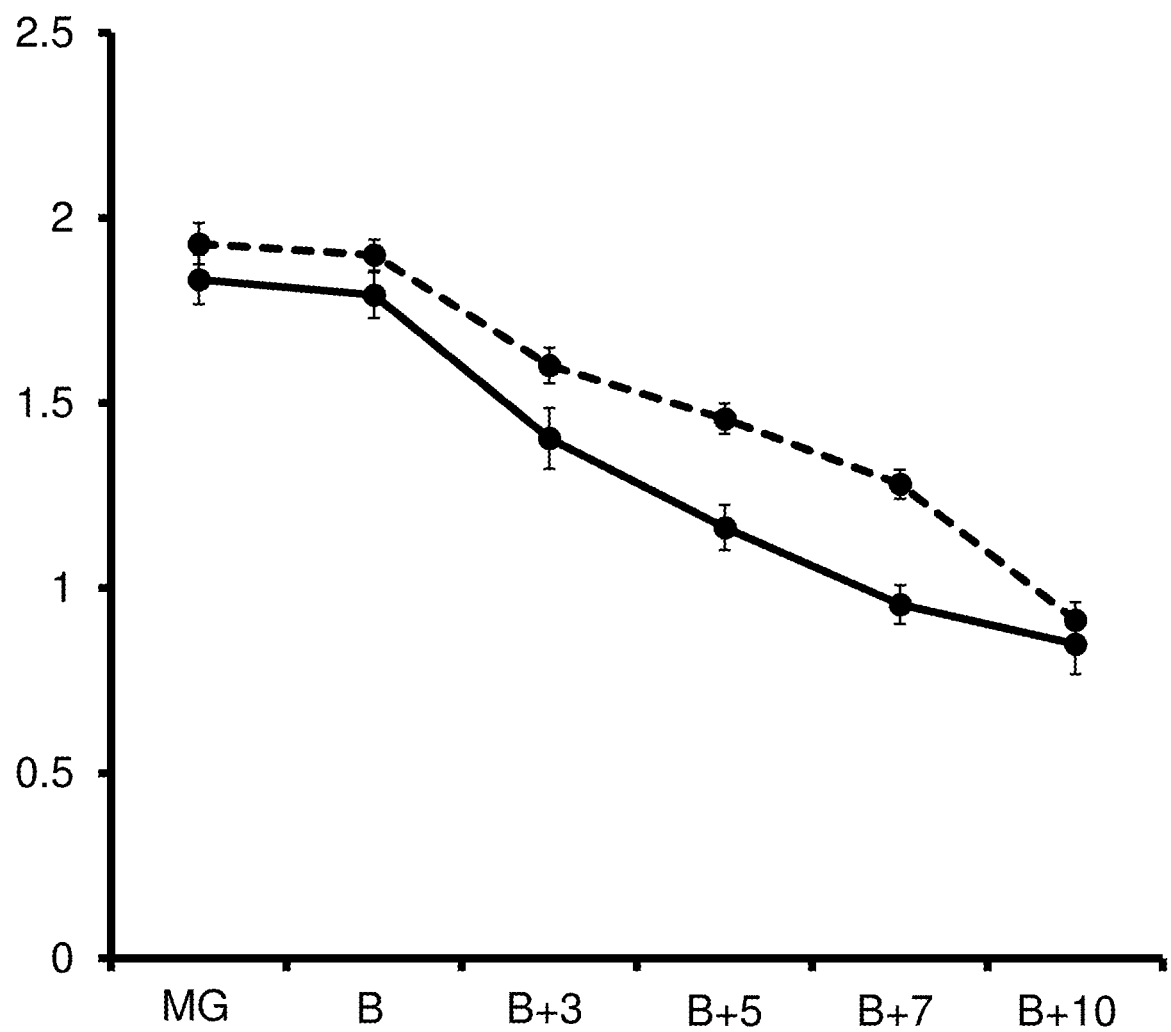
FIG. 2 Mechanical measurements on (Panel A) the outer pericarp and (Panel B) the inner pericarp of IL2-3F1 lines reveals enhanced fruit firmness up to and including the breaker+7 day stage in comparison with the M82 controls. Each graph shows the maximum load (N) on the Y-axis and fruit developmental stage on the X-axis. Line M82 is represented by a solid line. Line IL2-3 F1 is represented by a dotted line. Fruit development stages: MG, mature green stage; B, breaker stage; B+3, breaker stage plus 3 days; B+5, breaker stage plus 5 days; B+7, breaker stage plus 7 days; B+10, breaker stage plus 10 days.
Figure 2:
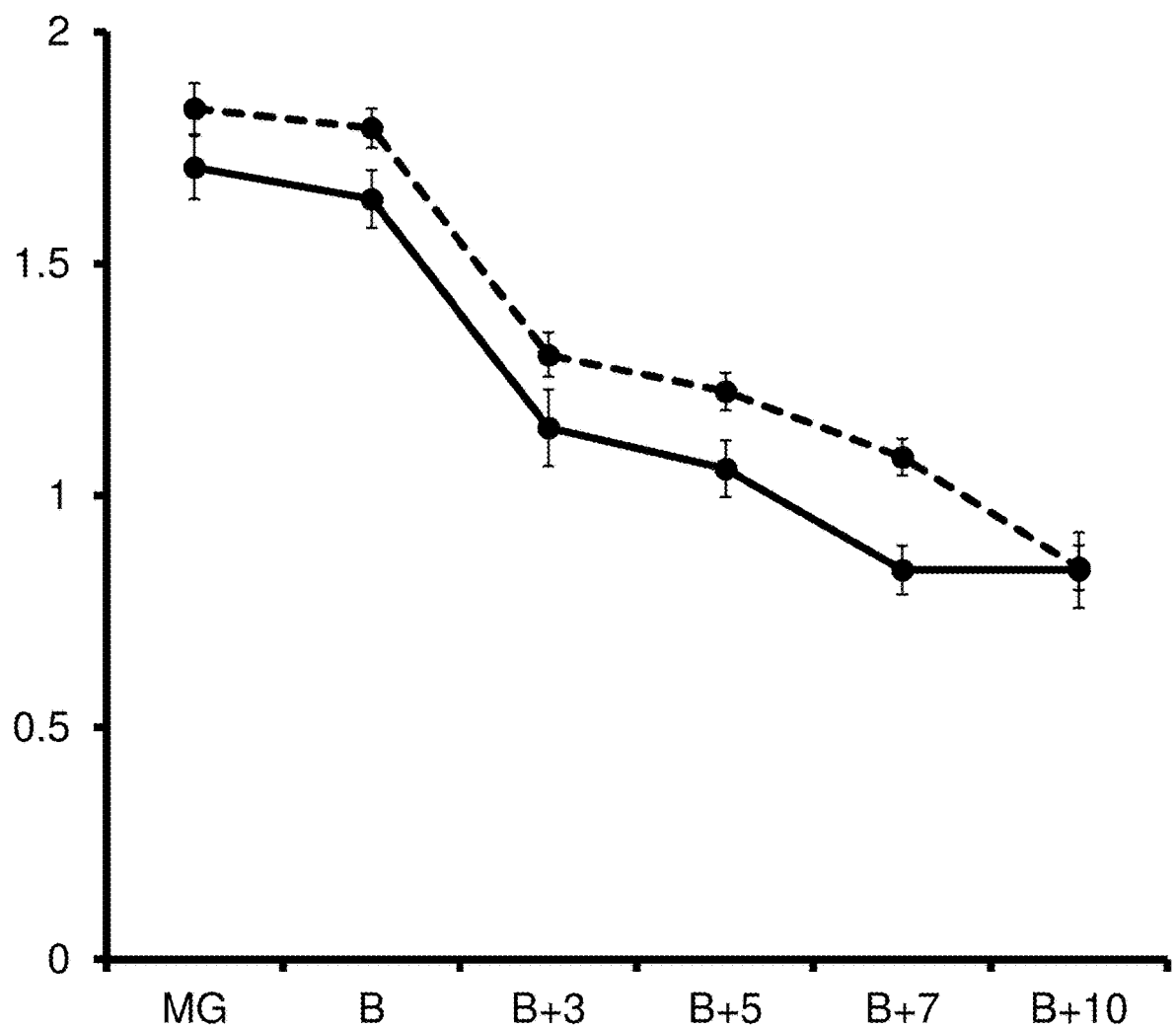

The ripening fruit of these F1 and F2 heterozygous lines were then tested for mechanical properties after growth under standard conditions. Fruits were collected at 7 days after the first sign of red colour (day post breaker). A transverse section was cut from the centre of the fruit using a double blade mounted on a customized cutting tool to give a section of exactly 6 mm. This section was placed on a flat plate. Using a Lloyd LRX machine equipped with a 10 N load cell, the force required to penetrate the outer and inner pericarp tissue by a 6 mm probe travelling at 10 mm/minute (maximum load) was then measured. This measurement was repeated 3 times for each pericarp layer on each fruit. Maximum load is the maximum resistance achieved whilst the probe is passing through the tissue. At least 5 fruit were taken from each line at each stage of development unless otherwise stated. The fruit of the IL2-3 parental line and those of the IL2-3 F1 lines retained significant firmness during the later stages of ripening in comparison with the M82 controls. For example, in comparison with M82, in IL2-3 F1 (FIG. 2, panels A+B), at B+5 and B+7 (the stage at which the fruit would be consumed) the outer pericarp was significantly ($P<0.01$) firmer at the equivalent stage of ripening. For the IL2-4 lines differences in fruit firmness were also apparent in comparison to M82 but low numbers of fruit due to blossom end rot in this line impeded proper statistical analysis. An additional IL for Chromosome 2 (IL2-3-1) was obtained from Dani Zamir. This covered just the upper end of the 2-3 introgression (corresponding to flanking markers CT176 and TG554), above the overlap between IL2-3 and 2-4. Fruits from this line had similar fruit firmness characteristics (i.e. maximum load) or were softer than M82 at all the stages of ripening (data not shown).

Fruits from all lines ripened to a fully red colour at B+7 (ie all the surface of the pericarp was red and this was also the case for internal pericarp tissues).

Example 4

Screening Seedlings for Recombination Events, Selecting Recombinants and Fruit Firmness Testing 10 Individual Fruit/Lines 1200 IL2-3×M82F2 and IL2-4×M82F3 seedlings were grown under standard growth conditions and DNA was extracted using standard methods from the first true leaf. Recombination events were screened for using both introgressions because of their large overlap in this region likely to harbour the QTL. Taqman-based markers were used to identify recombinant individuals. From the first 1200 lines, 89 recombinants were identified. One of these plants failed to produce a meristem and died. The remaining plants were rescreened through sequencing the SNPs and the genotypes of 78 individuals were verified. Ten lines scored as heterozygous by Taqman could not be confirmed by the SNP assay.

Example 5

Genotyping Recombinant Lines

The 78 recombinant individuals were then genotyped with a further 38 markers on the Syngenta SSR platform. Markers were ordered using JoinMap and then displayed in Microsoft Excel with genotype data for each line. Lines shown were selected to show a variety of the recombinants obtained (FIG. 3). These markers spanned the IL2-3 and 2-4 introgressions. These markers have been set more precisely within the context of the tomato genetic map by genotyping the recombinants with several additional SNP markers derived from RFLP resources (see QTL map in FIG. 7, panels A+B). The SSR platform reveals a random distribution of recombination events. Therefore with 78 recombinants across a 50 cM interval, substantial resolution of the fruit firmness QTL has been achieved.

Example 6

Figure 4:
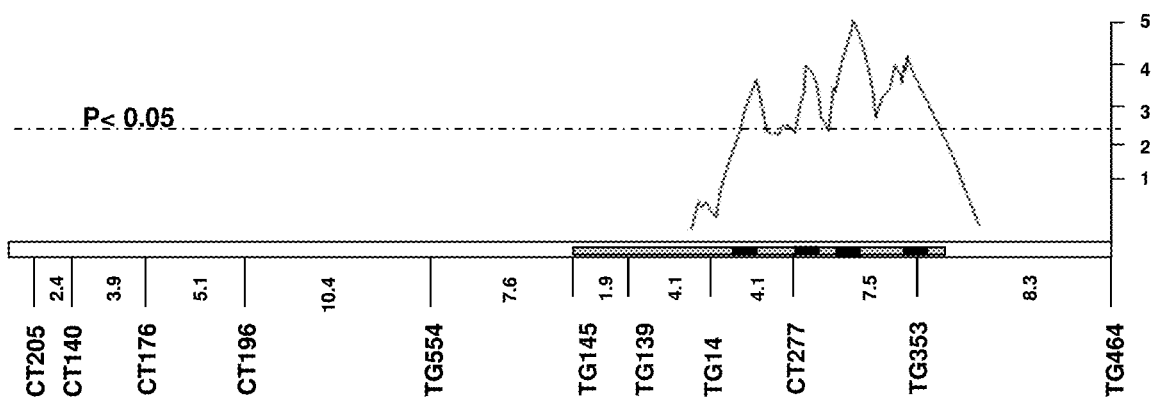
FIG. 4. Location of QTL for increased fruit firmness on tomato chromosome 2 as determined by measuring fruit firmness in (Panel A) the outer pericarp and (Panel B) the inner pericarp. QTLs are shown as black solid bars. For the outer pericarp, from left to right the QTLs correspond to QTL2, QTL4, QTL5 and QTL3. For the inner pericarp, from left to right the QTLs correspond to QTL1, QTL2, QTL4, QTL5 and QTL3. Marker positions and the distance between them (in centimorgans) are shown below the QTL positions on the X-axis. LOD score is shown on the Y-axis.
Figure 4:
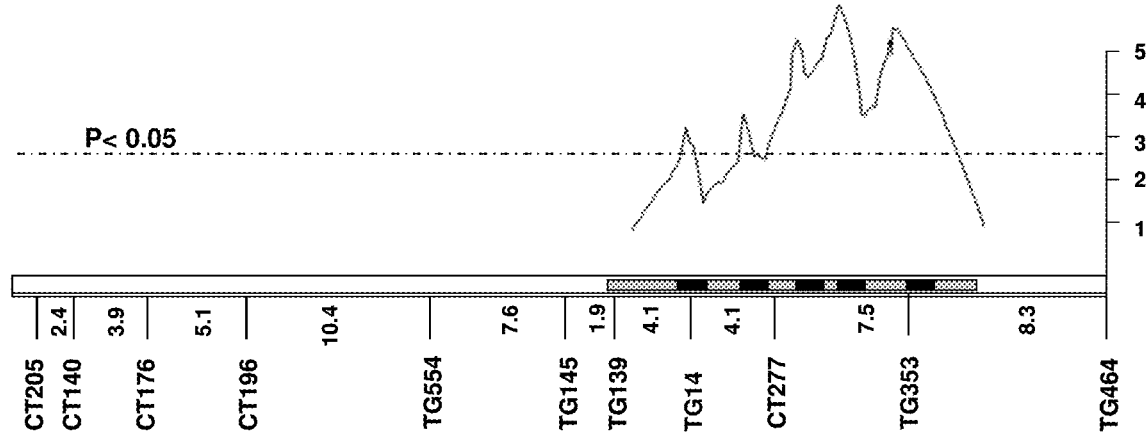

Establishment of a Mapping Interval of Less than 5 Centimorgans for Fruit Firmness QTL Fruit firmness measurements on 10 individual fruits at breaker+7 days from each of the 78 recombinant lines were made as described above. A region of less than 5 centimorgans (<5 cM) on which to focus positional cloning experiments was then delineated (FIG. 4, panels A+B). Markers flanking this region were developed from the tomato genetic map, genome sequence data and from the Syngenta ultra-high density map as necessary. These were then used to screen a further 6000 F2 seedlings for informative recombinants in the mapping interval (see example 8).

QTL1 is only present at breaker+7 days in the inner pericarp and not the outer pericarp (FIG. 4). QTL analysis was undertaken using several well established statistical packages including MapQTL and QTL Cartographer with essentially identical results: (van Ooijen J W, Maliepaard C (1996) MapQTL® version 4.0: Software for the calculation of QTL positions on genetic maps. CPRO-DLO, Wageningen; van Oijen J W, Voorips R E (2001) JoinMap® 3.0: Software for the calculation of genetic linkage maps. Plant Research International, Wageningen, Netherlands; Wang S., C. J. Basten, and Z.-B. Zeng (2007). Windows QTL Cartographer 2.5 Department of Statistics, North Carolina State University, Raleigh, N.C. (available at statgen.ncsu.edu/qticart/WQTLCart.htm).

Figure 5:
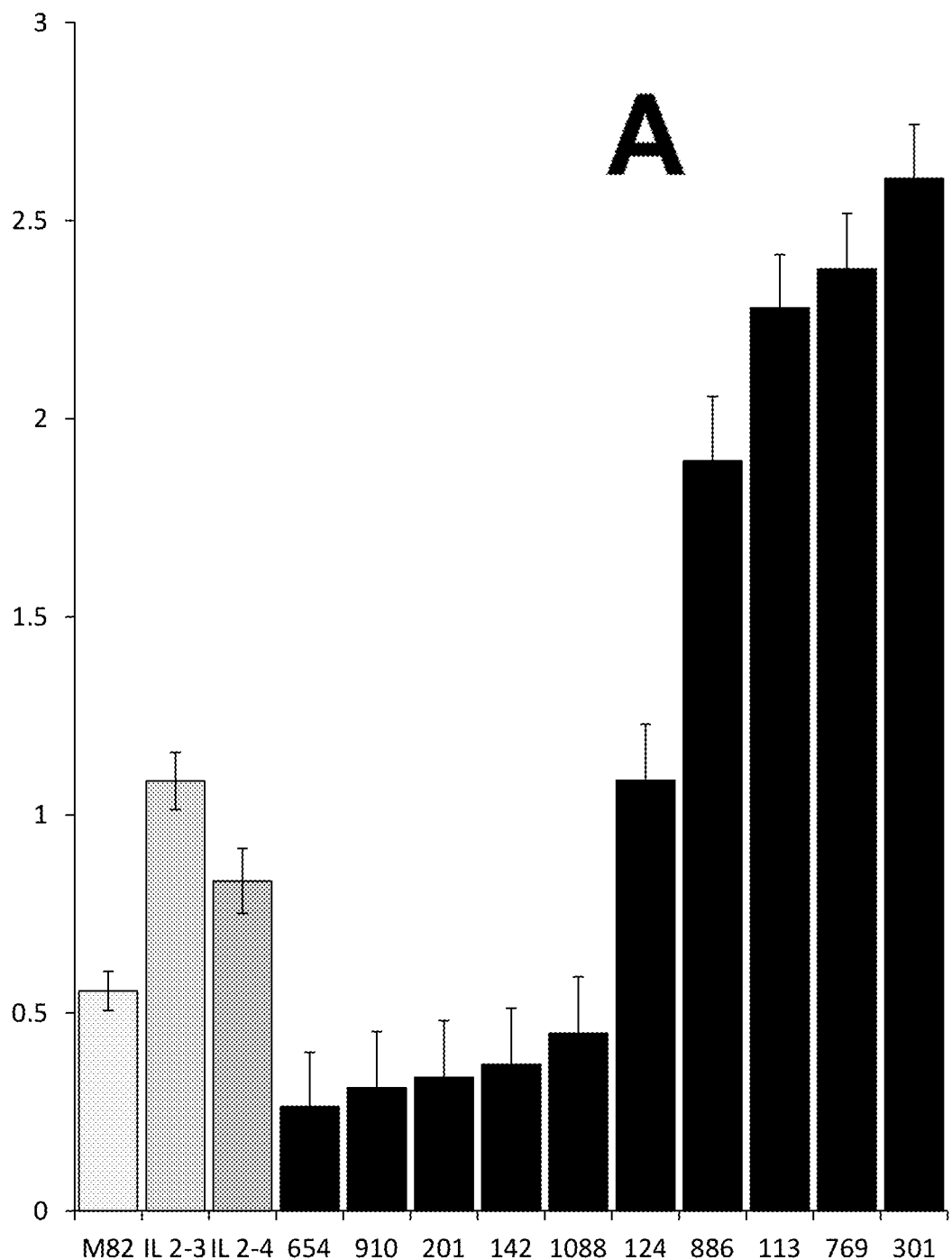
FIG. 5. Mean fruit firmness determinations on the outer and inner pericarp of selected heterozygous recombinant individuals and parent lines in 2007 and 2008. The Y axis shows maximum load (N) and the X-axis represents the line number. (Panel A) outer pericarp 2007; (Panel B) inner pericarp 2007; (Panel C) outer pericarp 2008; (Panel D) inner pericarp 2008.
Figure 5:
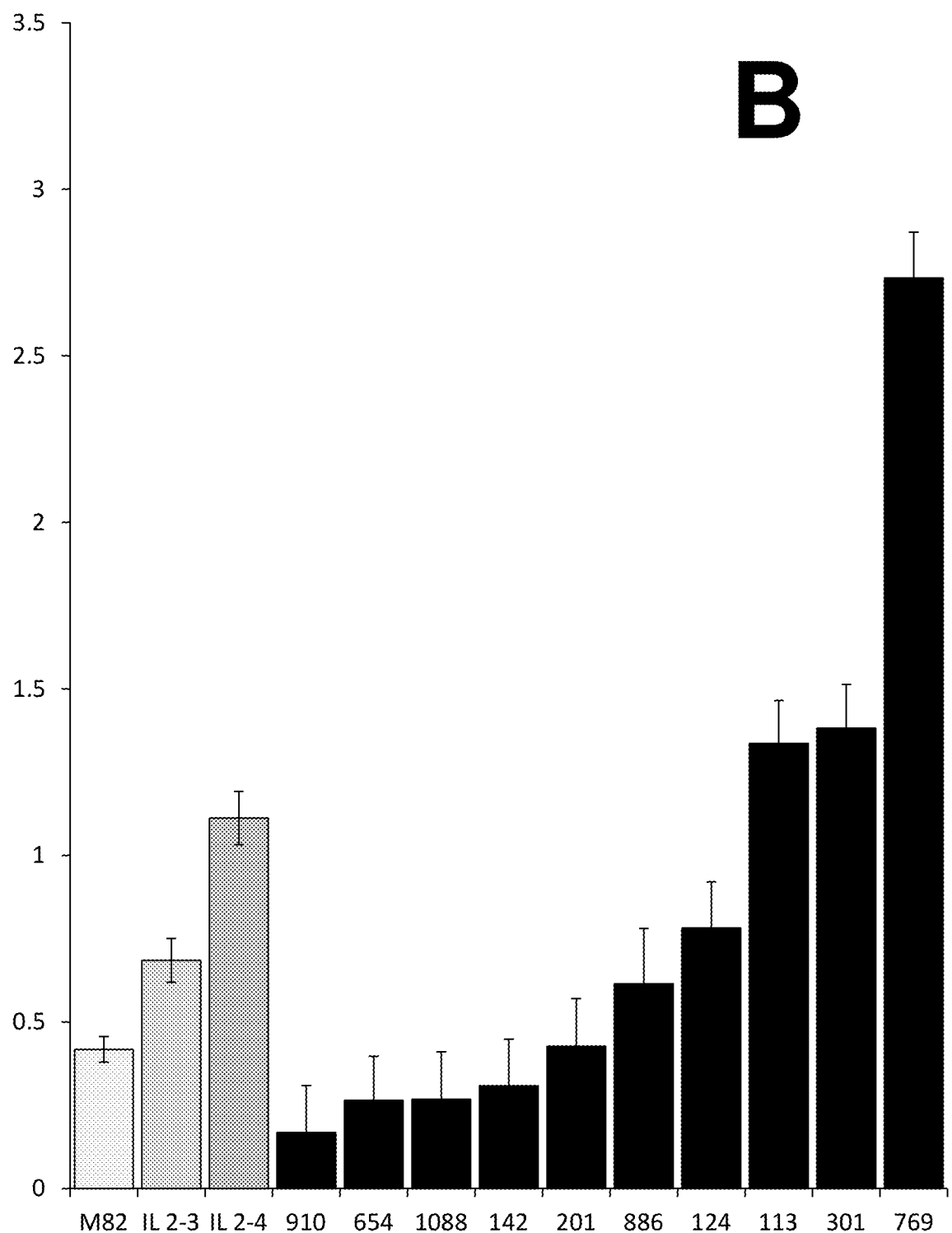
Figure 5:
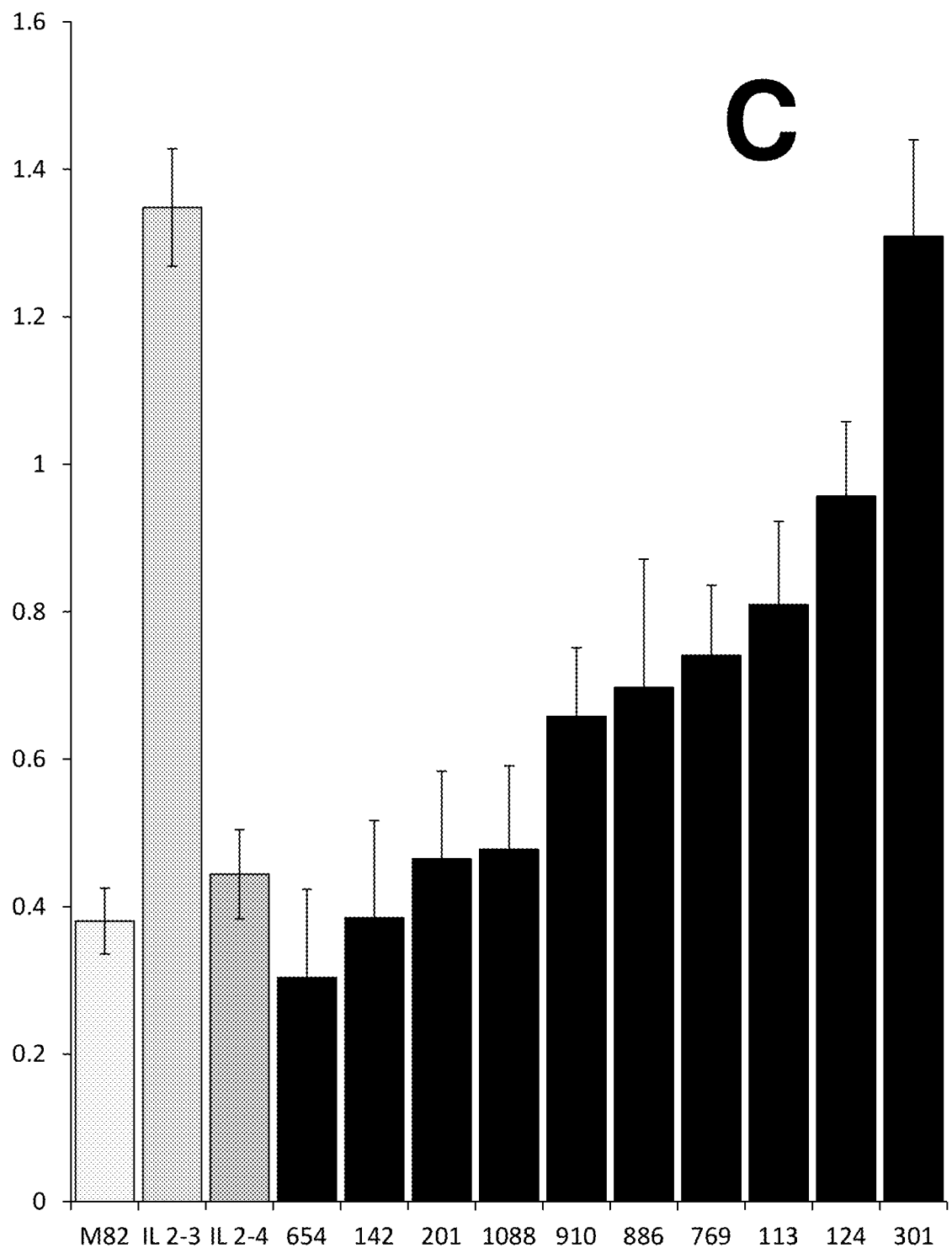
Figure 5:
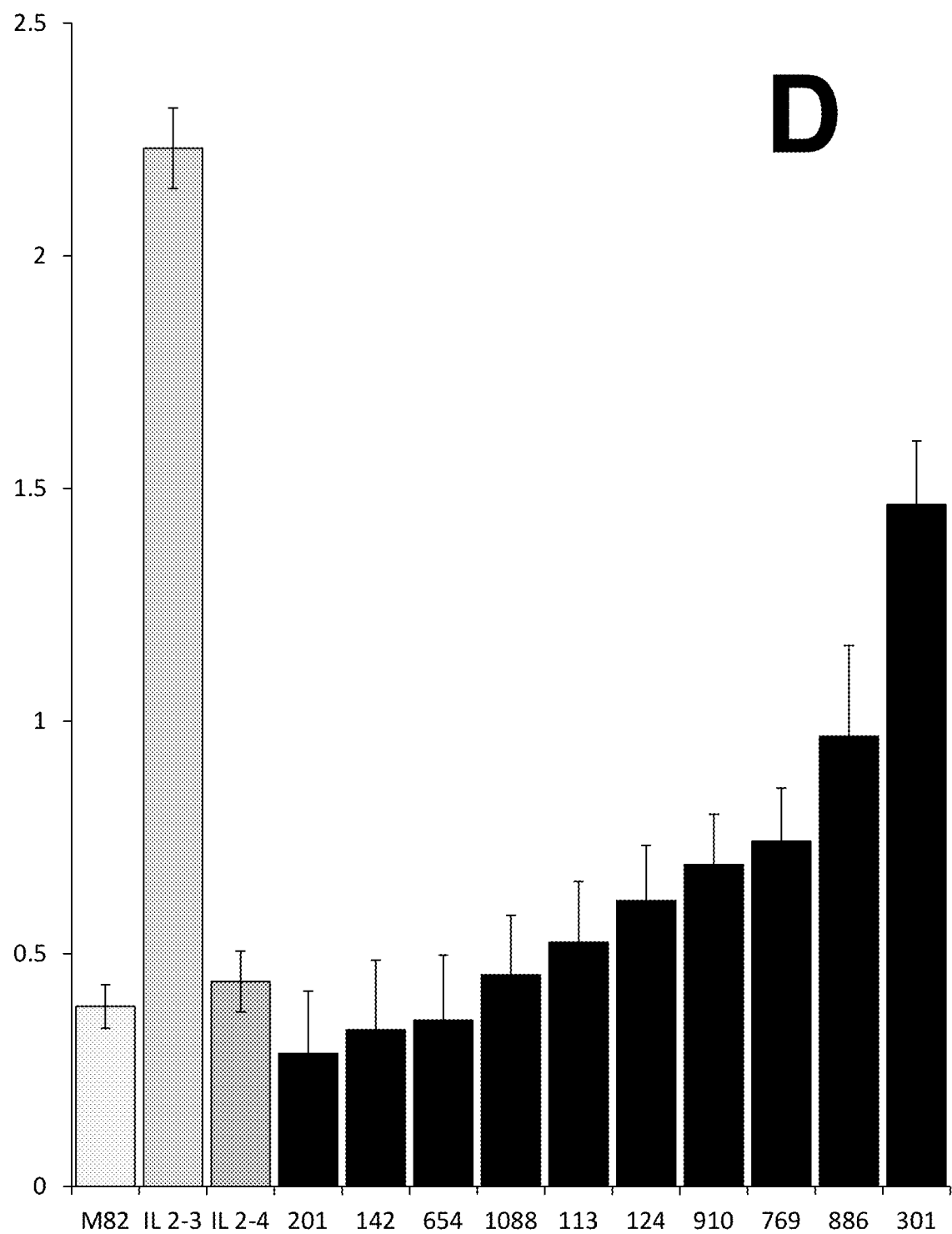

In certain sub-lines harbouring the major fruit firmness QTLs 1 to 5 substantial additive effects on fruit firmness were observed above those apparent in the IL parents (FIG. 5). These differences in fruit firmness are large and highly significant ($P<0.001$).

Example 7

Use of Syngenta's Tomato GeneChip to Compare Gene Expression in Chromosome 2 Between M82 and the Relevant Chromosome 2 Introgressions An experiment to investigate the profile of gene expression in IL2-3 in comparison to the M82 control was undertaken using the Syngenta Tomato GeneChip. For RNA extraction and tomato GeneChip analysis, flowers were tagged at anthesis before 12.00 noon on consecutive days. Fruit were collected from plants at: 15 days post anthesis (dpa) (immature green); 25 dpa (rapid expansion phase); 40 dpa (mature green); and 54 dpa (red ripe). Fruit were flash frozen in liquid nitrogen. Three fruit were pooled to represent one biological replicate. The RNA extraction protocol was based upon a method using the RNA extraction buffer RNAwiz™ (Ambion (Europe) Ltd. UK, Cat #9736) (following the manufacturer's protocol). Tomato GeneChip analysis was then undertaken.

Figure 6:
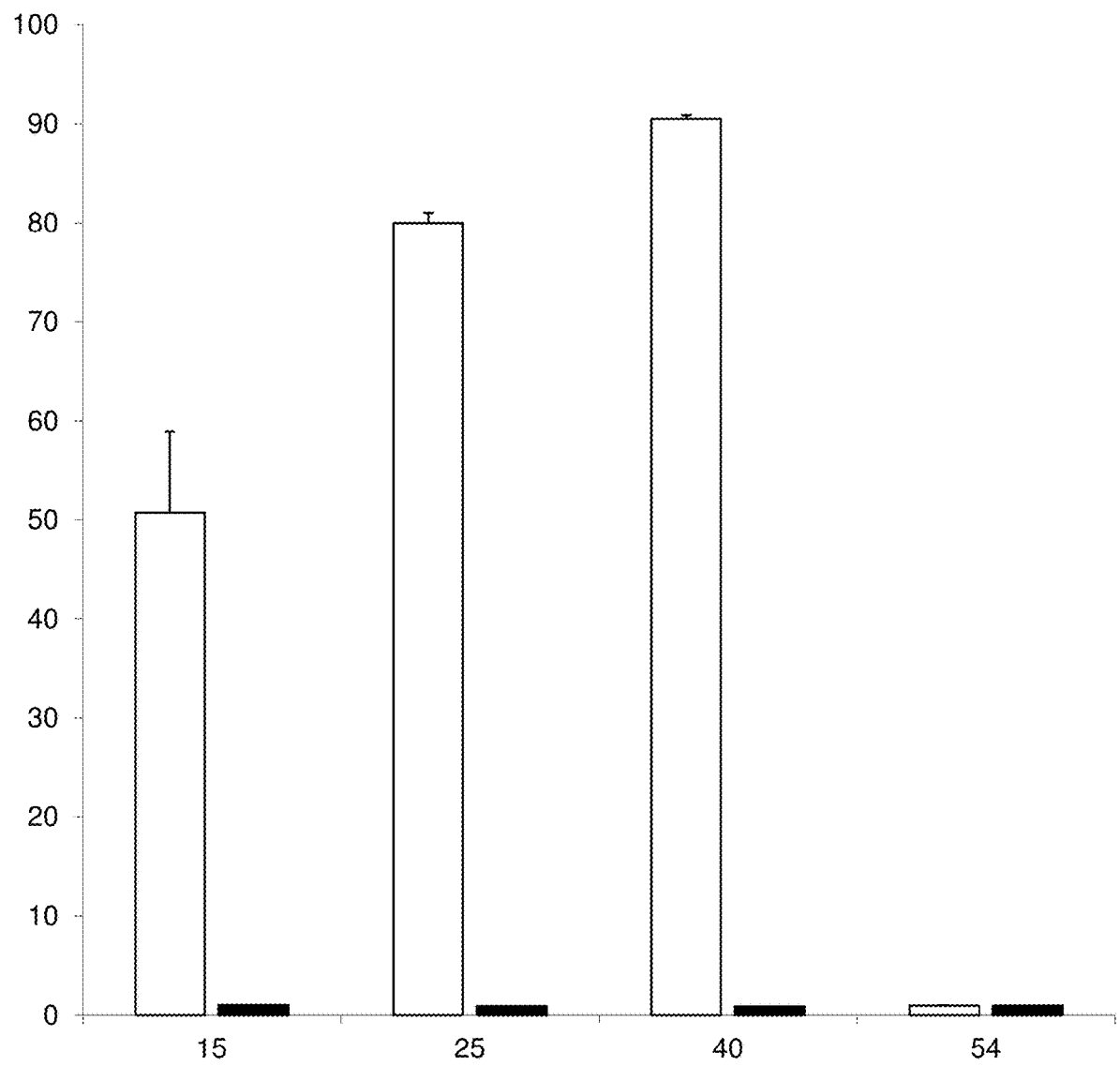
FIG. 6. Pectinmethylesterase/pectin methylesterase inhibitor (PME) showing high levels of expression in IL2-3 compared with the M82 parent. Normalised mRNA expression levels of PME are shown on the Y axis. Number of days post anthesis are shown on the X-axis. Key: white bars=IL2-3; solid bars=M82.

The array data was analysed by two-way ANOVA of genotype differences (GeneSpring, Agilent Technologies, UK was used to normalize the data and perform the statistical analysis). A large number of genes showed differential expression between M82 and line IL2-3 at 15, 25, 40 and 54 days post anthesis. The most apparent changes included elevated levels of a pectin methylesterase probe ID Le002389 in the IL2-3 line especially up to mature green at 40 days post anthesis (FIG. 6).

A total of 29 gene models were tested by RT-PCR against parental lines under QTL2, and 17 gene models were tested for each of QTLs 4 and 5.

mRNA concentration levels of ethylene responsive transcription factor 12 (QTL2), pectin methylesterase (QTL3), dof zinc finger protein 6 (QTL4) and an equilibrative nucleoside transporter family protein (QTL5) were measured in M82, IL2-4, IL2-3 and various recombinant lines at the mature green and breaker stages. Texture data was also obtained from the outer and inner pericarps of the corresponding fruits.

Figure 7:
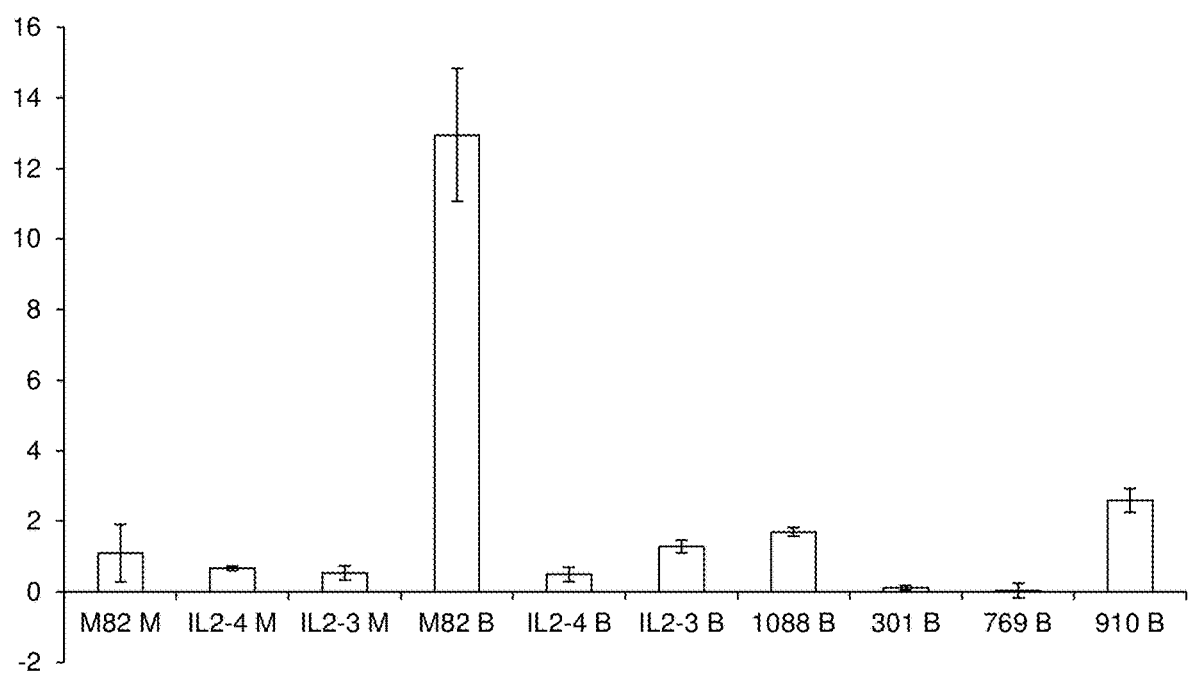
FIG. 7 Normalised relative mRNA concentrations of ethylene response factor 12 in lines M82, IL2-4, IL2-3, 1088, 301, 769 and 910 at the mature green stage (denoted M) or at the breaker stage (denoted B) as measured in (Panel A) outer pericarp and (Panel B) inner pericarp. Texture data from the same lines is shown for (Panel C) outer pericarp and (Panel D) inner pericarp. The letter H denotes the line has a heterozygous introgression.
Figure 7:
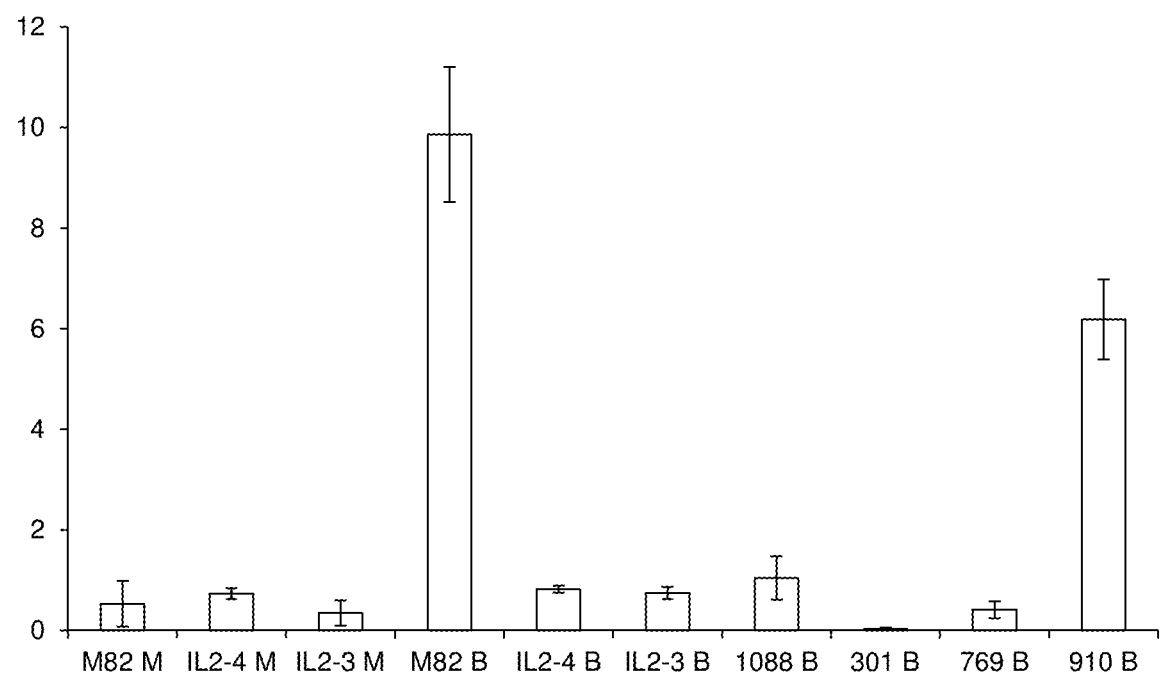
Figure 7:
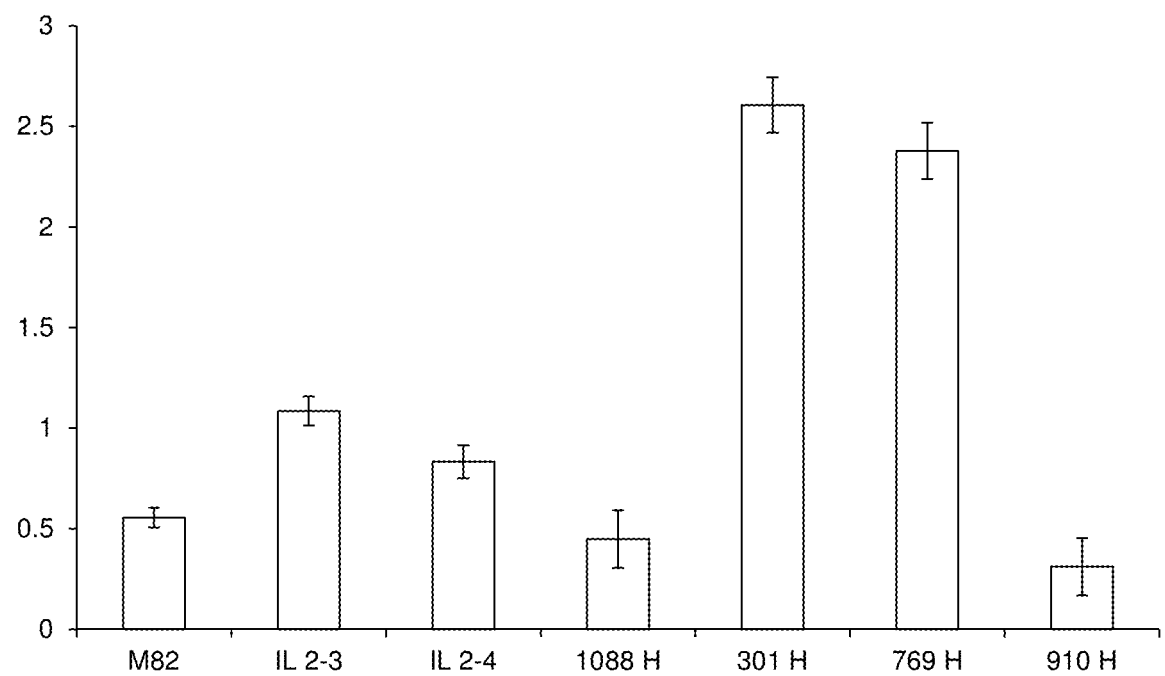
Figure 7:
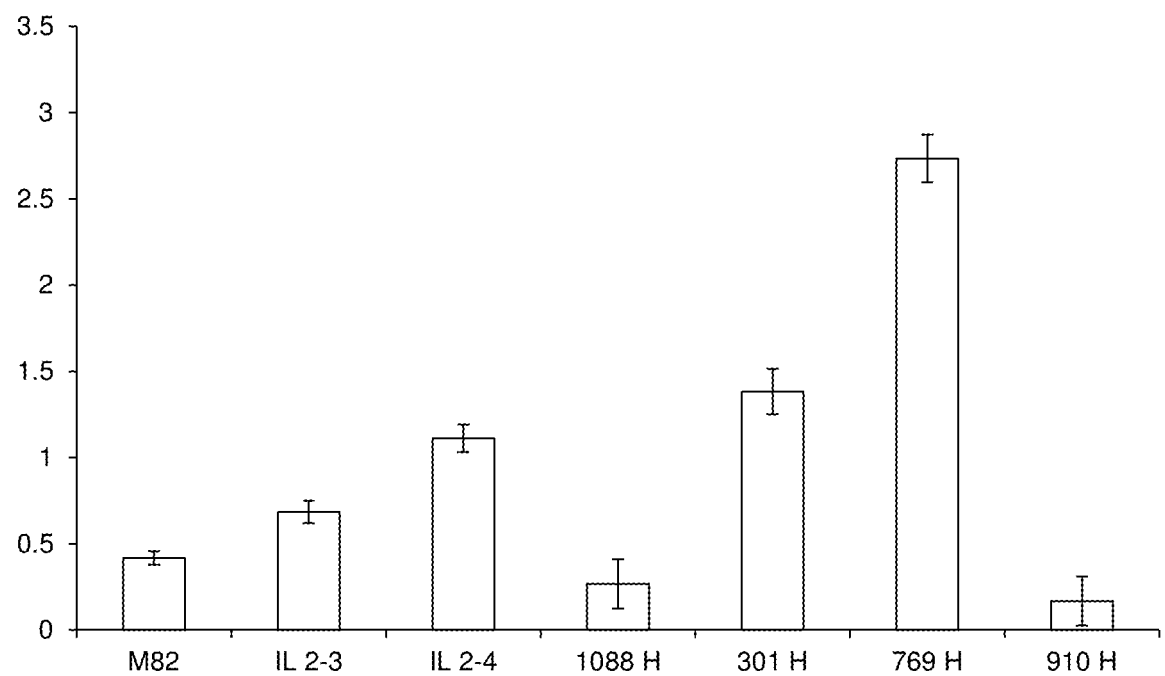

Ethylene responsive transcription factor 12 was expressed at high levels in M82 fruit at breaker stage but at low levels in introgression lines and some recombinant lines (FIG. 7). The low expression levels are seen especially in recombinant lines 301 and 769 which, as shown in FIG. 3, have a higher degree of introgression from *S. pennellii* than recombinant line 910. Corresponding texture data shows that recombinant lines 301 and 769 have firmer fruit than line 910.

Pectin methylesterase was expressed at low levels in M82 fruit but at high levels in introgression lines and some recombinant lines (FIG. 8). The high expression levels are seen especially in recombinant line 301 which, as shown in FIG. 3, has a higher degree of introgression from *S. pennellii* than recombinant lines 124 and 142. Corresponding texture data shows that recombinant line 301 has firmer fruit than lines 124 and 142.

Dof zinc finger protein 6 was expressed at high levels in M82 fruit but at low levels in introgression lines (FIG. 9). RT-PCR confirmed that a further candidate gene, an equilibrative nucleoside transporter family protein, was differentially expressed between M82 and introgression line IL2-3 (data not shown).

These results indicate the potential for influencing tomato fruit texture phenotypes using, for example, a GM approach which involves overexpressing or silencing the candidate genes above. It would appear that increased tomato fruit texture corresponds with higher levels of pectin methylesterase but lower levels of ethylene responsive transcription factor 12 and dof zinc finger protein 6.

Example 8

Figure 10:
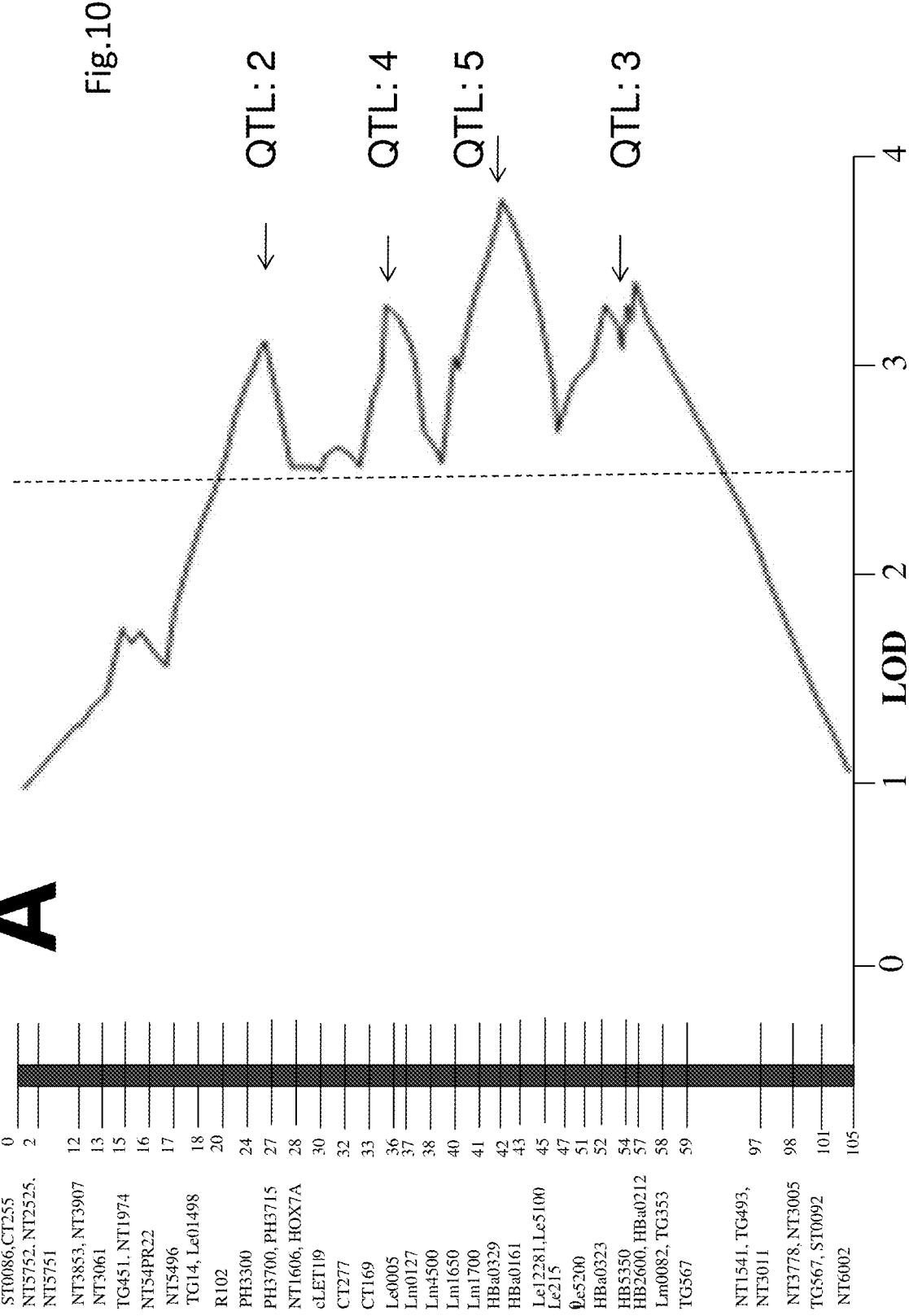
FIG. 10 (Panel A) Detailed QTL map for outer pericarp showing marker positions (Panel B) Detailed QTL map for inner pericarp showing marker positions.
Figure 10:
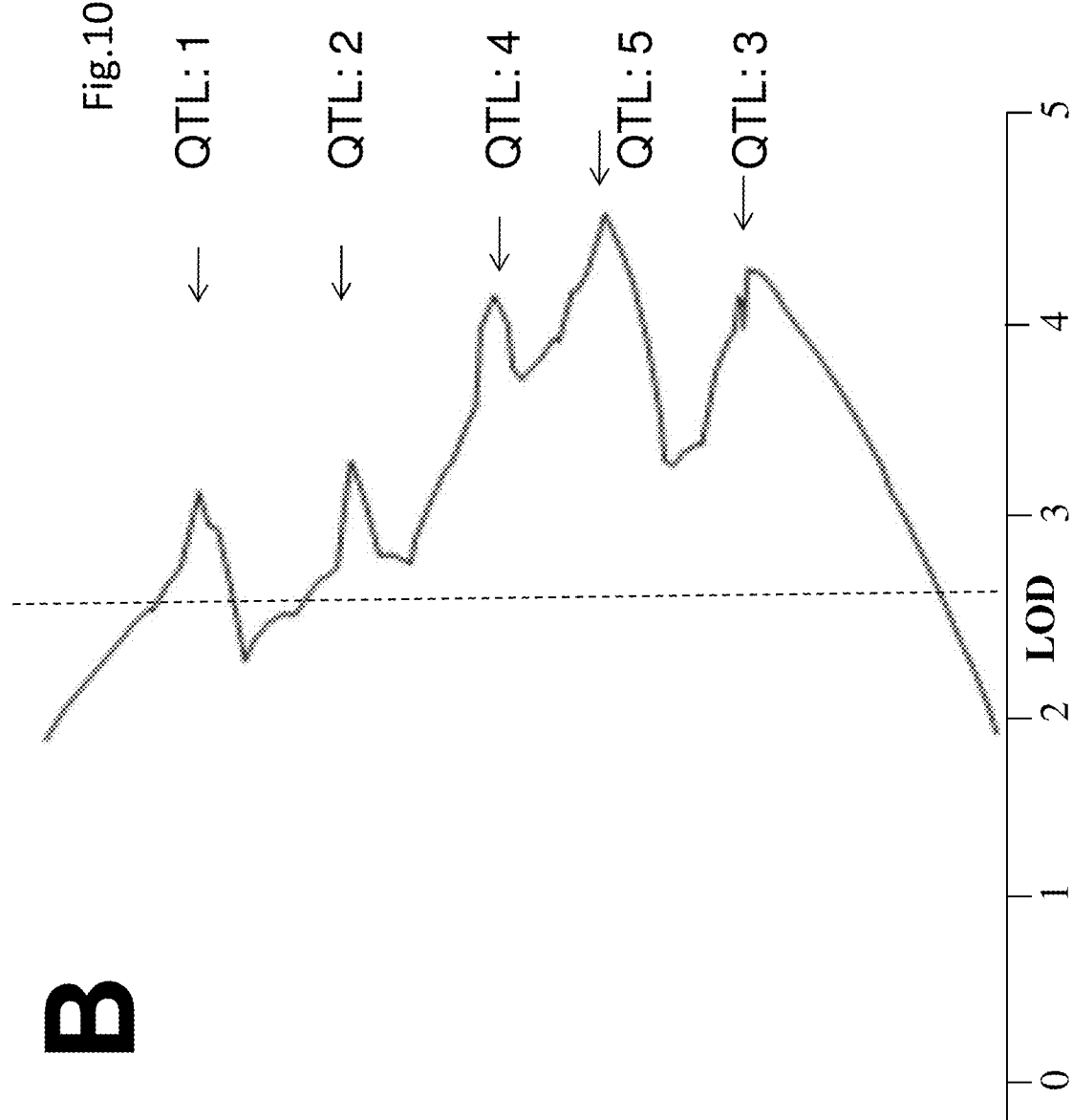

Further Resolution of the Mapping Intervals to Less than 0.5 Centimorgans by Screening an Additional F2 NIL Population of Approx. 4000 Individuals and Anchorage of the QTL to the Physical Map and Genome Sequence 6000 IL2-3×M82F2 individuals were grown under standard greenhouse conditions and screened for recombination events across an interval which included the major and minor QTL and the markers TG451 to TG353 (see FIG. 1). Of 6000 F2 lines genotyped, a total of 222 recombinants were recovered with only 42 additional recombinants falling within the mapping interval under the five QTLs. This gave a total of 120 useful recombinant individuals that were used to generate a QTL map (FIG. 10, panels A+B).

Example 9

Nomination of Candidate Fruit Firmness-Related Genes

In addition to DNA molecular marker information this invention also relates to the identification of putative candidate genes that control the described trait. These QTL have been characterised at the molecular level and candidate genes at these loci have been identified. The current list of candidate genes is as follows: QTL1, TG451 a MADS-box transcription factor related by sequence to *Petunia* gene pMADS3, a similar gene is involved in the regulation of early chloroplast development in *Arabidopsis* (Chi et al (2008)). QTL2, ethylene responsive transcription factor 12

(SL1.00sc00226_365.1). QTL3, a pectinesterase/pectinesterase inhibitor (Syngenta GeneChip probe ID, Le0023899).

Where possible, QTL have been anchored to the tomato physical map. The candidate sequence for QTL3 is one of 3 putative pectinesterase (pme)/pectinesterase inhibitor genes. The probe on the Syngenta array shows homology with all 3 of these pme genes. These genes are so similar in sequence it is difficult to distinguish their individual expression patterns even using 3' end sequence. The three unigenes are SGN-U585819, SGN-U585820, SGN-U58523.

QTL4 candidate gene is the open reading frame corresponding to dof zinc finger protein 6 (SL1.00sc00226_436.1.1) position 4475868 to 4476845 (+ strand). QTL5 candidate gene is the open reading frame corresponding to equilibrative nucleoside transporter family protein (SL1.00sc00226_511.1) position 5133572 to 5135660 (− strand).

Example 10

Marker Sequences as Used Herein

TABLE 3

Primers and PCR conditions used to generate markers that delineate QTL region on chromosome 2.

| SEQ ID | Primer Name | Primer Sequence | Marker Type | Annealing Temperature (degrees celcius) |
|---|---|---|---|---|
| 1 | NT3853F | GGATTGTGTTATCTCCGATG | SSR | 59° C. |
| 2 | NT3853R | GAAAAAGGGAAGAGATGGG | SSR | 59° C. |
| 3 | NT3907F | GAACAGTTTCCGGTGGAG | SSR | 59° C. |
| 4 | NT3907R | TTGGGCCAGGAAGAAAAC | SSR | 59° C. |
| 5 | TG14F | GCCAACTGATTGCCTATCCT | SNP marker | 59° C. |
| 6 | TG14R | CTCACTCCACCCATCACAAC | SNP marker | 59° C. |
| 7 | HOX7AF | TGACTCCGGCAAATTTCTCT | SNP marker | 59° C. |
| 8 | HOX7AR | TCCCCCATGTATGGACTGAT | SNP marker | 59° C. |
| 9 | CT277F | TGGTAACCTGCTGTGGTCAA | SNP marker | 59° C. |
| 10 | CT277R | AGGTAAACCGCCAGCTCATT | SNP marker | 59° C. |
| 11 | Lm0127F | GAAAGGATGCAGCCAAAAAT | SNP marker | 59° C. |
| 12 | Lm0127R | TACTCTAAGGGCGCACAATG | SNP marker | 59° C. |
| 13 | Lm1650F | AGGTTGGCAGAAGACGAAGA | SNP marker | 59° C. |
| 14 | Lm1650R | ACATCCCAAAGAGCTCCAGA | SNP marker | 59° C. |
| 15 | LE5100F | TGTTCCAAACGCCTAAAACC | SNP marker | 59° C. |
| 16 | LE5100R | TTCCCCAAGTGATTCCTCAG | SNP marker | 59° C. |
| 17 | LE5200F | TTTGTACAAGCGGCACAAAG | SNP marker | 59° C. |
| 18 | LE5200R | CAGCTCGCGTCATCTCATTA | SNP marker | 59° C. |
| 19 | HB2600F | AGGGAGGCTGTGGGTAAGAT | SNP marker | 59° C. |
| 20 | HB2600R | GGCACCTAGACCAAATCCAA | SNP marker | 59° C. |
| 21 | TG353F | CAGAGCCTGATCTTTCACCA | SNP marker | 59° C. |

TABLE 3-continued

Primers and PCR conditions used to generate markers that delineate QTL region on chromosome 2.

| SEQ ID | Primer Name | Primer Sequence | Marker Type | Annealing Temperature (degrees celcius) |
|---|---|---|---|---|
| 22 | TG353R | TTCGTGTTGGAGATGGAAAG | SNP marker | 59° C. |

TABLE 4

| Marker | Allele size of M82 (bp) | Allele size of LA716 (bp) | Precision (bp) | Method of measurement |
|---|---|---|---|---|
| NT3853 | 102 | 96 | ±2 | sequencer |
| NT3907 | 192 | 195 | ±1 | sequencer |
| TG14 | 381 | 381 | ±1 | sequencer |
| HOX7A | 257 | 257 | ±1 | sequencer |
| CT277 | 400 | 450 | ±20 | Agarose gel |
| Lm0127 | 223 | 222 | ±1 | sequencer |
| Lm1650 | 252 | 252 | ±1 | sequencer |
| LE5100 | 278 | 278 | ±1 | sequencer |
| LE5200 | 197 | 204 | ±3 | sequencer |
| HB2600 | 246 | 246 | ±1 | sequencer |
| TG353 | 368 | 367 | ±1 | sequencer |

What is claimed is:

1. A method for selecting a cultivated *Solanum lycopersicum* plant that provides fruit with increased firmness of the inner pericarp as compared with fruit from a control *Solanum lycopersicum* plant, the method comprising:
   a) detecting in the cultivated *Solanum lycopersicum* plant the presence of QTL2 on chromosome 2, and
   b) selecting a cultivated *Solanum lycopersicum* plant that includes the presence of said QTL2, thereby selecting a cultivated *Solanum lycopersicum* plant that provides fruit with increased firmness of the inner pericarp as compared with fruit from a control *Solanum lycopersicum* plant;
   wherein detecting the presence of said QTL2 in the cultivated *Solanum lycopersicum* plant comprises:
   i) providing a sample of genomic DNA from the cultivated *Solanum lycopersicum* plant, and
   ii) detecting in the sample of genomic DNA at least one DNA marker including HOX7A, wherein HOX7A can be detected by a forward primer of SEQ ID NO: 7 and a reverse primer of SEQ ID NO: 8; and
   wherein the increased fruit firmness of the inner pericarp is from between 1.2 to 2 times greater at the harvesting stage than that of fruit from the control *Solanum lycopersicum* plant.

2. The method of claim 1, wherein the harvesting stage is the mature green stage.

3. A method of introgressing a trait for increased fruit firmness from a donor *Solanum lycopersicum* plant, which provides fruit with increased firmness of the inner pericarp as compared with fruit from a control *Solanum lycopersicum* plant, into a recipient *Solanum lycopersicum* plant, the method comprising:
   a) crossing the donor *Solanum lycopersicum* plant with the recipient *Solanum lycopersicum* plant to provide offspring *Solanum lycopersicum* plants,
   b) detecting in offspring *Solanum lycopersicum* plants the presence of QTL2 on chromosome 2, and
   c) selecting an offspring *Solanum lycopersicum* plant that includes the presence of said QTL2, thereby introgressing the trait for increased fruit firmness of the inner pericarp from the donor *Solanum lycopersicum* plant into the recipient *Solanum lycopersicum* plant;
   wherein detecting in offspring *Solanum lycopersicum* plants the presence of said QTL2 comprises isolating a sample of genomic DNA from the offspring *Solanum lycopersicum* plant and detecting in the sample of genomic DNA at least one DNA marker including HOX7A, wherein HOX7A can be detected by a forward primer of SEQ ID NO: 7 and a reverse primer of SEQ ID NO: 8.

4. A method of introducing a trait for increased fruit firmness of the inner pericarp into a hybrid *Solanum lycopersicum* variety, the method comprising:
   a) crossing a donor *Solanum lycopersicum* plant that provides fruit with increased firmness of the inner pericarp as compared with fruit from a control *Solanum lycopersicum* plant with a recipient inbred *Solanum lycopersicum* plant to provide F1 progeny plants,
   b) selecting F1 progeny plant(s) that have increased fruit firmness of the inner pericarp,
   c) backcrossing the selected progeny plant(s) of b) with the recipient inbred *Solanum lycopersicum* plant to produce backcross progeny plants,
   d) selecting for backcross progeny plants of c) that have increased fruit firmness of the inner pericarp and morphological and physiological characteristics of the recipient inbred *Solanum lycopersicum* plant, wherein the selecting steps for increased fruit firmness comprises:
   (i) isolating genomic DNA of the backcross progeny, and
   (ii) testing the isolated genomic DNA for the presence of at least one molecular marker for QTL2 on chromosome 2, which comprises detecting in a sample of said isolated genomic DNA at least the DNA marker HOX7A, wherein HOX7A can be detected by a forward primer of SEQ ID NO: 7 and a reverse primer of SEQ ID NO: 8, and
   e) repeating steps c) and d) two or more times in succession to produce selected third or higher backcross progeny,
   f) optionally selfing selected backcross progeny in order to identify homozygous plants, and
   g) crossing at least one of the backcross progeny or selfed plants with another inbred *Solanum lycopersicum* plant to generate a hybrid *Solanum lycopersicum* variety with increased fruit firmness of the inner pericarp and all the morphological and physiological characteristics of a control hybrid *Solanum lycopersicum* variety from the same two parents in the absence of the trait for increased fruit firmness of the inner pericarp when grown under the same environmental conditions.

* * * * *